US010867012B2

(12) United States Patent
Agrawal et al.

(10) Patent No.: US 10,867,012 B2
(45) Date of Patent: Dec. 15, 2020

(54) DATA ANALYTICS AND INSIGHT DELIVERY FOR THE MANAGEMENT AND CONTROL OF DIABETES

(71) Applicant: MEDTRONIC MINIMED, INC., Northridge, CA (US)

(72) Inventors: Pratik Agrawal, Sherman Oaks, CA (US); Chantal M. McMahon, Los Angeles, CA (US); Yuxiang Zhong, Arcadia, CA (US); Boyi Jiang, Northridge, CA (US); Michael P. Stone, Lakewood, CA (US); Huzefa F. Neemuchwala, Simi Valley, CA (US); Kelly F. Joy, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 363 days.

(21) Appl. No.: 15/240,891

(22) Filed: Aug. 18, 2016

(65) Prior Publication Data
US 2017/0053072 A1 Feb. 23, 2017

Related U.S. Application Data

(60) Provisional application No. 62/208,479, filed on Aug. 21, 2015, provisional application No. 62/266,820, (Continued)

(51) Int. Cl.
*G06F 19/00* (2018.01)
*A61B 5/00* (2006.01)
(Continued)

(52) U.S. Cl.
CPC .......... *G06F 19/324* (2013.01); *A61B 5/0022* (2013.01); *A61B 5/14532* (2013.01);
(Continued)

(58) Field of Classification Search
CPC combination set(s) only.
See application file for complete search history.

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 3/1995
EP 0319268 11/1988
(Continued)

OTHER PUBLICATIONS

PCT Search Report (PCT/US02/03299), Oct. 31, 2002, Medtronic Minimed, Inc.
(Continued)

*Primary Examiner* — Michael Tomaszewski
*Assistant Examiner* — William T. Monticello
(74) *Attorney, Agent, or Firm* — Lorenz & Kopf, LLP

(57) ABSTRACT

A computer-implemented system and related method of managing use of a diabetes management device are presented here. An embodiment of the method obtains input data for a user of the diabetes management device, and compares the input data against historical event/outcome combinations maintained for the user. Each of the event/outcome combinations includes insight event data indicative of a glycemic event and a glycemic outcome corresponding to the insight event data. The method determines, based on the comparing, a correlation between the input data and a glycemic outcome. The method continues by generating a glycemic insight message for delivery to the user, wherein the glycemic insight message includes information regarding a relationship between at least some of the input data and the glycemic outcome.

14 Claims, 19 Drawing Sheets

Related U.S. Application Data filed on Dec. 14, 2015, provisional application No. 62/286,828, filed on Jan. 25, 2016, provisional application No. 62/304,605, filed on Mar. 7, 2016, provisional application No. 62/304,609, filed on Mar. 7, 2016, provisional application No. 62/304,615, filed on Mar. 7, 2016, provisional application No. 62/304,618, filed on Mar. 7, 2016, provisional application No. 62/329,021, filed on Apr. 28, 2016.

(51) Int. Cl.

| | | |
|---|---|---|
| *A61B 5/145* | (2006.01) | |
| *A61M 5/172* | (2006.01) | |
| *G16H 50/20* | (2018.01) | |
| *A61M 5/142* | (2006.01) | |
| *G16H 40/63* | (2018.01) | |
| *G16H 70/00* | (2018.01) | |
| *G06Q 10/10* | (2012.01) | |
| *A61M 5/00* | (2006.01) | |
| *G09B 5/12* | (2006.01) | |
| *G09B 19/00* | (2006.01) | |
| *A61M 5/14* | (2006.01) | |

(52) U.S. Cl.
CPC .......... *A61B 5/14542* (2013.01); *A61B 5/486* (2013.01); *A61B 5/4848* (2013.01); *A61B 5/7275* (2013.01); *A61B 5/7282* (2013.01); *A61B 5/742* (2013.01); *A61B 5/743* (2013.01); *A61B 5/7405* (2013.01); *A61B 5/746* (2013.01); *A61M 5/003* (2013.01); *A61M 5/142* (2013.01); *A61M 5/1723* (2013.01); *G06F 19/3418* (2013.01); *G06Q 10/109* (2013.01); *G09B 5/125* (2013.01); *G09B 19/0092* (2013.01); *G16H 40/63* (2018.01); *G16H 50/20* (2018.01); *G16H 70/00* (2018.01); *A61M 2005/1402* (2013.01); *A61M 2205/18* (2013.01); *A61M 2205/3584* (2013.01); *A61M 2205/502* (2013.01); *A61M 2205/52* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |

(56) References Cited

U.S. PATENT DOCUMENTS

| | | | |
|---|---|---|---|
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1* | 2/2001 | Benkowski et al. | |
| 6,246,992 B1 | 6/2001 | Brown | |
| 6,259,937 B1 | 7/2001 | Schulman et al. | |
| 6,329,161 B1 | 12/2001 | Heller et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1* | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,621,893 B2 | 11/2009 | Moberg et al. | |
| 8,185,412 B1 | 5/2012 | Harpale | |
| 8,639,214 B1* | 1/2014 | Fujisaki | H04M 11/00 |
| 10,216,767 B2* | 2/2019 | Bousamra et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2002/0161756 A1* | 10/2002 | Fesq et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0159656 A1 | 7/2005 | Hockersmith et al. | |
| 2005/0182675 A1 | 8/2005 | Huettner | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2009/0081951 A1 | 3/2009 | Erdmann et al. | |
| 2009/0082635 A1 | 3/2009 | Baldus et al. | |
| 2012/0053843 A1* | 3/2012 | Tubb | G06F 19/00 702/19 |
| 2013/0164718 A1 | 6/2013 | Buck et al. | |
| 2013/0321425 A1* | 12/2013 | Greene et al. | G06T 11/206 345/440 |
| 2014/0046685 A1 | 2/2014 | Ramasubramanian et al. | |
| 2014/0058237 A1 | 2/2014 | Galley et al. | |
| 2014/0068487 A1* | 3/2014 | Steiger et al. | G06F 3/0481 715/771 |
| 2014/0188398 A1 | 7/2014 | Cohen et al. | |
| 2015/0351673 A1* | 5/2015 | Vanslyke et al. | A61B 5/1495 |
| 2015/0178331 A1 | 6/2015 | Tyagi et al. | |
| 2015/0289823 A1* | 10/2015 | Rack-Gomer et al. | |
| 2016/0029966 A1* | 2/2016 | Salas-Boni et al. | A61B 5/7203 |
| 2016/0328990 A1* | 11/2016 | Simpson et al. | G09B 19/00 |
| 2016/0354543 A1* | 12/2016 | Cinar et al. | A61M 5/1723 |
| 2016/0357393 A1* | 12/2016 | Gross | |
| 2017/0249713 A1* | 8/2017 | Serbinis et al. | |

FOREIGN PATENT DOCUMENTS

| | | |
|---|---|---|
| EP | 0806738 | 11/1997 |
| EP | 0880936 | 12/1998 |

(56) References Cited

FOREIGN PATENT DOCUMENTS

| EP | 1338295 | 8/2003 |
|---|---|---|
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/05702 A2 | 1/2002 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Vide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," the Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.

(56) References Cited

OTHER PUBLICATIONS

Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714.

Jönsson, G., et al., "An Electromechanical Sensor for Hydrogen Peroxide Based on Peroxidase Adsorbed on a Spectrographic Graphite Electrode," Electroanalysis, 1989, pp. 465-468.

Kanapieniene, J. J., et al., "Miniature Glucose Biosensor with Extended Linearity," Sensors and Actuators, B. 10, 1992, pp. 37-40.

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.

Kimura, J., et al., "An Immobilized Enzyme Membrane Fabrication Method," Biosensors 4, 1988, pp. 41-52.

Koudelka, M., et al., "In-vivo Behaviour of Hypodermically Implanted Microfabricated Glucose Sensors," Biosensors & Bioelectronics 6, 1991, pp. 31-36.

Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—a Valuable Tool Not Only for a Self-Blood Glucose Monitoring but for a Wearable Artiffical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," the Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

Aapo Hyvarinen, et al., Independent Component Analysis: A Tutorial, Apr. 1999, Helsinki University of Technology, Laboratory of Computer and Information Science, Espoo, Finland.

* cited by examiner

644

| SPEAR | SHIELD | ACTION |
|---|---|---|
| HAS HYPO | HAS HYPO | KEEP BOTH |
| | HAS SEVERE HYPO | KEEP BOTH |
| | HAS HYPER | SEND SHIELD TO 'REMAINING INSIGHTS' |
| | HAS SEVERE HYPER | SEND SHIELD TO 'REMAINING INSIGHTS' |
| | TIME IN HYPO WORSE | KEEP BOTH |
| | TIME IN HYPER WORSE | SEND SHIELD TO 'REMAINING INSIGHTS' |
| | TIME IN CONTROL BETTER | SEND SHIELD TO 'REMAINING INSIGHTS' |
| | CONTROL IN RANGE ABOVE EIGHTY | SEND SHIELD TO 'REMAINING INSIGHTS' |
| HAS SEVERE HYPO | HAS HYPO | KEEP BOTH |
| | HAS SEVERE HYPO | KEEP BOTH |
| | HAS HYPER | SEND SHIELD TO 'REMAINING INSIGHTS' |
| | HAS SEVERE HYPER | SEND SHIELD TO 'REMAINING INSIGHTS' |
| | TIME IN HYPO WORSE | KEEP BOTH |
| | TIME IN HYPER WORSE | SEND SHIELD TO 'REMAINING INSIGHTS' |
| | TIME IN CONTROL BETTER | SEND SHIELD TO 'REMAINING INSIGHTS' |
| | CONTROL IN RANGE ABOVE EIGHTY | SEND SHIELD TO 'REMAINING INSIGHTS' |
| HAS HYPER | HAS HYPO | SEND SPEAR TO 'REMAINING INSIGHTS' |
| | HAS SEVERE HYPO | SEND SPEAR TO 'REMAINING INSIGHTS' |
| | HAS HYPER | KEEP BOTH |
| | HAS SEVERE HYPER | KEEP BOTH |
| | TIME IN HYPO WORSE | SEND SPEAR TO 'REMAINING INSIGHTS' |
| | TIME IN HYPER WORSE | KEEP BOTH |
| | TIME IN CONTROL BETTER | SEND SHIELD TO 'REMAINING INSIGHTS' |
| | CONTROL IN RANGE ABOVE EIGHTY | SEND SHIELD TO 'REMAINING INSIGHTS' |
| HAS SEVERE HYPO | HAS HYPO | SEND SPEAR TO 'REMAINING INSIGHTS' |
| | HAS SEVERE HYPO | SEND SPEAR TO 'REMAINING INSIGHTS' |
| | HAS HYPER | SEND SHIELD TO 'REMAINING INSIGHTS' |
| | HAS SEVERE HYPER | KEEP BOTH |
| | TIME IN HYPO WORSE | KEEP BOTH |
| | TIME IN HYPER WORSE | SEND SPEAR TO 'REMAINING INSIGHTS' |
| | TIME IN CONTROL BETTER | KEEP BOTH |
| | CONTROL IN RANGE ABOVE EIGHTY | SEND SHIELD TO 'REMAINING INSIGHTS' |

| SPEAR | SHIELD | ACTION |
|---|---|---|
| TIME IN HYPO WORSE | HAS HYPO | SEND SHIELD TO REMAINING INSIGHTS' |
| | HAS SEVERE HYPO | KEEP BOTH |
| | HAS HYPER | SEND SHIELD TO REMAINING INSIGHTS' |
| | HAS SEVERE HYPER | SEND SHIELD TO REMAINING INSIGHTS' |
| | TIME IN HYPO WORSE | KEEP BOTH |
| | TIME IN HYPER WORSE | SEND SHIELD TO REMAINING INSIGHTS' |
| | TIME IN CONTROL BETTER | SEND SHIELD TO REMAINING INSIGHTS' |
| | CONTROL IN RANGE ABOVE EIGHTY | SEND SHIELD TO REMAINING INSIGHTS' |
| TIME IN HYPER WORSE | HAS HYPO | SEND SHIELD TO REMAINING INSIGHTS' |
| | HAS SEVERE HYPO | SEND SHIELD TO REMAINING INSIGHTS' |
| | HAS HYPER | KEEP BOTH |
| | HAS SEVERE HYPER | KEEP BOTH |
| | TIME IN HYPO WORSE | SEND SHIELD TO REMAINING INSIGHTS' |
| | TIME IN HYPER WORSE | KEEP BOTH |
| | TIME IN CONTROL BETTER | SEND SHIELD TO REMAINING INSIGHTS' |
| | CONTROL IN RANGE ABOVE EIGHTY | SEND SHIELD TO REMAINING INSIGHTS' |
| TIME IN CONTROL BETTER | HAS HYPO | SEND SHIELD TO REMAINING INSIGHTS' |
| | HAS SEVERE HYPO | SEND SHIELD TO REMAINING INSIGHTS' |
| | HAS HYPER | SEND SHIELD TO REMAINING INSIGHTS' |
| | HAS SEVERE HYPER | SEND SHIELD TO REMAINING INSIGHTS' |
| | TIME IN HYPO WORSE | SEND SHIELD TO REMAINING INSIGHTS' |
| | TIME IN HYPER WORSE | SEND SHIELD TO REMAINING INSIGHTS' |
| | TIME IN CONTROL BETTER | KEEP BOTH |
| | CONTROL IN RANGE ABOVE EIGHTY | KEEP BOTH |
| CONTROL IN RANGE ABOVE EIGHTY | HAS HYPO | SEND SHIELD TO REMAINING INSIGHTS' |
| | HAS SEVERE HYPO | SEND SHIELD TO REMAINING INSIGHTS' |
| | HAS HYPER | SEND SHIELD TO REMAINING INSIGHTS' |
| | HAS SEVERE HYPER | SEND SHIELD TO REMAINING INSIGHTS' |
| | TIME IN HYPO WORSE | SEND SHIELD TO REMAINING INSIGHTS' |
| | TIME IN HYPER WORSE | SEND SHIELD TO REMAINING INSIGHTS' |
| | TIME IN CONTROL BETTER | KEEP BOTH |
| | CONTROL IN RANGE ABOVE EIGHTY | KEEP BOTH |

| SPEAR | DELIVERED | ACTION |
|---|---|---|
| HAS HYPO | HAS HYPO | SEND SPEAR TO THE NEXT LAYER |
| | HAS SEVERE HYPO | SEND SPEAR TO THE NEXT LAYER |
| | HAS HYPER | SEND SPEAR TO 'REMAINING INSIGHTS' |
| | HAS SEVERE HYPER | SEND SPEAR TO 'REMAINING INSIGHTS' |
| | TIME IN HYPO WORSE | KEEP SPEAR TO THE NEXT LAYER |
| | TIME IN HYPER WORSE | SEND SPEAR TO 'REMAINING INSIGHTS' |
| | TIME IN CONTROL BETTER | SEND SPEAR TO 'REMAINING INSIGHTS' |
| | CONTROL IN RANGE ABOVE EIGHTY | SEND SPEAR TO 'REMAINING INSIGHTS' |
| HAS SEVERE HYPO | HAS HYPO | SEND SPEAR TO THE NEXT LAYER |
| | HAS SEVERE HYPO | SEND SPEAR TO THE NEXT LAYER |
| | HAS HYPER | SEND SPEAR TO 'REMAINING INSIGHTS' |
| | HAS SEVERE HYPER | SEND SPEAR TO 'REMAINING INSIGHTS' |
| | TIME IN HYPO WORSE | SEND SPEAR TO THE NEXT LAYER |
| | TIME IN HYPER WORSE | SEND SPEAR TO 'REMAINING INSIGHTS' |
| | TIME IN CONTROL BETTER | SEND SPEAR TO 'REMAINING INSIGHTS' |
| | CONTROL IN RANGE ABOVE EIGHTY | SEND SPEAR TO 'REMAINING INSIGHTS' |
| HAS HYPER | HAS HYPO | SEND SPEAR TO 'REMAINING INSIGHTS' |
| | HAS SEVERE HYPO | SEND SPEAR TO 'REMAINING INSIGHTS' |
| | HAS HYPER | SEND SPEAR TO THE NEXT LAYER |
| | HAS SEVERE HYPER | SEND SPEAR TO THE NEXT LAYER |
| | TIME IN HYPO WORSE | SEND SPEAR TO 'REMAINING INSIGHTS' |

| SPEAR | DELIVERED | ACTION |
|---|---|---|
| | TIME IN HYPER WORSE | SEND SPEAR TO THE NEXT LAYER |
| | TIME IN CONTROL BETTER | SEND SPEAR TO 'REMAINING INSIGHTS' |
| | CONTROL IN RANGE ABOVE EIGHTY | SEND SPEAR TO 'REMAINING INSIGHTS' |
| HAS SEVERE HYPER | HAS HYPO | SEND SPEAR TO 'REMAINING INSIGHTS' |
| | HAS SEVERE HYPO | SEND SPEAR TO 'REMAINING INSIGHTS' |
| | HAS HYPER | SEND SPEAR TO THE NEXT LAYER |
| | HAS SEVERE HYPER | SEND SPEAR TO THE NEXT LAYER |
| | TIME IN HYPO WORSE | SEND SPEAR TO 'REMAINING INSIGHTS' |
| | TIME IN HYPER WORSE | SEND SPEAR TO THE NEXT LAYER |
| | TIME IN CONTROL BETTER | SEND SPEAR TO 'REMAINING INSIGHTS' |
| | CONTROL IN RANGE ABOVE EIGHTY | SEND SPEAR TO 'REMAINING INSIGHTS' |
| TIME IN HYPO WORSE | HAS HYPO | SEND SPEAR TO 'REMAINING INSIGHTS' |
| | HAS SEVERE HYPO | SEND SPEAR TO THE NEXT LAYER |
| | HAS HYPER | SEND SPEAR TO 'REMAINING INSIGHTS' |
| | HAS SEVERE HYPER | SEND SPEAR TO 'REMAINING INSIGHTS' |
| | TIME IN HYPO WORSE | SEND SPEAR TO THE NEXT LAYER |
| | TIME IN HYPER WORSE | SEND SPEAR TO 'REMAINING INSIGHTS' |
| | TIME IN CONTROL BETTER | SEND SPEAR TO 'REMAINING INSIGHTS' |
| | CONTROL IN RANGE ABOVE EIGHTY | SEND SPEAR TO 'REMAINING INSIGHTS' |
| TIME IN HYPER WORSE | HAS HYPO | SEND SPEAR TO 'REMAINING INSIGHTS' |
| | HAS SEVERE HYPO | SEND SPEAR TO 'REMAINING INSIGHTS' |
| 662 | HAS HYPER | SEND SPEAR TO THE NEXT LAYER |
| | HAS SEVERE HYPER | SEND SPEAR TO THE NEXT LAYER |
| | TIME IN HYPO WORSE | SEND SPEAR TO 'REMAINING INSIGHTS' |
| | TIME IN HYPER WORSE | SEND SPEAR TO THE NEXT LAYER |
| | TIME IN CONTROL BETTER | SEND SPEAR TO 'REMAINING INSIGHTS' |
| | CONTROL IN RANGE ABOVE EIGHTY | SEND SPEAR TO 'REMAINING INSIGHTS' |
| TIME IN CONTROL BETTER | HAS HYPO | SEND SPEAR TO 'REMAINING INSIGHTS' |
| | HAS SEVERE HYPO | SEND SPEAR TO 'REMAINING INSIGHTS' |
| | HAS HYPER | SEND SPEAR TO 'REMAINING INSIGHTS' |
| | HAS SEVERE HYPER | SEND SPEAR TO 'REMAINING INSIGHTS' |
| | TIME IN HYPO WORSE | SEND SPEAR TO 'REMAINING INSIGHTS' |
| | TIME IN HYPER WORSE | SEND SPEAR TO 'REMAINING INSIGHTS' |
| | TIME IN CONTROL BETTER | SEND SPEAR TO THE NEXT LAYER |
| | CONTROL IN RANGE ABOVE EIGHTY | SEND SPEAR TO THE NEXT LAYER |
| CONTROL IN RANGE ABOVE EIGHTY | HAS HYPO | SEND SPEAR TO 'REMAINING INSIGHTS' |
| | HAS SEVERE HYPO | SEND SPEAR TO 'REMAINING INSIGHTS' |
| | HAS HYPER | SEND SPEAR TO 'REMAINING INSIGHTS' |
| | HAS SEVERE HYPER | SEND SPEAR TO 'REMAINING INSIGHTS' |
| | TIME IN HYPO WORSE | SEND SPEAR TO 'REMAINING INSIGHTS' |
| | TIME IN HYPER WORSE | SEND SPEAR TO 'REMAINING INSIGHTS' |
| | TIME IN CONTROL BETTER | SEND SPEAR TO THE NEXT LAYER |
| | CONTROL IN RANGE ABOVE EIGHTY | SEND SPEAR TO THE NEXT LAYER |

FIG. 14

DATA ANALYTICS AND INSIGHT DELIVERY FOR THE MANAGEMENT AND CONTROL OF DIABETES

CROSS-REFERENCE TO RELATED APPLICATION(S)

This application claims the benefit of U.S. provisional patent application No. 62/208,479, filed Aug. 21, 2015. This application also claims the benefit of U.S. provisional patent application No. 62/266,820, filed Dec. 14, 2015. This application also claims the benefit of U.S. provisional patent application No. 62/286,828, filed Jan. 25, 2016. This application also claims the benefit of U.S. provisional patent application No. 62/304,605, filed Mar. 7, 2016. This application also claims the benefit of U.S. provisional patent application No. 62/304,609, filed Mar. 7, 2016. This application also claims the benefit of U.S. provisional patent application No. 62/304,615, filed Mar. 7, 2016. This application also claims the benefit of U.S. provisional patent application No. 62/304,618 filed Mar. 7, 2016. This application also claims the benefit of U.S. provisional patent application No. 62/329,021, filed Apr. 28, 2016.

TECHNICAL FIELD

Embodiments of the subject matter described herein relate generally to systems and methods for diabetes therapy management. More particularly, embodiments of the described subject matter relate to the generation, management, and delivery of insight messages and glucose management recommendations to mobile devices and other electronic devices owned or operated by patients.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics are advised to routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level. A patient can monitor BG levels using a BG meter or measurement device and by using a continuous glucose sensor if so desired.

In practice, many processes and behaviors result in fluctuations in BG levels. Commonly recognized processes and factors impacting BG levels include food, exercise, disease (acute or chronic), medication (insulin, oral, etc.), and stress and sleep patterns, among others. Furthermore, behavioral and environmental factors such as the time of the day, attentiveness to therapy, and insulin pump maintenance, can provide additional quantitative indications of the underlying factors impacting glucose control. Current reporting tools available to diabetes patients and their caregivers do not provide correlative analyses that can pinpoint specific and personalized behaviors that are associated with a patient's particular glycemic outcomes. Moreover, current reporting mechanisms do not deliver the relevant analyses intelligently at a time most suitable for the users' maximal awareness.

Accordingly, it is desirable to have a system and related methodologies that support enhanced and more intelligent reporting to diabetes patients using an insulin infusion system. In addition, it is desirable to have a mobile application platform that facilitates the delivery of intelligent messages and notifications to diabetes patients. Furthermore, other desirable features and characteristics will become apparent from the subsequent detailed description and the appended claims, taken in conjunction with the accompanying drawings and the foregoing technical field and background.

BRIEF SUMMARY

In accordance with certain embodiments, a personalized diabetes management assistant system utilizes information from various sources to identify and correlate associations to typical glycemic outcomes (hypoglycemia, hyperglycemia, glucose fluctuations). The system can be implemented on various computing platforms (computers, smartphones, tablets, mobile devices, and diabetes management devices such as an insulin infusion device, a continuous glucose sensor device, a continuous glucose monitoring system, or the like) to identify correlations between patient behavior patterns and glycemic outcomes based on retrospective data. Embodiments of the system described herein can prevent or reduce unnecessary user interaction and input, and supplement predictive analytics of glucose trends based on real time data.

A method of managing use of a diabetes management device is disclosed here. An embodiment of the method obtains input data for a user of the diabetes management device, and compares the input data against historical event/outcome combinations maintained for the user. Each of the event/outcome combinations includes insight event data indicative of a glycemic event and a glycemic outcome corresponding to the insight event data. The method continues by determining, based on the comparing, a correlation between the input data and a glycemic outcome. In response to the determining, the method generates a glycemic insight message for delivery to the user. The glycemic insight message includes information regarding a relationship between at least some of the input data and the glycemic outcome.

A computer-implemented glycemic insights system is also disclosed here. An embodiment of the system includes at least one processor device and a non-transitory processor-readable medium operatively associated with the at least one processor device. The processor-readable medium stores executable instructions that are configurable to cause the at least one processor device to perform a method that obtains input data for a user of a diabetes management device, and compares the input data against historical event/outcome combinations maintained for the user. Each of the event/outcome combinations includes insight event data indicative of a glycemic event and a glycemic outcome corresponding to the insight event data. The method determines, based on the comparing, a correlation between the input data and a particular glycemic outcome. In response to the determining, the method generates a glycemic insight message for delivery to the user. The glycemic insight message includes information regarding a relationship between at least some of the input data and the glycemic outcome.

A computer-implemented glycemic insights system is also disclosed here. An embodiment of the system includes a database system to store and maintain historical event/outcome combinations for a user of a diabetes management device, each of the event/outcome combinations including insight event data indicative of a glycemic event and a glycemic outcome corresponding to the insight event data. The system also includes a processor-based insight generation engine to obtain input data for the user, compare the obtained input data against historical event/outcome combinations maintained by the database system for the user, determine a correlation between the obtained input data and a glycemic outcome, and generate a glycemic insight message. The glycemic insight message includes information regarding a relationship between at least some of the obtained input data and the glycemic outcome. The system also includes a processor-based insight delivery engine to regulate and schedule delivery of the generated glycemic insight message to a user device operated by the user.

Another method of managing use of a diabetes management device is also disclosed here. An embodiment of the method obtains a number of glycemic insight messages for delivery to a user device associated with a user of the diabetes management device, each of the glycemic insight messages conveying information regarding a relationship between an insight event derived from patient-specific historical input data and a glycemic outcome. The method continues by culling and prioritizing the number of glycemic insight messages to identify a group of insight messages intended for delivery, queuing the group of insight messages based on the culling and prioritizing, and communicating at least one of the queued insight messages to the user device.

Another computer-implemented glycemic insights system is also disclosed here. An embodiment of the system includes at least one processor device and a non-transitory processor-readable medium operatively associated with the at least one processor device. The processor-readable medium stores executable instructions that are configurable to cause the at least one processor device to perform a method that obtains a number of glycemic insight messages for delivery to a user device associated with a user of a diabetes management device, each of the glycemic insight messages conveying information regarding a relationship between an insight event derived from patient-specific historical input data and a glycemic outcome. The method continues by culling and prioritizing the number of glycemic insight messages to identify a group of insight messages intended for delivery, queuing the group of insight messages based on the culling and prioritizing, and communicating at least one of the queued insight messages to the user device.

Another computer-implemented glycemic insights system is also disclosed here. An embodiment of the system includes a database system to store and maintain historical event/outcome combinations for a user of a diabetes management device. Each of the event/outcome combinations includes insight event data indicative of a glycemic event and a glycemic outcome corresponding to the insight event data. The system also includes a processor-based insight generation engine to generate glycemic insight messages for delivery to a user device associated with the user, each of the glycemic insight messages conveying information regarding a relationship between an insight event derived from patient-specific historical input data and a glycemic outcome. A processor-based insight delivery engine is used to cull and prioritize a number of generated glycemic insight messages to identify a group of insight messages intended for delivery, queue the group of insight messages based on the culling and prioritizing, and deliver at least one of the queued insight messages to the user device.

A method of reporting glucose information for a user of a diabetes management device is also disclosed here. An embodiment of the method obtains input data for the user of the diabetes management device, identifies a glycemic response event based on an analysis of the obtained input data, generates a graphical representation of a glucose response to the glycemic response event, and delivers the generated graphical representation of the glucose response to a user device operated by the user.

A computer-implemented glucose reporting system is also disclosed here. An embodiment of the reporting system includes at least one processor device and a non-transitory processor-readable medium operatively associated with the at least one processor device. The processor-readable medium stores executable instructions that are configurable to cause the at least one processor device to perform a method that obtains input data for a user of a diabetes management device, identifies a glycemic response event based on an analysis of the obtained input data, generates a graphical representation of a glucose response to the glycemic response event, and delivers the generated graphical representation of the glucose response to a user device operated by the user.

Another method of reporting glucose information for a user of a diabetes management device is also disclosed here. An embodiment of the method obtains input data for the user of the diabetes management device, identifies a glycemic response event, and calculates one or more recommended glycemic control parameters based on an analysis of the obtained input data. The one or more glycemic control parameters are calculated to extend a time period during which the user remains within a target glucose range following the glycemic response event. The method continues by generating an output message that includes at least some of the recommended glycemic control parameters, and delivering the generated output message to a user device operated by the user of the diabetes management device.

Another computer-implemented glucose reporting system is also disclosed here. An embodiment of the system includes at least one processor device and a non-transitory processor-readable medium operatively associated with the at least one processor device. The processor-readable medium stores executable instructions that are configurable to cause the at least one processor device to perform a method that obtains input data for a user of a diabetes management device, identifies a glycemic response event, and calculates one or more recommended glycemic control parameters based on an analysis of the obtained input data. The one or more glycemic control parameters are calculated to extend a time period during which the user remains within a target glucose range following the glycemic response event. The method continues by generating an output message that includes at least some of the recommended glycemic control parameters, and delivering the generated output message to a user device operated by the user of the diabetes management device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 11 is part one of an exemplary lookup table suitable for use in resolving internal conflicting glycemic outcomes FIG. 12 is part two of the exemplary lookup table depicted in FIG. 11;

FIG. 13 is part one of an exemplary lookup table suitable for use in resolving external conflicting glycemic outcomes;

FIG. 14 is part two of the exemplary lookup table depicted in FIG. 13;

DETAILED DESCRIPTION

Figure 1:
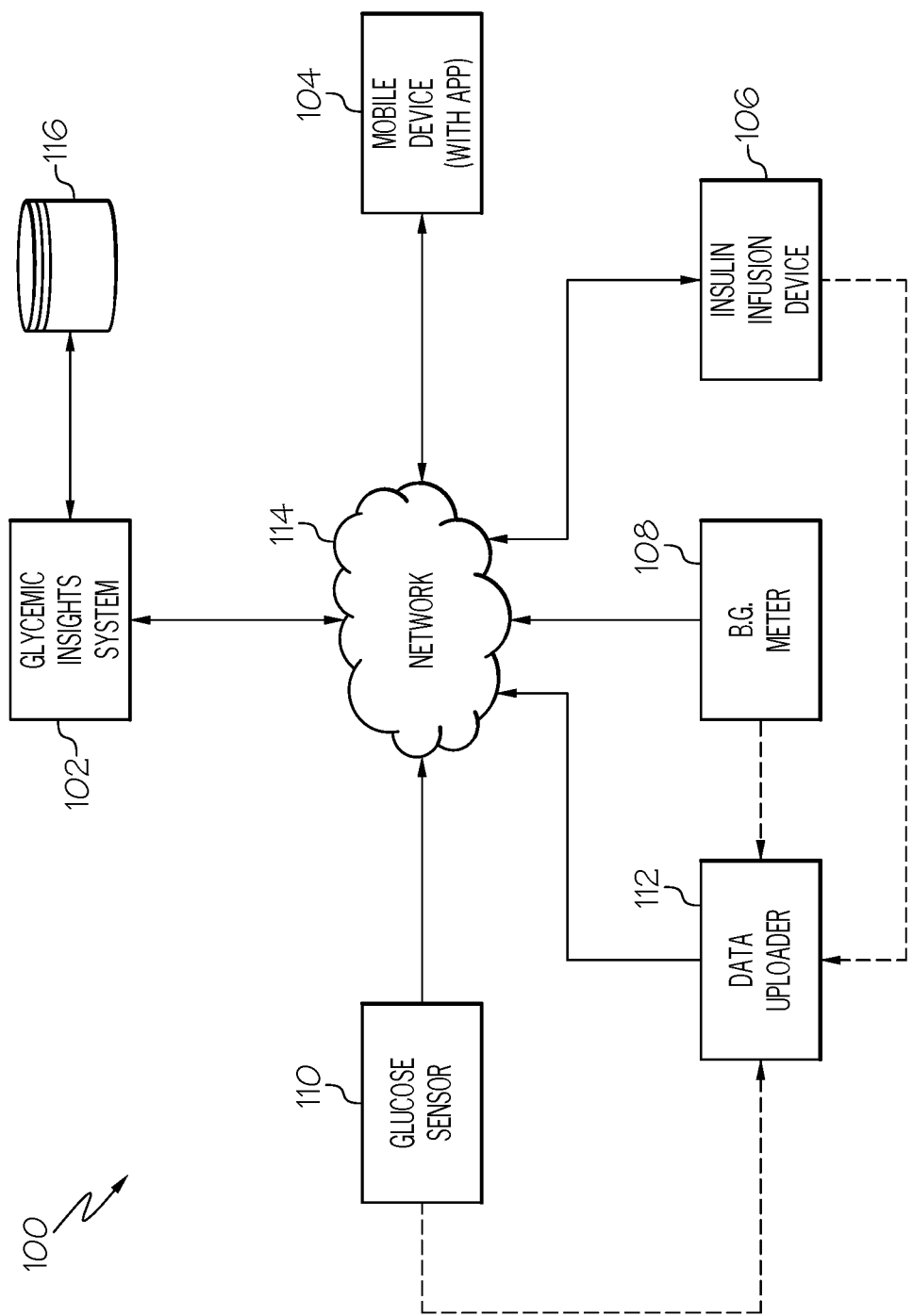
FIG. 1 is a simplified block diagram representation of an exemplary embodiment of a glycemic insights delivery system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or processor-readable instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

The following description relates to a diabetes patient support system that generates and delivers insight messages to patients. The exemplary embodiment disclosed herein is a cloud-based architecture in that most of the processor-intensive tasks are performed by one or more server systems that communicate with remote mobile client devices (e.g., smartphones), portable insulin infusion devices, sources of data, and possibly other remote devices. The disclosed system obtains and processes patient-specific data from various sources, including insulin infusion devices, continuous glucose sensor devices, and mobile client devices. The patient-specific data is processed and analyzed to generate glycemic insights and glucose management recommendations that can help patients manage their diabetes therapy.

For the sake of brevity, conventional features and functionality related to infusion systems, insulin pumps, infusion sets, and fluid reservoirs may not be described in detail here. Examples of infusion pumps and/or related pump drive systems used to administer insulin and other medications may be of the type described in, but not limited to, U.S. Pat. Nos. 5,505,709; 6,485,465; 6,554,798; 6,558,351; 6,659,980; 6,752,787; 6,817,990; 6,932,584; and 7,621,893; which are herein incorporated by reference.

As used herein, an "outcome" is a patient-related result having some correlation to an insight event. For the exemplary embodiment described herein, a "glycemic outcome" is a patient-related result that is associated with the patient's glycemic state, diabetes therapy, insulin status, condition of the insulin infusion device, or the like. More specifically, a glycemic outcome can correspond to a status of blood sugar levels, such as high, low, variable, in range, etc. The glycemic insights delivery system described herein considers a predetermined number of glycemic outcomes, and maps insight events to the glycemic outcomes.

As used herein, a "glycemic insight" is a statistically derived association between an action/event (or a collection of actions/events) and a corresponding outcome as measured by glucose readings.

As used herein, a "glycemic insight message" is any notification, a display, an interactive GUI, a graphical report, or other suitably formatted item that can be communicated to a patient, and that conveys information associated with a glycemic insight. A glycemic insight message conveys the content of at least one glycemic insight in a manner that can be understood and interpreted by the patient. For example, a glycemic insight message will include at least some information related to a triggering glycemic event, along with some information related to the cause and the outcome surrounding the event.

As used herein, an "event feature" is any notable occurrence that can reasonably be detected from available data sources that may have an influence on or be affiliated with resulting glucose levels. Stated another way, an "event feature" is a characteristic or attribute of a notable occurrence that may influence or be affiliated with a glucose outcome.

As used herein, an "insight event" can be a single event feature or a combination of multiple event features. At any particular time, the glycemic insights delivery system described herein considers a predetermined set or universe of insight events of interest. For example, the set of insight events can be selected in a way that focuses on realistic, clinically feasible, or relevant glycemic events that have some relationship to patient outcomes. Thus, the system need not consider or analyze all of the event features and all possible combinations of event features.

As used herein, an "event/outcome combination" refers to an association between one insight event and one outcome. An event/outcome combination may include or be associated with: insight event data indicative of a glycemic event; and a glycemic outcome corresponding to the insight event data.

As used herein, a "trigger" refers to an insight event, a detectable status or condition, or a combination thereof that initiates an action. In this regard, a trigger can initiate the generation of a glycemic insight message, initiate the processing of generated insight messages for delivery, initiate the actual delivery of a particular insight message, or the like.

System Overview

Turning now to the drawings, FIG. 1 is a simplified block diagram representation of an exemplary embodiment of a glycemic insights delivery system 100 that is suitably configured to support the techniques and methodologies described in more detail below. The system 100 supports users of insulin infusion devices, and performs various techniques and methods to help users (patients, caregivers, healthcare providers, parents, etc.) manage the use of insulin infusion devices. It should be appreciated that FIG. 1 depicts one possible implementation of a glycemic insights delivery system, and that other arrangements, architectures, and deployments can be provided if so desired. The system 100 (which has been simplified for purposes of illustration) generally includes or cooperates with the following components, without limitation: a cloud-based glycemic insights system 102; a mobile device 104; an insulin infusion device 106; a blood glucose meter 108; and a continuous glucose sensor 110. The mobile device 104 is a client device that is owned or operated by the user, i.e., a diabetic patient. The insulin infusion device 106, the blood glucose meter 108, and the glucose sensor 110 are components of an insulin infusion system that is used by the patient to treat diabetes. The system 100 may also include or cooperate with an optional data uploader component 112. It should be appreciated that the insulin infusion device 106 can be an optional component in some applications (for example, for Type 2 diabetes patients). For such applications, another diabetes management device and/or the mobile device 104 can function in an equivalent manner to support the system 100.

The glycemic insights system 102 and the mobile device 104 are communicatively coupled to a network 114. In certain embodiments, the insulin infusion device 106, the blood glucose meter 108, and/or the continuous glucose sensor 110 are also communicatively coupled to the network 114 to facilitate the uploading of relevant data to the glycemic insights system 102. Alternatively, or additionally, the insulin infusion device 106, the blood glucose meter 108, and the continuous glucose sensor 110 provide relevant data to the data uploader component 112, which in turn uploads the data to the glycemic insights system 102 via the network 114.

FIG. 1 depicts the network 114 in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network 114 can include or cooperate with any of the following, without limitation: a local area network; a wide area network; the Internet; a personal area network; a cellular communication network; a satellite communication network; a video services or television broadcasting network; a network onboard a vehicle; or the like. The components of the system may be suitably configured to support a variety of wireless and wired data communication protocols, technologies, and techniques as needed for compatibility with the network 114.

In accordance with certain exemplary embodiments, the glycemic insights system 102 is implemented as at least one computer-based or processor-based component. For simplicity and ease of illustration, FIG. 1 depicts the glycemic insights system 102 as a single block—it should be appreciated that any number of distinct hardware components can be utilized to implement the glycemic insights system 102. An exemplary embodiment of a device suitable for implementing the glycemic insights system 102 is described below with reference to FIG. 2.

The glycemic insights system 102 can be considered the "heart" of the glycemic insights delivery system 100. The glycemic insights system 102 includes or cooperates with a database system 116 (which is realized using one or more components) that supports the functionality and operation of the glycemic insights delivery system 100. The glycemic insights system 102 collects and analyzes input data for each patient (the input data can originate from various sources, including an insulin infusion device and/or a source other than the insulin infusion device, such as: a glucose sensor or meter, a mobile device operated by a user of the insulin infusion device, a computing device, etc.), generates relevant and timely glycemic insights as needed, and manages the delivery of the generated glycemic insights to the patients. The glycemic insights system 102 and the related database system 116 are described in more detail below.

In certain embodiments, some or all of the functionality and processing intelligence of the glycemic insights system 102 can reside at the mobile device 104. In other words, the glycemic insights delivery system 100 need not rely on a network-based or a cloud-based server arrangement, although such a deployment might be the most efficient and economical implementation. In other embodiments, some or all of the functionality and processing intelligence of the glycemic insights system 102 can reside at the insulin infusion device 106 and/or at other components or computing devices that are compatible with the system 100. These and other alternative arrangements are contemplated by this disclosure. To this end, some embodiments of the system 100 may include additional devices and components that serve as data sources, data processing units, and/or glycemic insight delivery mechanisms. For example, the system 100 may include any or all of the following elements, without limitation: computer devices or systems; patient monitors; healthcare provider systems; data communication devices; and the like.

The mobile device 104 can be realized using a variety of different device platforms. For example, the mobile device 104 can be implemented as any of the following, without limitation: a cellular telephone or smartphone; a portable computer (e.g., a laptop, a tablet, or a netbook computer); a portable media player; a portable video game device; a portable medical device; a navigation device such as a global positioning system (GPS) device; a wearable computing device; an electronic toy or game; etc. In accordance with certain exemplary embodiments, each mobile device 104 supported by the system 100 is implemented as a computer-based or processor-based component. For simplicity and ease of illustration, FIG. 1 depicts only one mobile device 104. In practice, however, the system 100 is suitably configured to support a plurality of mobile devices 104, wherein each patient or user owns or operates at least one of the supported mobile devices 104. An exemplary embodiment of a device suitable for implementing the mobile device 104 is described below with reference to FIG. 2.

The remainder of this description assumes that the mobile device 104 is a smartphone used by the particular patient. To this end, the configuration and general functionality of the mobile device 104 can be substantially consistent with conventional smartphone design. In this regard, a suitably designed "glycemic insights" mobile app is installed on the mobile device 104 to allow the patient to receive, view, and interact with insight messages and notifications provided by the glycemic insights system 102. The mobile app installed on the mobile device 104 can also be utilized to provide relevant data to the glycemic insights system 102 for storage and analysis. For example, the mobile app can manage and upload the following information, without limitation: calendar data (time of day, day of the week, month, season, etc.); user profile data; GPS data that indicates the geographic position of the mobile device 104; map or navigation data associated with operation of the mobile device 104; user-entered meal consumption, food content, and/or food ingredient data; user-entered carbohydrate data; user-entered exercise related data; user-entered medication related data; user response data associated with the receipt of glycemic insight messages; user feedback related to glycemic insight messages; accelerometer data; contacts list information; web browser data; consumer purchasing data; and the like.

In certain embodiments, the insulin infusion device 106 is a portable patient-worn or patient-carried component that is operated to deliver insulin into the body of the patient via, for example, an infusion set. In accordance with certain exemplary embodiments, each insulin infusion device 106 supported by the system 100 is implemented as a computer-based or processor-based component. For simplicity and ease of illustration, FIG. 1 depicts only one insulin infusion device 106. In practice, however, the system 100 is suitably configured to support a plurality of insulin infusion device 106, wherein each patient or user owns or operates at least one of the insulin infusion devices 106. An exemplary embodiment of a device suitable for implementing the insulin infusion device 106 is described below with reference to FIG. 2.

The system 100 obtains input data from one or more sources, which may include various diabetes management devices (an insulin infusion device, a continuous glucose monitoring device, a glucose sensor, a monitor device, or the like). In this regard, the insulin infusion device 106 represents a source of input data for the system 100. In certain embodiments, the insulin infusion device 106 provides data that is associated with its operation, status, insulin delivery events, and the like. As mentioned previously, relevant data generated or collected by the insulin infusion device 106 can be transmitted directly to the glycemic insights system 102 or indirectly by way of the data uploader component 112, depending on the particular implementation of the system 100. The particular type of data provided by the insulin infusion device 106 is described in more detail below.

For the sake of simplicity, FIG. 1 depicts only one blood glucose meter 108. In practice, however, the system 100 is suitably configured to support a plurality of blood glucose meters 108, wherein each patient or user owns or operates at least one of the blood glucose meters 108. The blood glucose meter 108 is configured to measure the blood glucose level of a user by analyzing a blood sample. For example, the blood glucose meter 108 may include a receptacle for receiving a blood sample test strip. In this regard, the user inserts a test strip into the blood glucose meter 108, which analyzes the sample and displays a blood glucose level corresponding to the test strip sample. The blood glucose meter 108 may be configured to communicate the measured blood glucose level to the insulin infusion device 106 for storage and processing, directly to the glycemic insights system 102, or to the data uploader component 112. In some scenarios, the patient is responsible for entering each blood glucose measurement into the insulin infusion device 106. Ultimately, the measured blood glucose data is provided to the glycemic insights system 102 for analysis.

For the sake of simplicity, FIG. 1 depicts only one glucose sensor 110. In practice, however, the system 100 is suitably configured to support a plurality of glucose sensors 110, wherein each patient or user owns or operates at least one of the glucose sensors 110. The glucose sensor 110 is suitably configured to measure a glucose level (interstitial) of the patient in real time. The glucose sensor 110 may include a wireless transmitter that facilitates transmission of the sensor glucose data to other devices, such as the insulin infusion device 106 or the data uploader component 112. In some implementations, the glucose sensor 110 can provide the sensor glucose data directly to the glycemic insights system 102. Ultimately, the sensor glucose data is received by the glycemic insights system 102 for processing.

Depending on the particular embodiment and application, the system 100 can include or cooperate with other devices, systems, and sources of input data. For example, in certain embodiments the system 100 includes one or more sources of contextual information or data, which may include, without limitation: activity tracker devices; meal logging devices or apps; mood tracking devices or apps; and the like.

Figure 2:
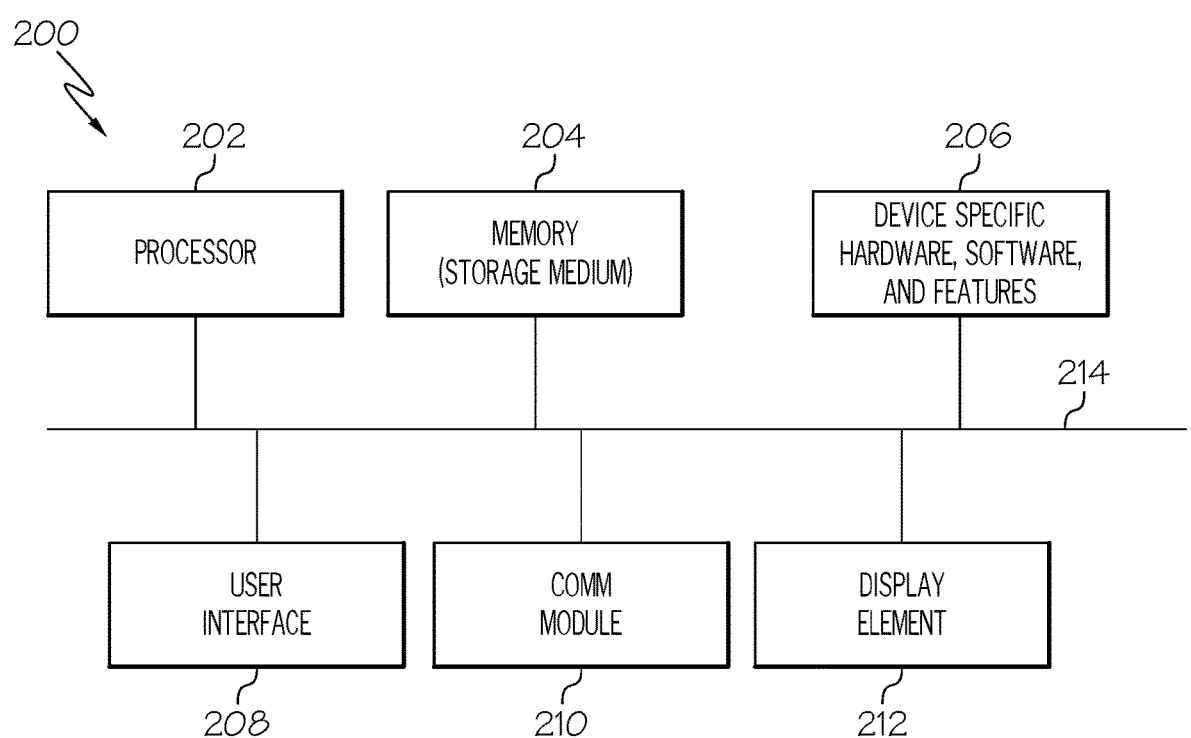
FIG. 2 is a simplified block diagram representation of an exemplary embodiment of a computer-based or processor-based device suitable for deployment in the system shown in FIG. 1.

As mentioned above, the glycemic insights delivery system 100 includes or cooperates with computer-based and/or processor-based components having suitably configured hardware and software written to perform the functions and methods needed to support the features described herein. For example, the glycemic insights system 102, each mobile device 104, and each insulin infusion device 106 can be realized as an electronic processor-based component. Moreover, each blood glucose meter 108 and each data uploader component 112 can also be realized as a processor-based component. In this regard, FIG. 2 is a simplified block diagram representation of an exemplary embodiment of a computer-based or processor-based device 200 that is suitable for deployment in the system shown in FIG. 1.

The illustrated embodiment of the device 200 is intended to be a high-level and generic representation of one suitable platform. In this regard, any of the computer-based or processor-based components of the system 100 can utilize the architecture of the device 200. The illustrated embodiment of the device 200 generally includes, without limitation: at least one processor 202; a suitable amount of memory 204; device-specific hardware, software, firmware, and/or features 206; a user interface 208; a communication module 210; and a display element 212. Of course, an implementation of the device 200 may include additional elements, components, modules, and functionality configured to support various features that are unrelated to the subject matter described here. For example, the device 200 may include certain features and elements to support conventional functions that might be related to the particular implementation and deployment of the device 200. In practice, the elements of the device 200 may be coupled together via a bus or any suitable interconnection architecture 214.

The processor 202 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as RAM memory, flash memory, EPROM memory, EEPROM memory, registers, a hard disk, a removable disk, a CD-ROM, or any other form of storage medium known in the art. In this regard, the memory 204 can be coupled to the processor 202 such that the processor 202 can read information from, and write information to, the memory 204. In the alternative, the memory 204 may be integral to the processor 202. As an example, the processor 202 and the memory 204 may reside in an ASIC. At least a portion of the memory 204 can be realized as a computer storage medium, e.g., a tangible computer-readable medium having computer-executable instructions stored thereon. The computer-executable instructions, when read and executed by the processor 202, cause the device 200 to perform certain tasks, operations, functions, and processes that are specific to the particular embodiment. In this regard, the memory 204 may represent one suitable implementation of such computer-readable media. Alternatively or additionally, the device 200 could receive and cooperate with computer-readable media (not separately shown) that is realized as a portable or mobile component or platform, e.g., a portable hard drive, a USB flash drive, an optical disc, or the like.

The device-specific hardware, software, firmware, and features 206 may vary from one embodiment of the device 200 to another. For example, the device-specific hardware, software, firmware, and features 206 will support: smartphone functions and features when the device 200 is realized as a mobile telephone; conventional personal computer functions and features if the device 200 is realized as a laptop or tablet computer; insulin pump operations when the device 200 is realized as an insulin infusion device; etc. In practice, certain portions or aspects of the device-specific hardware, software, firmware, and features 206 may be implemented in one or more of the other blocks depicted in FIG. 2.

The user interface 208 may include or cooperate with various features to allow a user to interact with the device 200. Accordingly, the user interface 208 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The user interface 208 may include one or more graphical user interface (GUI) control elements that enable a user to manipulate or otherwise interact with an application via the display element 212.

The communication module 210 facilitates data communication between the device 200 and other components as needed during the operation of the device 200. In the context of this description, the communication module 210 can be employed to transmit or stream device-related control data, patient-related data, device-related status or operational data, glycemic insight messages and notifications, and the like. It should be appreciated that the particular configuration and functionality of the communication module 210 can vary depending on the hardware platform and specific implementation of the device 200. Accordingly, with reference to FIG. 1, the communication module of the glycemic insights system 102 is utilized to obtain input data from various sources, and to send glycemic insight messages and notifications to the mobile device 104. Moreover, the communication module of the insulin infusion device 106 can be used to receive sensor glucose data from the glucose sensor 110, and to send input data to the glycemic insights system 102. In practice, an embodiment of the device 200 may support wireless data communication and/or wired data communication, using various data communication protocols. For example, the communication module 210 could support one or more wireless data communication protocols, techniques, or methodologies, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 210 could support one or more wired/cabled data communication protocols, including, without limitation: Ethernet; powerline; home network communication protocols; USB; IEEE 1394 (Firewire); hospital network communication protocols; and proprietary data communication protocols.

The display element 212 is suitably configured to enable the device 200 to render and display various screens, insight messages, notifications, GUIs, GUI control elements, drop down menus, auto-fill fields, text entry fields, message fields, or the like. Of course, the display element 212 may also be utilized for the display of other information during the operation of the device 200, as is well understood. Notably, the specific configuration, operating characteristics, size, resolution, and functionality of the display element 210 can vary depending upon the practical implementation of the device 200. For example, if the device 200 is a laptop computer, then the display element 212 may be a relatively large monitor. Alternatively, if the device 200 is a cellular telephone device, then the display element 212 may be a relatively small integrated display screen, such as a touch-sensitive screen.

Glycemic Insights

The glycemic insights delivery system 100 provides useful information and messages to diabetes patients so that the patients can better understand how certain situations lead to predictable outcomes. Many processes and behaviors result in fluctuations in blood glucose levels. Commonly recognized processes impacting blood glucose levels include food, exercise, disease (acute or chronic), medication (insulin, oral, and other types), stress and sleep patterns, and the like. Furthermore, behavioral factors such as the time of the day, attentiveness to therapy, and the proper use and maintenance of the insulin infusion system can provide additional quantitative indications of the underlying factors impacting glucose control. Current reporting systems and schemes available to diabetes patients and their caregivers do not provide correlative analyses that can pinpoint the specific, personalized behaviors that are associated with a patient's glycemic outcomes. Moreover, current reporting mechanisms do not always provide reports and notifications in accordance with an intelligent delivery timing scheme that attempts to maximize user awareness.

The glycemic insights delivery system 100 represents a personalized diabetes management assistant system that utilizes information and data collected from various sources to identify the associations to typical glycemic outcomes (such as hypoglycemia, hyperglycemia, and control in the range). The system 100 considers combinations or patterns of input data that are based on clinical research, wherein such combinations or patterns are typically correlated to the glycemic outcomes of interest. As explained above with reference to FIG. 1 and FIG. 2, the system 100 can be implemented on various computing platforms (computers, smartphones, tablets, and insulin infusion devices) to identify certain correlations between patient behaviors and glycemic outcomes based on retrospective data. The system 100 can also be utilized to reduce or prevent unnecessary user interaction, and to input and supplement predictive analytics of glucose prediction based on real time data. In an exemplary embodiment, the system 100 employs a cloud-based server architecture and related processing power to generate glycemic insights by identifying trends and associations between glycemic outcomes (both short and long term) and the behavior of the patients. The system 100 is suitably configured and operated to optimize the delivery time of glycemic insight messages to patients, caregivers, and healthcare providers to increase the likelihood that the messages will be opened or read, understood, and acted upon (if needed). In addition to increasing the likelihood of messages being read, the intelligent insight message delivery scheme presented here also strives to time delivery of insight messages at appropriate times, e.g., when an insight message is actionable, to enhance positive results.

In practice, the system 100 requires a minimum amount of input data per patient before it can generate intelligent and accurate glycemic insights. For example, it may be necessary to collect input data for at least one full day. Going forward, however, the glycemic insights generated by the system 100 will progressively become more sophisticated and accurate as more and more input data is collected and analyzed for a given patient. The glycemic outcome assessment techniques and insight generation methodologies described herein assume that the sources of input data (such as glucose sensors, blood glucose meters, physiological sensors, and the like) are operating within an acceptable range of accuracy.

Figure 3:
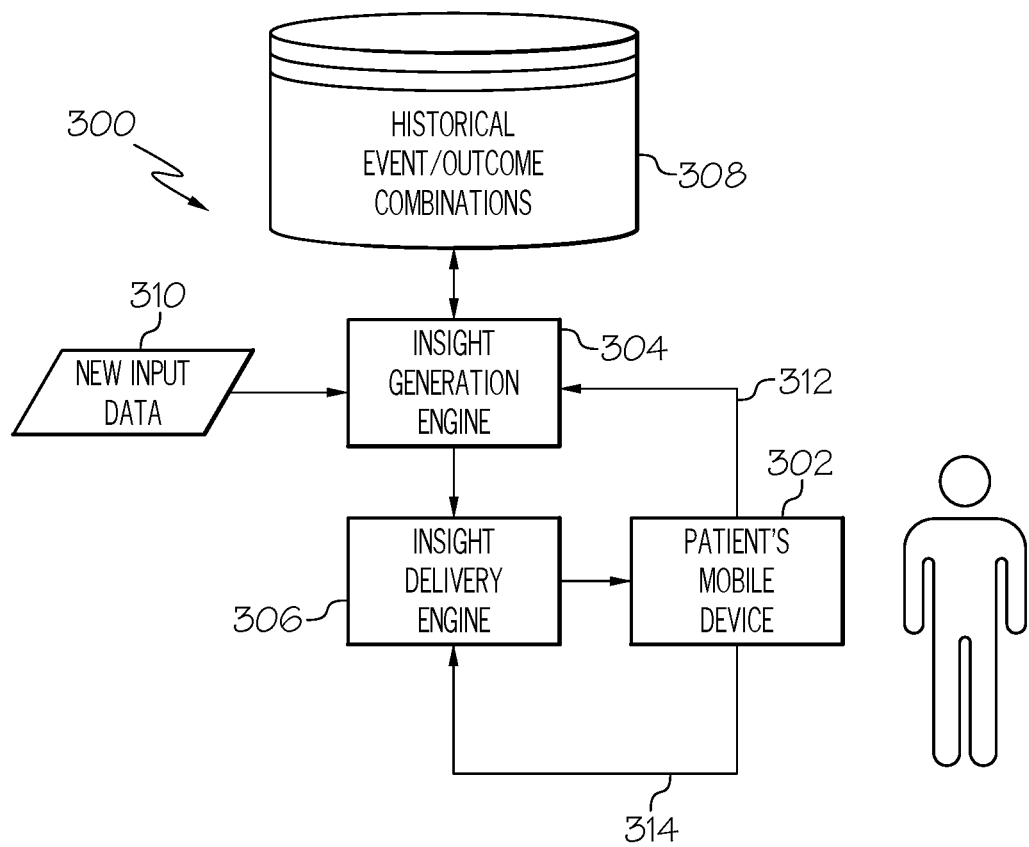
FIG. 3 is a simplified block diagram representation of an exemplary embodiment of a glycemic insights delivery system in cooperation with a patient's mobile device.

FIG. 3 is a simplified block diagram representation of an exemplary embodiment of a glycemic insights delivery system 300 in cooperation with a patient's mobile device 302. Certain aspects of the system 300 are similar to that described above for the system 100 (see FIG. 1), and common features and functions will not be redundantly described here. The embodiment of the system 300 shown in FIG. 3 generally includes, without limitation: an insight generation engine 304; an insight delivery engine 306; and a database system 308 (which may correspond to the database system 116 described above). The insight generation engine 304 and the insight delivery engine 306 are suitably implemented as processor-based functional modules that are designed to perform the various functions and methods described in detail herein. The insight generation engine 304 receives and processes new input data 310 as it becomes available from various data sources. New input data 310 can be filtered or otherwise managed, stored, and maintained in the database system 308 as needed for purposes of ongoing use as historical data in the future. Any amount of the new input data 310 can be compared against historical event/outcome combinations maintained by the database system 308 for purposes of determining whether or not to generate a glycemic insight for the patient.

In certain embodiments, the insight generation engine 304 also obtains some input data in the form of mobile device data 312 from the patient's mobile device 302. The mobile device data 312 can include any type of data or information generated by the mobile device 302, forwarded by the mobile device 302, entered at the mobile device 302, detected by the mobile device 302, or the like. For example, and without limitation, the mobile device data 312 can include time stamp data, calendar data, mobile app data, status information related to the operation of the mobile device 302, and/or sensor data generated by sensors or detectors onboard the mobile device 302 (such as an accelerometer, a gyroscope, a light sensor, a camera, a thermometer, a biometric scanner, etc.). The insight generation engine 304 can forward any or all of the mobile device data 312 to the database system 308 for processing, indexing, and storing as historical data. Moreover, the insight generation engine 304 can use any or all of the mobile device data 312 to determine whether or not to generate a glycemic insight for the patient.

The insight delivery engine 306 handles the scheduling and delivery of generated insights to the patient's mobile device 302 (or to any system, device, or platform that is suitably configured to receive and present generated insights to the patient). Thus, the insight delivery engine 306 cooperates with the insight generation engine 304 to receive, process, and regulate the delivery of glycemic insights. In certain embodiments, the insight delivery engine 306 cooperates with the patient's mobile device 302 to obtain user feedback 314 regarding glycemic insights that have been received at the mobile device 302. The user feedback 314 can be obtained via a suitable mobile app that is loaded on the mobile device 302, wherein the mobile app is utilized to generate and present the glycemic insights to the patient. The mobile device data 312 can also include user feedback information for use by the insight generation engine 304 if so desired. The user feedback 314 is helpful to influence the manner in which generated insights are prioritized and delivered (if at all) going forward, to enhance the patient experience and to increase the value of the insights to each particular patient.

Data Inputs

There are many factors that can influence a patient's blood glucose levels. Various factors may also influence how best to control and manage the patient's blood glucose. The glycemic insights methodology presented here is based on the collection and analysis of data, which need not be specifically related to BG meter measurements, glucose sensor readings, or insulin delivery information. Although the system 100, 300 obtains and analyzes such data, it also obtains and considers additional data, including information collected and provided by the mobile app resident on the patient's mobile device. The system 100, 300 may also process data received directly or indirectly from other physiological sensors, devices, or equipment. For example, an embodiment of the system 100, 300 can be suitably configured to analyze respiratory data, electrocardiogram data, body temperature data, heartrate information, and the like.

The glycemic insights delivery system 100, 300 is suitably configured to receive and process a variety of input data from multiple sources. Moreover, the system 100, 300 is designed to be flexible and scalable to accommodate additional input data types as needed. The number of input data sources and the amount of input data handled by the system 100, 300 may vary from one embodiment to another, depending on the particular implementation and intended application. In accordance with the embodiment described here, some or all of the following input data can be used for purposes of triggering the generation of glycemic insights, prioritizing the delivery of generated glycemic insights, maintaining actionable event/outcome combinations, generating glucose management recommendations, and the like. The following summary of specific input data types is not intended to be exhaustive or otherwise limiting, and alternative or additional input data can be considered in an embodiment of the system 100, 300.

Carbohydrate amount—this refers to the carbohydrate amount that one Unit of insulin can compensate to maintain the current glucose level. The carbohydrate amount is usually expressed in grams or milligrams. The patient's mobile device will usually be the source of this data.

Bolus information—the bolus information includes the bolus dosage amount (in Units of insulin), the date/time of delivery (time of day and calendar data), and the bolus type (normal, square, or dual). The insulin infusion device will usually be the source of this data.

Insulin to carbohydrate ratio—this is a patient-specific parameter that relates to how much insulin the patient needs to compensate for a designated unit (e.g., one gram) of carbohydrate. The insulin to carbohydrate ratio is expressed in grams/Unit. The insulin infusion device will usually be the source of this data.

Insulin sensitivity factor—this is a patient-specific parameter that relates to the reduction in blood glucose in response to one Unit of insulin. The particular manner in which the insulin sensitivity factor is calculated is determined by the specific pumping protocol. The insulin sensitivity factor is expressed in mg/dL/U (milligrams per deciliter per Unit). The insulin infusion device will usually be the source of this data.

Active insulin amount—this refers to how much insulin is still active in the body of the patient from previous bolus doses. This quantity is expressed in Units of insulin. The insulin infusion device will usually be the source of this data.

Time of day—this refers to timestamp and/or date stamp information, which may be associated with or appended to any other piece of input data to provide a time reference.

Basal rate—this is a patient-specific parameter that indicates the basal rate of insulin delivery, which is usually expressed in Units/hour. The insulin infusion device will usually be the source of this data.

Temporary basal use—this refers to an occurrence during which the patient temporarily "overrides" the nominal or usual basal rate of insulin. The system employs a boolean value that indicates the activation of the temporary basal mode, and also indicates the temporary basal rate value. The insulin infusion device will usually be the source of this data.

Consecutive boluses—this refers to an occurrence of back-to-back insulin boluses, which are delivered within a designated period of time. The system employs a boolean value that indicates the occurrence of consecutive boluses, and also indicates the total volume of the boluses delivered during the designated period of time. The insulin infusion device will usually be the source of this data.

Insulin suspension—this refers to a period of time during which the insulin infusion device has been temporarily suspended (insulin delivery is temporarily halted). The data related to insulin suspension can include some or all of the following, without limitation: threshold setting; suspension duration; active insulin before the suspension; sensor rate of change around the suspension; carbohydrate intake around the suspension; time (day of week, time of day) of the suspension; how the suspension recovered; and user response to the suspension. The insulin infusion device will usually be the source of this data.

Reservoir rewind and priming time—this refers to activities associated with the installation of a new insulin reservoir into the insulin infusion device. This requires a rewind action to retract the reservoir actuator, which facilitates removal of the used reservoir. After installing the new reservoir, the fluid flow path is primed for insulin delivery. The insulin infusion device will usually be the source of this data.

Pump alarms and associated alarm times—pump alarms can be generated by the insulin infusion device for various reasons. Pump alarm data indicates the type of alarm and the corresponding alarm time. The insulin infusion device will usually be the source of this data.

Sensor alerts and alert times—sensor alerts can be generated by the insulin infusion device and/or the glucose sensor for various reasons. Sensor alert data indicates the type of sensor alert and the corresponding alert time. The insulin infusion device and/or the glucose sensor can be the source of this data.

Blood glucose readings and measurement times—blood glucose readings are usually expressed in mg/dl, and are obtained from a blood glucose meter. The insulin infusion device, the blood glucose meter, or the patient's mobile device can be the source of this data.

User demographic information—this data may include, without limitation, the patient's age, number of years using insulin, medical diagnosis, age at the onset of diabetes, sex, medication types, and the like. User demographic information can be provided by the patient's mobile device, the insulin infusion device, a webpage user interface, or the like.

Meal time and content—this data relates to the timing of meal consumption and the type and amount of food consumed. The patient's mobile device will usually be the source of this data. In this regard, a suitably configured mobile app can include a feature or functionality that allows the patient to specify meal times and to estimate the type and amount of food consumed at each meal. In certain scenarios, this data can be imported from a third party (partner) database directly, rather than having patients redundantly enter the information into the mobile app.

Exercise time and content—this data relates to the timing of exercise and the type, duration, and amount of exercise performed by the patient. The patient's mobile device will usually be the source of this data. In this regard, a suitably configured mobile app can include a feature or functionality that allows the patient to specify exercise times and to estimate the type and amount of exercise. In certain scenarios, this data can be imported from a third party (partner) database directly, rather than having patients redundantly enter the information into the mobile app.

Medication type, dosage, and time—this data relates to instances when the patient takes medication (other than insulin), and the data indicates the type of medication, the dosage taken, and the time that the medication was taken. The patient's mobile device will usually be the source of this data. In some scenarios, a smart insulin pen or other type of smart insulin delivery device can be the source of this data. In this regard, a suitably configured mobile app can include a feature or functionality that allows the patient to record information associated with taking medication.

Sleep time and quality—this data indicates sleeping periods, and information related to the quality or type of sleep experienced by the patient. The sleep-related information can be provided by a patient monitor or, in certain embodiments, the sleep-related information is provided by a suitably configured mobile app running on the patient's mobile device. In such an embodiment, the mobile app allows the patient to enter the relevant sleep-related information. In accordance with some embodiments, sleep related information can be calculated using accelerometer data, heartrate data, ambient lighting measurements, glucose levels, etc.

Stress time—this data indicates periods of stress experienced by the patient. The stress-related information can be derived from physiological factors and/or measurable data such as heart rate, blood pressure, skin conductance, body temperature, or the like. Additionally or alternatively, the stress-related information can be based on user input. Accordingly, the patient's mobile device can be the source of this data. A suitably configured mobile app can include a feature or functionality that allows the patient to record information associated with periods of stress.

Electronic medical records and lab test data—this data can be provided by healthcare providers, medical facilities, insurance companies, or the like. In certain scenarios, this data can be imported from a third party (partner) database directly, rather than having patients redundantly enter the information into the mobile app.

User reaction to delivered insights—this data represents user feedback, and it may be considered to be a form of input data. The patient's mobile device will usually be the source of this data. In this regard, a suitably configured mobile app can include a feature or functionality that allows the patient to provide user feedback related to glycemic insights delivered to the patient.

User behavior change to delivered insights—this data is associated with actions taken by the patent in response to glycemic insights delivered by the system. User behavior change is measured by the percent of change of the occurrence of those events that were communicated to users as glycemic insights. It indicates whether the insight messages provide any impact on user's behavior and whether the behavior change leads to significant outcome improvement. The data source of the data includes almost all data sources mentioned before Glycemic Outcomes As explained above, the system 100, 300 analyzes collected input data to identify occurrences of insight events and to determine whether or not identified insight events are associated with or otherwise linked to specific glycemic outcomes. The particular glycemic outcomes of interest can vary from one embodiment of the system 100, 300 to another, and perhaps from one patient to another. The exemplary embodiment of the system 100, 300 described herein utilizes ten defined glycemic outcomes. Five of the glycemic outcomes are standalone (or direct) outcomes, and five of the glycemic outcomes are "differential" outcomes. In this context, a direct glycemic outcome relates to a comparison between the patient's current glucose values to a static well-established commonly-used threshold, such as hypoglycemia and hyperglycemia. In this regard, a glycemic outcome can be a simple threshold-based outcome that is binary in nature. In contrast, a differential glycemic outcome is a comparison between a patient's current glucose values to statistics of the patient's own historical glucose values.

The exemplary embodiment of the system 100, 300 employs the five direct glycemic outcomes listed here: (1) Hypoglycemia, based on a specified threshold such as "less than 70 mg/dl"; (2) Severe Hypoglycemia, based on a specified threshold such as "less than 50 mg/dl"; (3) Hyperglycemia, based on a specified threshold such as "greater than 240 mg/dl"; (4) Severe Hyperglycemia, based on a specified threshold such as "greater than 300 mg/dl"; and (5) Good Control. The first four glycemic outcomes listed above are self-explanatory. The "Good Control" outcome indicates that the patient has experienced good glycemic control or management that satisfies certain quantifiable criteria. For example, if the patient's measured or sensed glucose levels were within the target range for more than 20 hours during the last day, then the "Good Control" outcome can be indicated. As another example, if the patient's measured or sensed glucose levels are within the target range for at least 80% of the time during the last week, then the "Good Control" outcome can be indicated.

The exemplary embodiment of the system 100, 300 employs the five differential glycemic outcomes listed here: (1) Percentage of Time: Hypoglycemia; (2) Percentage of Time: Severe Hypoglycemia; (3) Percentage of Time: Hyperglycemia; (4) Percentage of Time: Severe Hyperglycemia; and (5) Percentage of Time: Good Control. Each of the differential glycemic outcomes listed above is associated with a defined window of time, and each outcome represents a calculated percentage against corresponding thresholds based on values within the defined window of time. For example, if the window of time is the period between 8:00 PM and 10:00 PM, and the input data for the patient indicates hyperglycemia for 30 minutes during that window, then the "Percentage of Time: Hyperglycemia" metric will be 25%. In contrast to direct glycemic outcomes (which are binary in nature), each differential glycemic outcome can have a range of possible states or values (i.e., a range of percentages) and thus requires further conversion processing to convert the values into binary states. The conversion process compares the value of the differential glycemic outcome against a statistical measure from the same user's historical values, such as an average, and determines whether the outcome value is higher or lower. The system 100, 300 handles differential glycemic outcomes in this manner to remove potential patient bias, which facilitates a comparison of each insight event against the patient baseline rather than a fixed threshold or fixed criteria. As explained in more detail below, the handling of differential glycemic outcomes is associated with an analysis of the patient's average or typical outcomes, such that glycemic insights are generated when an insight event under investigation is strongly correlated to a differential outcome.

Additional or alternative glycemic outcomes utilized by the system 100, 300 may include any or all of the following, without limitation: glycemic variability during a designated period of time, such as the last hour, the previous day, the last week, or the last month; a variable event with a sensor glucose rate of change greater than a specified threshold; or sensor glucose within a defined range of values within a specified period of time. It should be appreciated that the system 100, 300 can be modified or updated as needed to contemplate different glycemic outcomes that may be of interest.

Data Analysis: Generation of Glycemic Insights

In accordance with certain embodiments of the system 100, 300, glycemic insights are generated at certain times and/or in response to the occurrence of certain insight events, by looking at historical data for associations between specific situations and particular glucose patterns. Thus, glycemic insights may be generated at specified times of the day, on certain days of the week, or the like. Alternatively or additionally, glycemic insights can be generated in response to insight events related to the operation of the insulin infusion device, such as any of the following, without limitation: delivery of a bolus; a specific sensor glucose level; alarms or alerts; or the changing of the infusion set. Historical data maintained by the database system 116, 308 may include glucose information for occurrences of an insight event, such that the system 100, 300 can review the historical data to find "matching" occurrences that correspond to a currently detected insight event occurrence. In practice, the amount of historical data that is considered can be limited or otherwise regulated based on the particular insight event of interest and/or the particular situation being evaluated. For example, very old and dated historical data need not be reviewed under most circumstances. The specific situations and particular glucose patterns evaluated by the system 100, 300 are based on the complete set of input data that is available for analysis. As mentioned above, any combination of one or more event features can be considered for purposes of generating glycemic insights. To this end, the system 100, 300 can leverage any number of machine learning, pattern recognition, or data analytics techniques and methodologies to determine whether there is any statistical correlation between the different situations (insight events) and the evaluated glucose patterns.

In practice, the system 100, 300 contemplates hundreds of different possible patient behavior patterns. The exemplary embodiment described here considers more than 600 different patterns, wherein a pattern can be a combination of lower level patterns, individual event features, or specific insight events (such as eating food, taking a bolus, starting to exercise). As mentioned above, the exemplary embodiment of the system 100, 300 handles ten different outcomes. Thus, the mapping of 600+ patterns to one or more outcomes represents the number of possible glycemic insights that can be produced by the system 100, 300. The system 100, 300 is expandable in that additional event features, "low level" data patterns, or insight events can be introduced as needed.

In certain implementations, the generation of a glycemic insight message can be influenced by any of the following types of insight events, without limitation: insulin related; time related; sensor glucose related; blood glucose related; calibration (of the insulin infusion device) related; alarm related; meal or nutrition related; geography related; calendar related; career, job, or work related; physical exercise related; sleep related; disease or health related; mental state or mood related; or doctor visit related. Of course, other categories and types of insight events can be considered by the system, and various glycemic outcomes can be associated with one or more of the insight events.

Insulin related insight events include, without limitation: bolus type; abnormal change of time intervals between boluses; suspend pump operation; significant change in total daily dose (TDD) based on long term data; abrupt change of basal pattern; substantial change of average basal rate; and change of active insulin delaying curve (derived from rate of change in insulin on board). Time related insight events include, without limitation: time of day; day of week; day of month; holiday, fasting, or festival days; and long time period of time since the last data upload. Sensor glucose related insight events include, without limitation: very good accuracy; high rate of change (ROC); high ROC of ROC; low and high thresholds; response to hyper event; response to hypo event; recent glucose changes; temporary sensor glucose data packets missing; sensor glucose artifacts; and age of glucose sensor (e.g., number of days used). Blood glucose insight events include, without limitation: low and high thresholds; and adherence changes. Calibration related insight events include, without limitation: the amount of time since the last calibration. Alarm related insight events include, without limitation: use of the bolus calculator feature; insulin pump rewind; no insulin delivery; motor error alarm; low/high sensor glucose alerts; sensor start; sensor end; and sensor errors. Meal or nutrition related insight events include, without limitation: specific food and patient response to food (delayed absorption); specific carbohydrate count; missed meals; extra meals; extra food count for one meal; less food count for one meal; snack before bedtime; snack before exercise; snacking in general; and fasting periods (long term missing meal pattern versus short term). Geography related insight events include, without limitation: presence in a certain restaurant; no restaurants located within a defined radius of the user's current position; at home; at work; on vacation; close to a body of water (important if the infusion device is not waterproof); proximity to a hospital, care facility, or pharmacy (access to medical care); socioeconomic status of the location; indication of user habits and hobbies (outdoor activities, etc.); indication of support networks (e.g., frequently visited houses, businesses, or locations); and presence in a gym or exercise facility. Calendar related insight events include, without limitation: movie; flight; meeting; menstrual cycle; and days on medication. Career job, or work related insight events include, without limitation: job type or position; work schedule; and hours worked per week. Physical exercise related insight events include, without limitation: exercise start and end times, which can be automatically detected using electronic fitness measurement devices; abnormal amount of exercise; and unusual exercise timing (missed a normal exercise time, more exercise than usual, etc.). Sleep related insight events include, without limitation: start and end times; and dawn phenomena. Disease or health related insight events include, without limitation: onset of an acute disease or condition, such as a cold, an allergy attack, or the flu; and end of an acute disease or condition. Mental state or mood related insight events include, without limitation: fright; excitement; anger; happiness; depression; despair; hope; sadness; etc. Doctor visit related insight events include, without limitation: recent doctor visit; unusual doctor visit pattern; and increased frequency of doctor visits.

The correlation between patterns and outcomes is patient specific. The system 100, 300 continuously learns and trains itself to generate the patient-specific glycemic insights. In practice, many of the data patterns will rarely (if ever) be detected for a given patient. Nonetheless, the system 100, 300 continues to monitor the input data and check all possible combinations, for safe measure. Note that there could be a scenario where one of the ten outcomes is under consideration, but the system 100, 300 has not yet identified a strong enough correlation to an associated data pattern. Statistically, this scenario will resolve itself over time and the system 100, 300 will detect a correlation between an insight event and that particular outcome if one exists. Conversely, there can be a situation where there isn't a predictable or repeatable data pattern that causes the outcome. In that case, the system 100, 300 will not generate a glycemic insight message.

The glycemic insights can be considered to be the output of the system 100, 300, wherein the output is generated in response to the most current input data and at least some of the historical data maintained at the database system 116, 308. Each glycemic insight message includes information that is easy for the patient to understand. In accordance with certain embodiments, each glycemic insight message provides information to the user regarding at least the following: the trigger(s) to the insight; the factors associated with the glycemic outcome; and historical outcomes. The factors can be filtered according to their importance, as determined through clinical guidance, medical research, or the like.

In accordance with some embodiments, the insight generation engine 304 (see FIG. 3) finds similar insight event instances using an approach that is similar to the "shingling" process that gauges the similarity of two unique "shingles" (contiguous subsequences of tokens in a document). For a given shingle size, the degree to which two events A and B resemble each other can be expressed as the ratio of the magnitudes of their shingling intersection and union:

$$r(A, B) = \frac{|S(A) \cap S(B)|}{|S(A) \cup S(B)|} \quad \text{Eq. 1}$$

where the resemblance (r) is a number in the range of [0 1], where one indicates that the two events are identical.

In accordance with some embodiments, the insight generation engine 304 finds similar insight event instances using a Euclidean distance approach. In this approach, the Euclidean distance is the "ordinary" or "straight-line" distance between two events in Euclidean space. The norm of the n-dimensional Euclidean distance (Equation 2 below) can be used to determine the similarity of two events.

$$d(p, q) = \quad \text{Eq. 2}$$

-continued
$$\sqrt{(p_1 - q_1)^2 + (p_2 - q_2)^2 + \ldots + (p_i - q_i)^2 + \ldots + (p_n - q_n)^2}$$

In accordance with some embodiments, the insight generation engine 304 finds the most influential glycemic insight triggering feature (i.e., a data pattern or an insight event that includes one or more event features) using an approach that is based on machine learning models. In this regard, many predictive models have built-in or intrinsic measurements of predictor importance. For example, multivariate adaptive regression splines (MARS) and many tree-based models monitor the increase in performance that occurs when adding each predictor to the model. Others, such as linear regression or logistic regression can use quantifications based on the model coefficients or statistical measures (such as T-statistics). These and similar techniques can be leveraged by the system 100, 300 if so desired.

In accordance with some embodiments, the insight generation engine 304 finds the most influential glycemic insight triggering feature using feature importance measuring techniques. In this regard, there are many approaches that can be used to quantify each relationship with an outcome, based on a simple correlation statistic such as linear regression. The system 100, 300 can utilize such a technique to roughly estimate the relationship between the input data and glycemic outcomes. For complex relationships where correlation isn't linear, techniques such as a locally weighted regression model can be used. This technique is based on a series of polynomial regressions that model the data in small neighborhoods. The insight generation engine 304 can also utilize an approach that is based on maximal information coefficient or other similar methods. These and similar techniques can be leveraged by the system 100, 300 to generate glycemic insights if so desired.

In accordance with some embodiments, the insight generation engine 304 finds the most influential glycemic insight triggering feature using domain knowledge based association. To this end, some research based knowledge can be used to create static relationships between the input data and the glycemic outcomes, such as lack of sleep and bad glycemic control. This and similar techniques can be leveraged by the system 100, 300 to generate glycemic insights if so desired.

Glycemic insights can be used to describe or identify glycemic management patterns for patients. The information conveyed in a glycemic insight can include any of the following, without limitation: associations between meal bolus amount and type, and post-meal glucose profiles; associations between temporary basal use and post-exercise glucose variability; and associations between insulin pump suspension and rebound hyperglycemia. The concepts described herein can be extended to find correlations and causality between food intake and diabetes management. The concepts can also be used in decision support algorithms for clinicians to understand patient behaviors.

In accordance with certain embodiments, a glycemic insight message includes content from four primary categories: insight events or times; historical data; specific situations; and particular glucose patterns. In this regard, glycemic insights are generated at certain INSIGHT EVENTS OR TIMES by looking at HISTORICAL DATA for associations between SPECIFIC SITUATIONS and PARTICULAR GLUCOSE PATTERNS. The system 100, 300 can utilize a predefined set of selectable message content for one or more of these primary categories if so desired. For example, the system 100, 300 can maintain a list of different insight events or times that are of interest for purposes of triggering the generation of glycemic insights. As another example, the system 100, 300 can maintain a predefined list of particular glucose patterns that are commonly experienced by diabetes patients. As explained above, the exemplary embodiment of the system 100, 300 contemplates ten different glycemic outcomes.

A number of glycemic insight examples are provided below in the context of typical patient scenarios. It should be appreciated that the specific content, wording, formatting, use of graphics, and arrangement of a glycemic insight can vary from that presented below.

Glycemic Insight Example 1

Focus: Bolus
Trigger: Shortly following the bolus delivery
Scenario: William (a Type I diabetes patient) is going to have lunch. To prepare for his lunch he gives himself an insulin bolus of 2.0 Units. Immediately after the bolus is delivered (which is indicated by an increase in the amount of insulin on board) a glycemic insight message is delivered from William's mobile app. The glycemic insight message includes the following information: "2.0 Units of bolus with carbohydrate <20 grams have been commonly found to result in a low glucose pattern in your history." In addition, the glycemic insight message includes a glucose profile plot of aggregated historical sensor traces following a bolus of 2.0 Units and <20 grams of carbohydrates that graphically depict the instances of low blood sugar.
Ending: William is now aware of his common trend of low blood sugar in association with a 2.0 Unit bolus and 20 grams of carbohydrates.

Glycemic Insight Example 2

User Scenario: Timmy (an eight year old Type I diabetes patient) was diagnosed at age six, has been on insulin for two years, and is a new pump user.
Insight Event: When Timmy takes a bolus followed by another bolus.
Historical Data: The system reviews glucose trends for all boluses delivered in the last seven days.
Specific Situation or Glucose Pattern: The system finds that boluses that were followed by another bolus within two hours (i.e., stacked boluses) usually result in a hypoglycemic pattern.
Glycemic Insight Message Content: "Timmy, in the past seven days, boluses when stacked were commonly found to result in a low glucose pattern." The insight message may also include a graphical element (a graph or a plot) that depicts the historical data, the corresponding glycemic outcome, or both.

Glycemic Insight Example 3

User Scenario: Steve (an 18 year old Type I diabetes patient) was diagnosed at age 14, has been on insulin for four years, and has been using an insulin pump for one year.
Insight Event: When Steve takes a bolus.
Historical Data: The system reviews glucose trends for all boluses delivered in the last 30 days.
Specific Situation or Glucose Pattern: The system finds that boluses with rapidly rising rate of change (ROC) of sensor glucose usually result in a hyperglycemic pattern.
Glycemic Insight Message Content: "Steve, in the past 30 days, boluses with rapidly rising ROC of sensor glucose were commonly found to result in a high glucose pattern." The insight message may also include a graphical element (a graph or a plot) that depicts the historical data, the corresponding glycemic outcome, or both.

Glycemic Insight Example 4

User Scenario: Joanne (a 36 year old Type 2 diabetes patient) was diagnosed at age 30, has been on insulin for one year, and has been using an insulin pump for six months.
Insight Event: Monday morning at 10:00 AM when no boluses are found.
Historical Data: The system reviews glucose trends for the last 90 days.
Specific Situation or Glucose Pattern: The system finds that mornings with no carbohydrate entry usually result in a hypoglycemic pattern.
Glycemic Insight Message Content: "Joanne, in the past 90 days, mornings without a carb entry were commonly found to result in a low glucose pattern." The insight message may also include a graphical element (a graph or a plot) that depicts the historical data, the corresponding glycemic outcome, or both.

Glycemic Insight Example 5

User Scenario: Ed (a 62 year old Type I diabetes patient) was diagnosed at age 26, has been on insulin for 34 years, and has been using an insulin pump for three years.
Insight Event: Sunday night at 10:00 PM.
Historical Data: The system reviews glucose trends for the last 90 days.
Specific Situation or Glucose Pattern: The system finds that Sunday nights with a rapidly rising rate of change in sensor glucose and without a carb entry usually result in a hyperglycemic pattern.
Glycemic Insight Message Content: "Ed, in the past 90 days, nights with a rapidly rising ROC of sensor glucose without a carb entry were commonly found to result in a high glucose pattern." The insight message may also include a graphical element (a graph or a plot) that depicts the historical data, the corresponding glycemic outcome, or both.

Glycemic Insight Example 6

User Scenario: Mary (an 18 year old Type I diabetes patient) was diagnosed at age 11, has been on insulin for seven years, and has been using an insulin pump for only two weeks.
Insight Event: When Mary takes a bolus.
Historical Data: The system reviews glucose trends for all boluses delivered in the last two weeks.
Specific Situation or Glucose Pattern: The system finds that boluses for carbohydrate intake of less than 20 grams usually result in a hypoglycemic pattern.
Glycemic Insight Message Content: "Mary, in the past two weeks, boluses with carbs <20 grams were commonly found to result in a low glucose pattern." The insight message may also include a graphical element (a graph or a plot) that depicts the historical data, the corresponding glycemic outcome, or both.

Glycemic Insight Example 7

User Scenario: Maxwell (a 25 year old Type I diabetes patient) was diagnosed at age four, has been on insulin for 21 years, and has been using an insulin pump for two years.
Insight Event: When Maxwell takes a bolus.
Historical Data: The system reviews glucose trends for all boluses delivered in the last seven days.
Specific Situation or Glucose Pattern: The system finds that boluses that were followed by another bolus within two hours (i.e., stacked boluses) usually result in a hypoglycemic pattern.
Glycemic Insight Message Content: "Maxwell, in the past seven days, boluses when stacked were commonly found to result in a low glucose pattern." The insight message may also include a graphical element (a graph or a plot) that depicts the historical data, the corresponding glycemic outcome, or both.
Insight Delivery Timing Referring again to FIG. 3, the insight delivery engine 306 is responsible for regulating the delivery, queuing, and discarding (if needed) of glycemic insight messages that have been generated by the insight generation engine 304. The insight delivery engine 306 controls the timing of when glycemic insight messages are delivered to the patients, and prioritizes the order of delivery for each patient. In contrast, current reporting mechanisms do not deliver patient-related analyses intelligently at a time most suitable for the users (e.g., at a time when users are likely to be attentive, are likely to read the insight messages, are likely to take appropriate action in response to the insight messages, etc.). The functionality of the insight delivery engine 306 enables the system 100, 300 to order and delivery the glycemic insight messages in an intelligent manner to increase the value and benefits for the patients.

In accordance with a bolus related example, when an insight is generated pertaining to a patient having hypoglycemic episodes after a bolus amount of 5-6 Units, the insight message is delivered within five minutes of a bolus taken on the next day, and three times a week following the event. This example can also be extended to delivering insight messages at specific times based on user behavior or habits using probabilistic models or machine learning techniques. For example, a patient having hypoglycemic episodes usually after a meal bolus can be alerted with an insight message in advance, based on models that calculate the meal time. The insight message can be delivered an hour before the predicted meal time.

In accordance with an example related to the day of the week, when an insight message is generated pertaining to a patient having more time in hyperglycemia on Fridays, the insight message is delivered at 8:00 AM (or after the first infusion pump action) and at 8:00 PM (or after the last infusion pump action) every Friday following the event. This example can also be extended to the time of day, wherein the insight message can be delivered at the beginning of the hour pertaining to the insight, to be delivered three times a week or on a specific day depending upon the content of the insight message.

In accordance with an example related to a high rate of change (ROC) of sensor glucose, when an insight message is generated pertaining to a patient having hypoglycemia after fast glucose changes for 45 mins, the insight message is delivered at the end of the high ROC period.

In accordance with an example related to a hyperglycemic event, when an insight message is generated pertaining to a patient having prolonged hyperglycemia followed by hypoglycemia, the insight message is delivered within five minutes of a detected hyperglycemia event. This example can also be extended to delivering the insight message an hour before the event based on a prediction of the hypoglycemia event or the hyperglycemia event, thereby enabling the patient to proactively monitor his glycemic outcome.

Additional information that can be used to manage, regulate, or otherwise control the delivery of insight messages are nutritional data and location data. In this regard, the user's location combined with routine meal time gathered from retrospective data can be used to provide insights on frequently visited places for lunch, frequent food intake, and how it relates to the user's glycemic outcome. For example, the insight messages can be delivered an hour before an approximate meal time, when the user is within 500 feet of a frequently visited restaurant or location that is otherwise associated with meal consumption, or the like.

Insight messages can also be delivered intelligently based on a consideration of patient activity tracking data. For example, an insight message can be delivered five minutes after a user finishes his routine workout or daily walk, after a threshold number of steps has been recorded, in response to a detected heartrate value, or the like. As another example, an insight message can be delivered if a patient remains stationary or sedentary for a long period of time (for hyperglycemia events triggered by sedentary lifestyle).

It should be appreciated that the above and other practical scenarios can influence the timing of insight message delivery. In this regard, the system 100, 300 can control the timing of insight message delivery based on one or more of the following, without limitation: triggered by static time; triggered by insight events; triggered by a glucose profile; triggered by a patient profile; or triggered by user request.

Triggering delivery based on static time refers to the delivery of an insight message based on a time of day, day of the week, week, month, year, holidays, or the like (as determined or defined by the system 100, 300 or as configured by a user). For example, insight messages about a certain consistent blood glucose excursion can be delivered at a specified time. As another example, insight messages regarding overeating during the holidays can be delivered on the morning of each holiday of interest, such as Easter, Christmas, Thanksgiving, and birthdays.

Triggering delivery based on insight events can involve any piece of available input data. A number of examples are provided below.

(1) Infusion pump alarms, sensor alerts, and other infusion system notifications can trigger delivery of an insight message. For example, insight messages about the best practice of threshold suspension can be delivered after generation or delivery of a threshold suspension alarm.

(2) Alarm and time triggered. For example, insight messages warning about how sweating will increase interference with the pump transmitter can be delivered in response to the generation of a "Lost Sensor" alarm during hot days.

(3) Location triggered. For example, insight messages about the glycemic outcome for certain food on a menu can be delivered when the user enters a restaurant.

(4) Location and time triggered. For example, insight messages about hypoglycemia occurrence can be delivered when the patient leaves the office, while in the parking lot at night.

(5) Activity triggered (exercise, sleep, meal). For example, insight messages about benefit of sleep early can be delivered when the patient sleeps late.

(6) Activity and time triggered. For example, insight messages having a warning that eating snacks before sleep can cause dawn phenomenon can be delivered at night after the patient eats something.

(7) Calendar triggered (meetings, vacations, appointments, social activities). For example, insight messages related to how many insulin vials the patient should bring for a planned trip can be delivered a day before the trip. In certain embodiments, this type of insight message can be formatted and provided such that it appears on the patient's calendar app or desktop user interface.

(8) Disease triggered (from the user, medical staff, a prescription, etc.). For example, insight messages related to how certain diseases can impact the blood glucose control can be delivered when the patient or a caregiver identifies a specific disease, condition, or ailment, or when a prescription is filled.

Triggering delivery of insight messages can also be influenced by the patient's glucose profile characteristics. A few examples are provided below.

(1) Continuous glucose profile (worsen control, excursion event). For example, an insight message including a reminder about an abnormal recent glucose profile can be delivered when the abnormality is detected.

(2) Discrete glucose profile (large difference between a meter BG entry). For example, if a user's usual glucose profile is 120±30 mg/dL on Tuesday afternoon, but today the user logged in a value at 400 mg/dL, an insight message can be delivered at this point (discussing what could happen following such abrupt event).

(3) Abrupt change from history. For example, an insight message can be delivered in response to an improvement or deterioration in the patient's glucose profile over the past week, month, or year. Such an insight message can be triggered as soon as the change in the glucose profile is detected.

Triggering delivery of insight messages can also be influenced by the patient's user profile. For example, a general blood glucose distribution from users who have a similar (age, gender, years using an insulin infusion pump, etc.) can be generated as an insight message for a new user who just registered his profile into the system. This type of insight message can be used as a benchmark for patients who want to know how they are doing compared against similarly situated patients.

Triggering delivery of insight messages can also be influenced by user requests (by the patient, a caregiver, a healthcare provider, etc.). For example, the patient, a parent, a physician, or a nurse practitioner can request the delivery of insights as needed.

Triggering delivery of generated insight messages can also be influenced by preferred timing for the individual user, wherein the timing can be based on detected trends, user input, user feedback, or the like. In this context, insight messages can be delivered at a time that is best suited for the particular individual. For example, if the user is in the habit of browsing news websites on his mobile device every morning at 6:15, then the system can assume that the best time for daily insight message delivery will be at or near 6:15 AM.

Insight Delivery Timing Optimization

The timing of insight message delivery can also be optimized gradually based on feedback from users, as mentioned above. The user feedback can include any or all of the following, without limitation: (1) the amount of time it takes for the user to actually view the insight message on the device platform (tablet, phone, etc.); (2) the user's response to the insight messages (if any), such as "like" or "dislike" or "don't show this again"; (3) the user's corrective activity following delivery and viewing of an insight message; (4) the user's glucose outcome after delivery of an insight message; and (5) the user's engagement based on responsiveness and time spent viewing an insight message. The insight delivery engine 306 can be dynamically updated and configured as needed to react to such user feedback in a way that enhanced the delivery timing of subsequent insight messages.

Insight Delivery Method—Visualization

A glycemic insight message can be generated and provided in any desired format, although preferably formatted in an easy to read, easy to understand, and intuitive manner. The specific format, content, appearance, and functionality of an insight message can vary depending on the type of insight being conveyed, the user's device platform, user preference settings, and the like. For example, the format and/or font size of an insight message can be adjusted to accommodate users with poor eyesight. Enhanced ways of delivering insight messages can be superior to traditional text-based statements in terms of patient adherence and glycemic outcome. Several examples are presented below; these examples are not intended to be exhaustive or limiting in any way.

Figure 4:
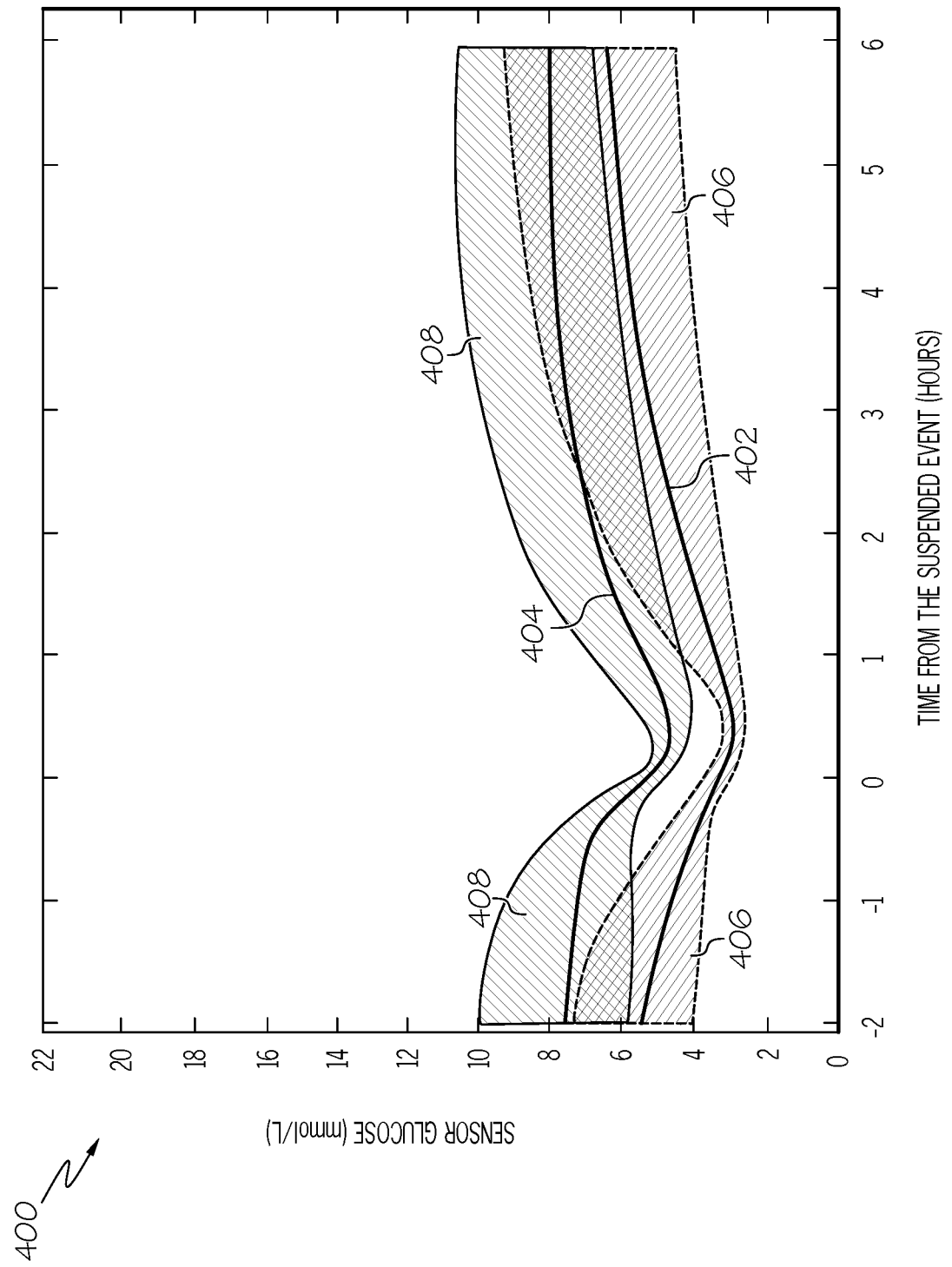
FIG. 4 is a graph of sensor glucose, which represents a graphical element of a glycemic insight message.

(1) Overlapped Glucose Swoosh Curve—The patient's sensor glucose data can be graphically presented using multiple swoosh curves with a highlighted line that indicates the median or mean, and side bands that indicate interquartile range. Thus, one or more glucose profile plots for the user of the insulin infusion device can be rendered in association with a glycemic insight message. General percentiles or outliers can be overlaid to show good versus bad outcomes corresponding to different variable(s). As an example, FIG. 4 is a graph 400 of sensor glucose, which can serve as a graphical element of a glycemic insight message. The graph 400 indicates time relative to a suspend event for the insulin infusion device. The plot 402 indicates the suspend OFF median, and the plot 404 indicates the median associated with a Predictive Low Glucose Management (PLGM) output. The zone 406 bounded by dashed lines indicates the suspend OFF interquartile range (IQR), and the zone 408 bounded by solid lines indicates the PLGM IQR. For this embodiment, the band defined between the plot 402 and the plot 404 represents the median plus IQR. Note that sections of the zone 406 overlap with sections of the zone 408. A visualization of the type shown in FIG. 4 can be provided with an insight message as needed.

Figure 5:
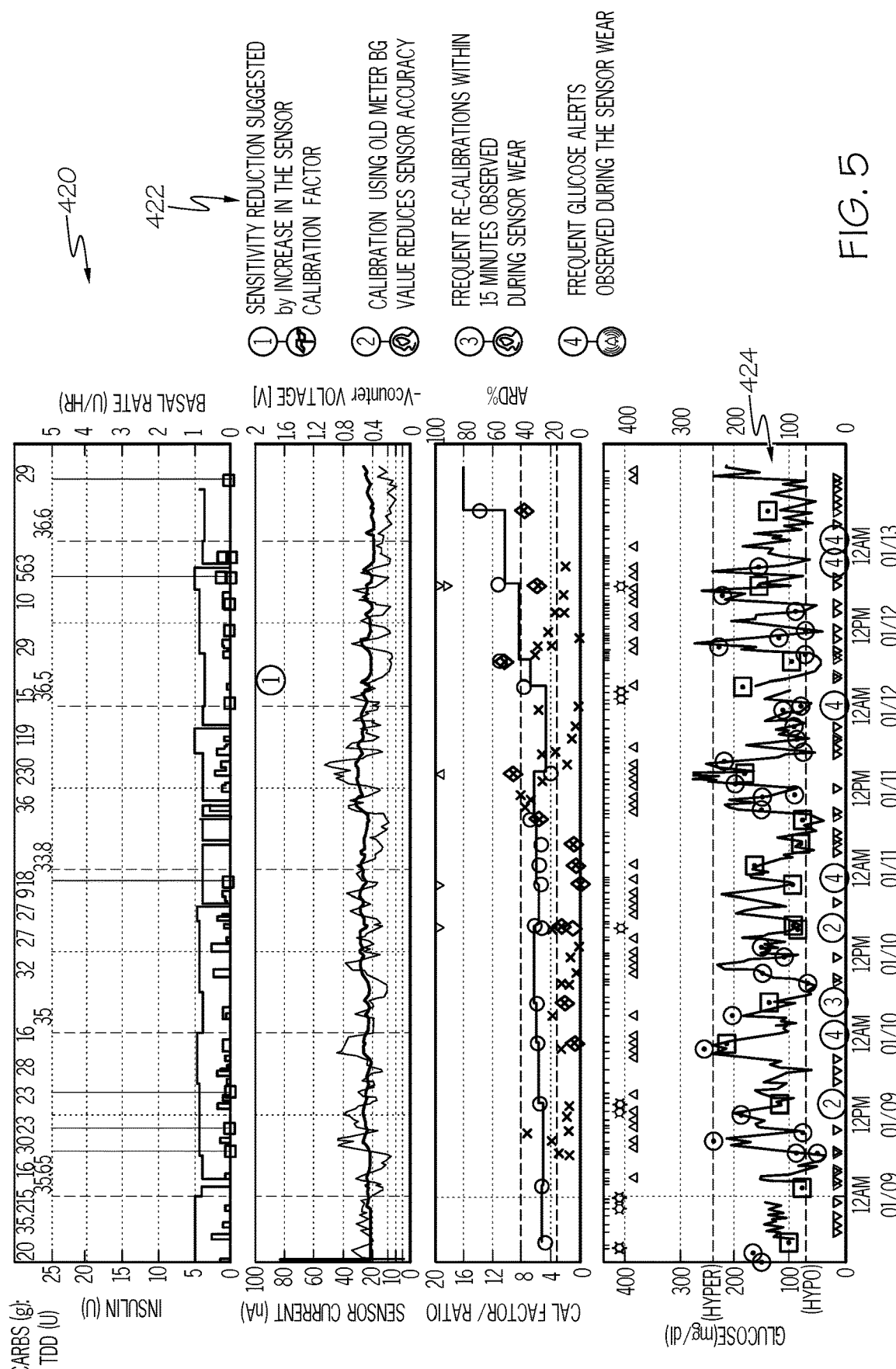
FIG. 5 is a diagram that depicts how glycemic insight messages can be provided on a patient's glucose profile.

(2) Annotated Glucose Profile—Insights (e.g., references to and/or active links to insight messages) can be directly annotated on the patient's glucose profile to emphasize when and where certain triggering events happened. The context of the insight messages can influence where on the glucose profile the reference or link appears. As an example, FIG. 5 is a diagram 420 that depicts how glycemic insight messages can be delivered on a patient's glucose profile. In FIG. 5, the numbered circles that appear on the plots indicate glycemic insights corresponding to the explanatory legend 422 that appears on the right side of the diagram 420. The positioning of the numbered circles correspond to the insight events that trigger or otherwise influence the generation of the insight messages. See, for example, the glucose plot 424 at the bottom of the diagram 420, where multiple insights are located at different points along the timeline. In certain embodiments, the numbered circles (or whatever label, icon, or identifier graphically represents the glycemic insights) are active elements that can be selected by the user to display or otherwise present additional details related to the selected insight.

Figure 6:
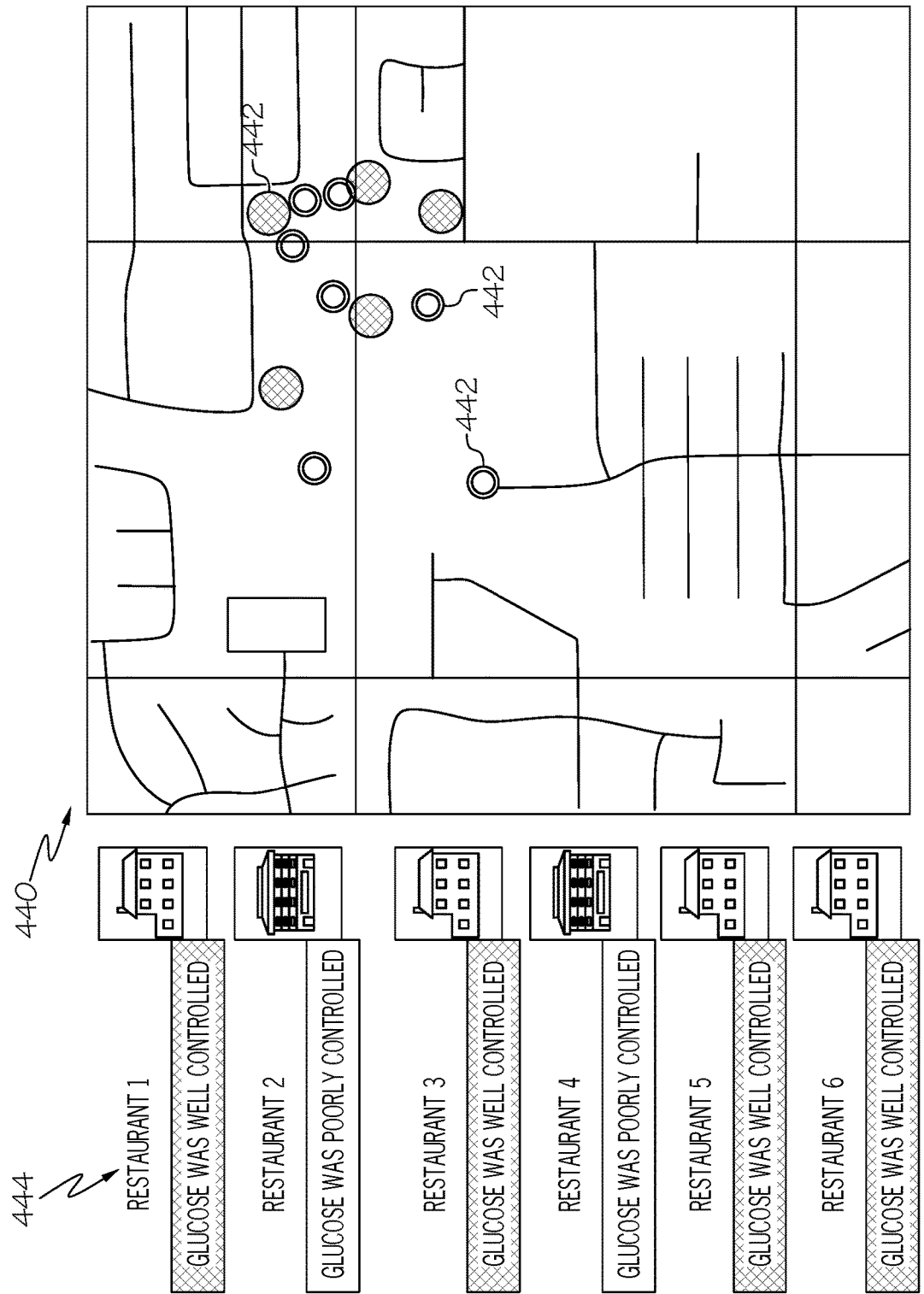
FIG. 6 is a graphical representation of a map having glycemic insight information rendered therewith.

(3) Annotated Map—Insights (e.g., references to and/or active links to insight messages) can be rendered on a geographical map, beside the map, or otherwise generated in association with the map to provide an amount of geographical context to the insight messages. For example, meal or food related glycemic insights can be associated with particular restaurants, locations, addresses, or the like, and a map can utilized to identify the locations that correspond to those insights. As an example, FIG. 6 is a graphical representation of a map 440 having glycemic insight information rendered therewith. The map 440 includes insight markers 442 (rendered as colored circles overlying the geographical features of the map 440). Each insight marker 442 corresponds to a glycemic insight. For this example, each insight marker 442 is associated with additional descriptive content 444, which appears on the left side of FIG. 6. The descriptive content 444 may include information related to the geographical location, such as "phone book" information, the name of the business, user reviews or ratings, pictures, and the like. For this particular embodiment, the descriptive content 444 also includes a color coded message that matches the color of the associated insight marker 442. For example, the message "Glucose was well controlled" can be rendered in green, and the message "Glucose was poorly controlled" can be rendered in orange. Important or critical messages can be rendered in red, or in a highlighted font, etc. These colors are preferably used in a consistent manner for the insight markers 442, such that the user can quickly identify geographic locations where glucose was well controlled, poorly controlled, out of range, and the like. In certain embodiments, the insight markers 442 and/or the descriptive content 444 are active elements that can be selected by the user to display or otherwise present additional details related to the selected glycemic insight.

Figure 7:
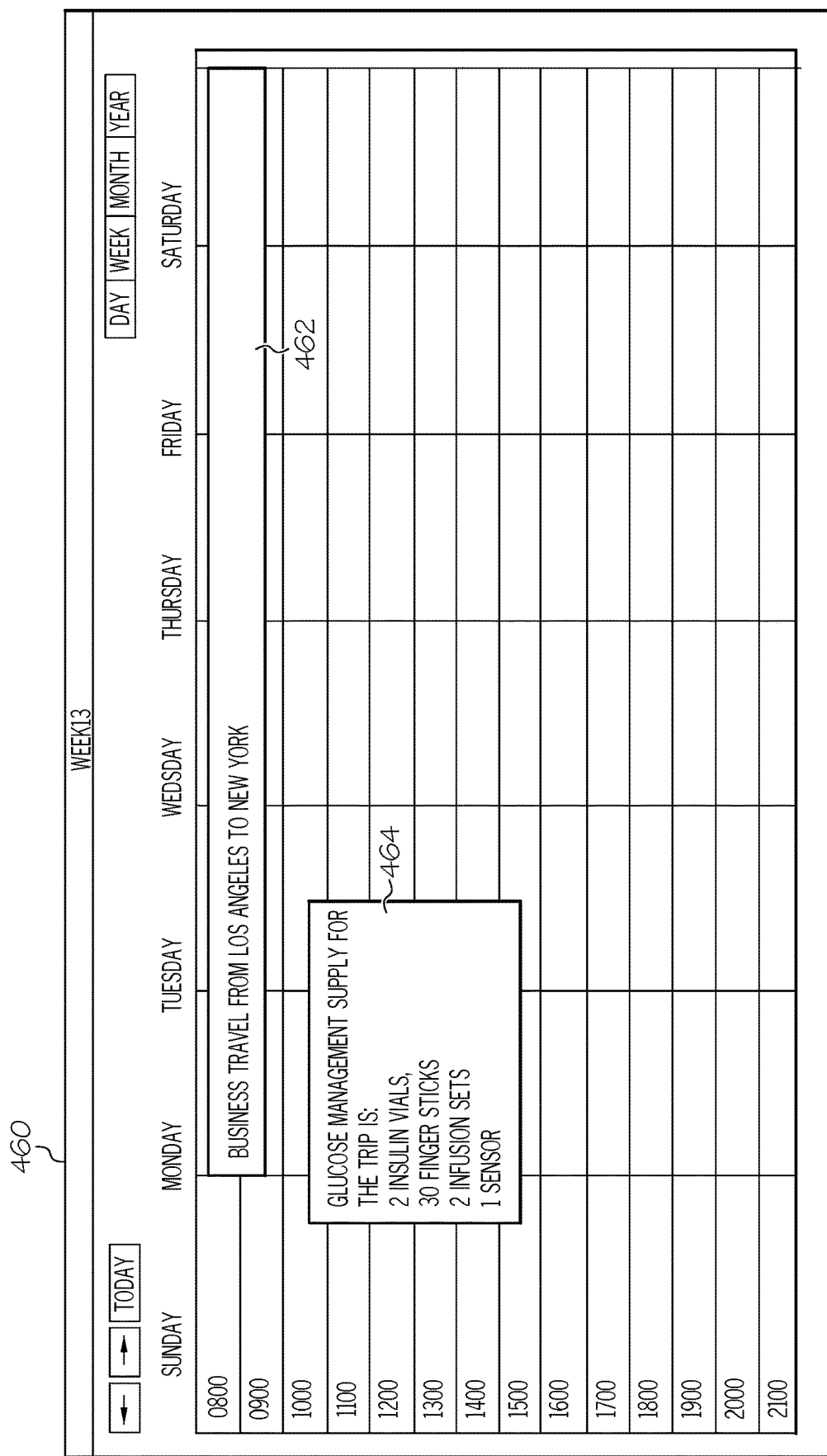
FIG. 7 is a graphical representation of a displayed screen of a calendar app having glycemic insight information rendered therewith.

(4) Annotated Calendar—Insights (e.g., references to and/ or active links to insight messages) can be rendered in or otherwise generated in association with a user's calendar app to link the insight messages to certain calendar events. Ideally, calendar-linked glycemic insight messages are predictive in nature, and they appear before the start of the associated calendar event. For example, glycemic insights that are related to certain days of the week, travel to specific cities or events, vacations, sporting events, or any scheduled event can be displayed as a calendar entry or as a note or annotation of a calendar entry. As an example, FIG. 7 is a graphical representation of a displayed screen 460 of a calendar app having glycemic insight information rendered therewith. For the illustrated example, the user's calendar app includes an entry 462 for an extended business travel event. A glycemic insight message 464 is rendered in association with the entry 462, wherein the glycemic insight message 464 is contextually related to the entry 462. In this regard, the insight message 464 includes a reminder regarding the medical supplies that the patient needs to pack for the business trip. It should be appreciated that the particular content of calendar-linked insight messages will vary depending upon the calendared event (if any), the date or time, and the like. In certain embodiments, the insight message 464 (or portions thereof) includes one or more active elements that can be selected by the user to display or otherwise present additional details related to the calendar-linked glycemic insight.

Figure 8:
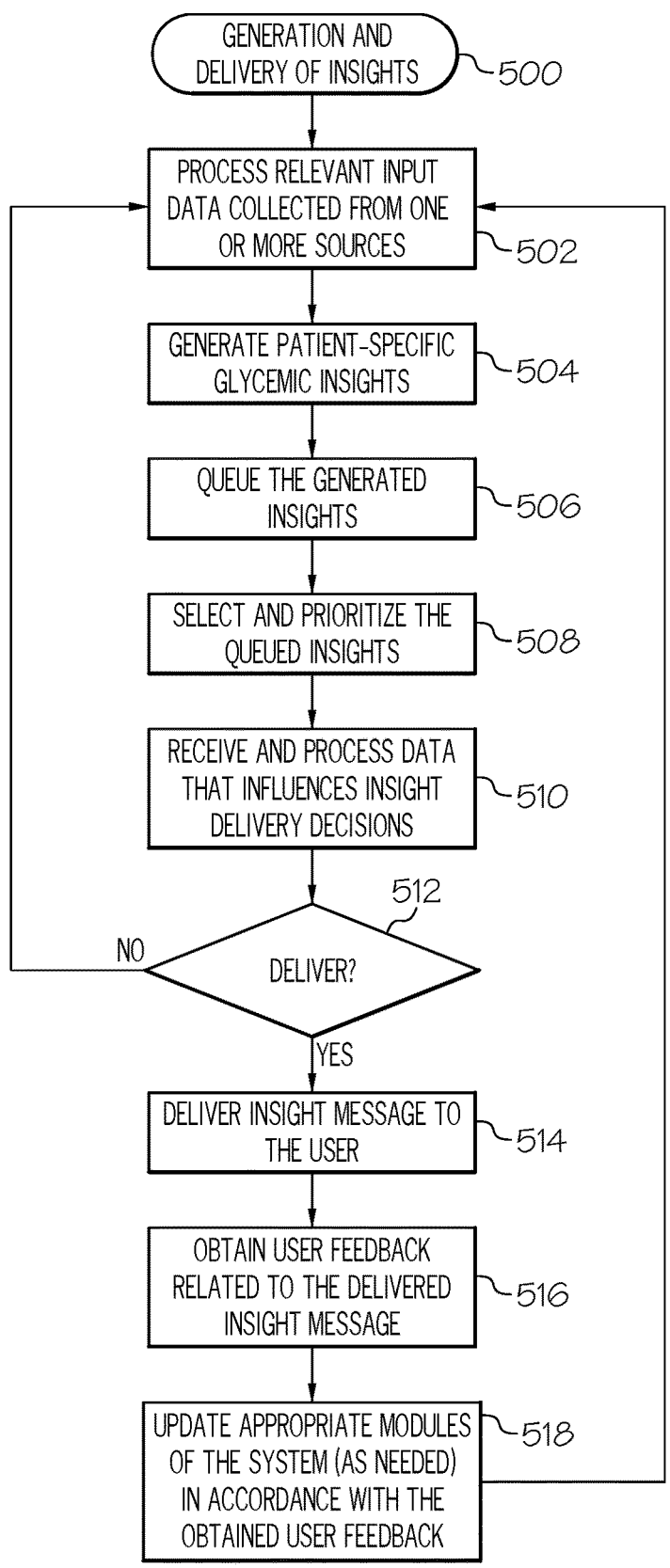
FIG. 8 is a flow chart that illustrates an exemplary embodiment of a process for generating and delivering glycemic insights.
Figure 9:
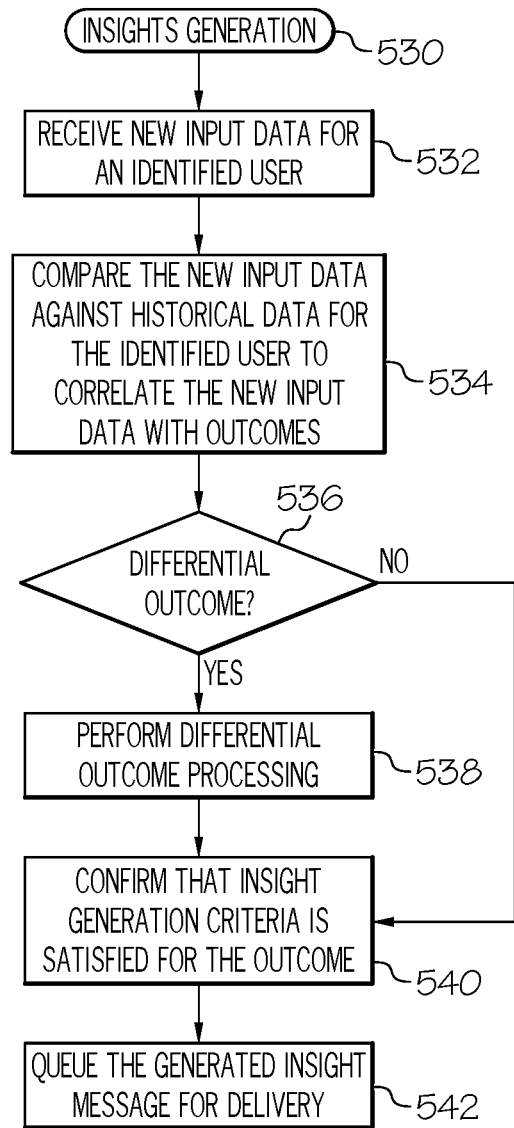
FIG. 9 is a flow chart that illustrates an exemplary embodiment of an insights generation process.

FIG. 8 is a flow chart that illustrates an exemplary embodiment of a process 500 for generating and delivering glycemic insights, and FIG. 9 is a flow chart that illustrates an exemplary embodiment of an insights generation process 530. The various tasks performed in connection with a process described herein may be performed by software, hardware, firmware, or any combination thereof. For illustrative purposes, the following description may refer to elements mentioned above in connection with FIGS. 1-7. In practice, portions of a described process may be performed by different elements of the described system or by a processing module of a system element. It should be appreciated that a process described herein may include any number of additional or alternative tasks, the tasks shown in a figure need not be performed in the illustrated order, and a described process may be incorporated into a more comprehensive procedure or process having additional functionality not described in detail herein. Moreover, one or more of the tasks shown in a figure could be omitted from an embodiment of the process as long as the intended overall functionality remains intact.

In practice, the system 100, 300 collects and analyzes data for multiple patients. Indeed, the centralized cloud-based deployment of the system 100, 300 allows it to be scalable to accommodate a large number of patients. Thus, the techniques and methodologies described herein related to the generation and delivery of glycemic insight messages can be performed at any time for different patients. For the sake of brevity and simplicity, the processes 500, 530 are described with reference to only one user/patient. It should be appreciated that an embodiment of the system 100, 300 will expand the processes 500, 530 in a way that accommodates a plurality of different users/patients.

The process 500 begins by obtaining and processing relevant input data collected from one or more sources (task 502). As explained above, the input data sources will typically be a mobile app executing on the user's device, and at least one medical device that provides data related to the operation of the user's insulin infusion device. This example assumes that the system 100, 300 has already been deployed for at least a baseline period of time during which relevant input data has been gathered and stored for purposes of making intelligent and meaningful comparisons against newly received input data. In other words, it is assumed that the database system 116, 308 has already been populated with historical entries that associate monitored events with outcomes. That said, if the system does not have enough historical data for a patient for purposes of generating personalized glycemic insights, it can still generate an insight if there is a strong correlation between a monitored event and an outcome seen in different patients with user profiles that are similar to the profile of the patient under investigation.

As a simple example, assume that there are only three event features of interest and only four possible outcomes. Also assume that an insight event can be defined as any combination of one or more event features. For this example, there are seven insight events (corresponding to all possible combinations of one, two, or all three event features). Each historical entry in the database system 116, 308 identifies or includes one of the insight events, along with outcome data for each of the four possible outcomes. Conceptually, each historical entry can be visualized as a row in an event/outcome table, wherein the row identifies the particular insight event of interest (e.g., columns that include the data for each event feature) along with information related to the different possible outcomes (e.g., columns that include the outcome data). For example, a historical entry may identify an insight event that includes a combination of two event features, Yes/No identifiers for non-differential outcomes, and specific values for differential outcomes. As time progresses, the database system 116, 308 will become populated with ongoing occurrences of the insight events, along with the corresponding outcome data.

In certain embodiments, task 502 identifies a current set of input data for a particular user, and compares the user input data against historical user-specific data combinations maintained for the particular user. Each of the historical user-specific data combinations includes insight event data that is indicative of a glycemic event, and a glycemic outcome corresponding to the insight event data. Stated another way, the insight events indicated by the newly received input data are compared against the insight events contained in the historical data maintained in the database system 116, 308. This allows the system 100, 300 to compare newly received input data against historical data to determine whether or not there exists a significant correlation between an insight event and one or more glycemic outcomes.

The process 500 analyzes the input data and the data combinations to generate patient-specific glycemic insights as needed (task 504). In this regard, the system determines a correlation between the current set of user input data and a particular glycemic outcome and, in response to the determination, generates a glycemic insight message that is intended for delivery to the user. The glycemic insight message includes information regarding a relationship between at least some of the current set of input data and the particular glycemic outcome. This description assumes that the process 500 queues the generated insight messages as they are generated (task 506).

The process 500 continues by selecting and prioritizing the queued insights according to a desired delivery prioritization scheme (task 508). In practice, the system can receive and process real time and other data that influences certain insight message delivery decisions (task 510). If the process 500 determines that it is time to deliver a specific insight message to the user (the "Yes" branch of query task 512), then the insight message is delivered to the user's mobile device (task 514). It should be appreciated that the process 500 may alternatively or additionally send the insight message to the patient's insulin infusion device, to a non-mobile computing device, to an electronic device operated by a non-patient user or caregiver, or the like. Although not always applicable, this example assumes that the process 500 obtains user feedback related to the delivered insight message (task 516). In response to the obtained user feedback, the process 500 updates appropriate modules of the glycemic insights delivery system (as needed) in an attempt to optimize future insight delivery operations.

FIG. 9 depicts one exemplary approach for generating a glycemic insight. Accordingly, the process 530 can be performed during task 504 of the process 500. The process 530 assumes that new input data has been obtained and collected for an identified user, such that the system can check whether or not any glycemic insights should be generated in response to the new input data (task 532). The new input data is compared against the historical data that is maintained for the identified user (task 534). More specifically, the input data obtained for the user is compared against historical event/outcome combinations maintained for that user, to determine whether the current or new input data indicates a matching condition. To make the comparison easier and more efficient, the system may discretize the values of continuous event features (i.e., event features having a variable range of input data values, such as sensor glucose readings). In this regard, the exemplary embodiment described here discretizes values of continuous event features into ten ranges or bins, such that the bin numbers (bins 1 to 10) can serve as indices for the process 500. Similarly, the system may translate event feature values into numerical form or into any format that is easier to handle. For example, the event feature "Day of the Week" can be expressed in numerical form such that Sunday is represented by the number 1, Monday is represented by the number 2, and so on.

The comparison is performed to determine whether there is any matching or correlation between the new input data and glycemic outcomes. As explained above, the system can handle differential outcomes and non-differential (direct) outcomes. Thus, if an outcome under investigation is a differential outcome (the "Yes" branch of query task 536), then the process 530 performs differential outcome processing (task 538). Otherwise, the process 530 continues by confirming that the insight generation criteria is satisfied for the outcome under investigation (task 540). This description assumes that the insight generation criteria is satisfied and, therefore, that the process 530 generates and queues an appropriate glycemic insight message for delivery (task 542).

The particular insight generation criteria used by the process 530 may vary from one embodiment to another. In accordance with the exemplary embodiment presented here, the process 530 analyzes the historical event/outcome combinations to count the number of times that the insight event of interest has occurred in the designated historical window of time (e.g., the last month, the last three months, the last year, etc.). The number of occurrences is then compared against a predetermined threshold number. If the total number of occurrences during the designated window of time does not exceed the threshold, then the process 530 refrains from generating a glycemic insight for that particular insight event. The threshold number can vary depending on the insight event being analyzed and/or depending on the outcome being analyzed. If the total number of occurrences exceeds the threshold, then the process 530 continues by checking the different glycemic outcomes recorded for the historical instances of the insight event. Thus, for this described embodiment, the process 530 confirms that the insight generation criteria is satisfied only when the total number exceeds the threshold, even though additional criteria may apply. If a given outcome occurs at a high enough frequency (for the particular insight event), then the process 530 assumes that there is a strong correlation between that insight event and the given outcome, and generates a glycemic insight for that particular event/outcome combination. For example, if the given outcome occurred more than 80% of the time (or more than any desired threshold percentage value) for recorded instances of the particular insight event, then the insight generation criteria is satisfied. If not, then the process 530 refrains from generating a glycemic insight for that particular insight event. It should be understood that the process 530 can analyze each of the different outcomes to determine whether or not any of them is strongly correlated to the event under investigation.

The process 530 handles differential outcomes in a slightly different manner. As mentioned above, the exemplary embodiment of the system 100, 300 contemplates a total of ten glycemic outcomes: five "direct" or non-differential outcomes, and five differential outcomes. A non-differential outcome is binary in that it will have one of two possible states, such as Yes/No, High/Low, On/Off, or Active/Inactive. In contrast, a differential outcome is an outcome having a variable range. Thus task 538 is used to convert the variable range from a differential outcome to binary values (e.g., the differential outcome "percent time in hypo" is converted to binary values such as: whether current percent time in hypo is more than the average percent time in hypo in the history). Following the task 538, task 540 can be applied to the converted outcome in the same manner as a non-differential outcome.

Task 538 can analyze the differential outcomes contained in historical data using any desired methodology, algorithm, or approach. The exemplary embodiment presented here calculates the mean outcome value for the insight event of interest, as recorded during the time window of interest (e.g., the last month, the last three months, or the last week). The standard deviation is also calculated, and a percentage of the standard deviation is added to the calculated mean. For this example, half of the standard deviation is added to the calculated mean to obtain a baseline value for the differential outcome under analysis. Next, the exemplary methodology checks whether the value of the differential outcome under analysis is greater than the baseline value. This check is performed to determine whether the differential outcome under analysis is likely to be the result of the insight event of interest. If the value of the differential outcome is greater than the baseline value, the process 530 outputs "Yes". If the value is less than the baseline value, the process 530 outputs "No". All of the converted Yes and No outputs are then passed into task 540 to be treated in the same manner as a non-differential outcome, to compare against the insight generation criteria.

In practice, the approach described here can be repeated for all of the differential outcome values that are associated with an insight event of interest. After considering all of the recorded differential outcome values, the process 530 can identify which one (if any) has a strong correlation with the insight event of interest.

The differential outcome processing of task 538 is intended to remove "patient bias" to allow the system 100, 300 to compare each insight event against the individual patient baseline characteristics rather than any fixed threshold outcome value. Thus, the process 530 considers the patient's average glycemic outcome and generates a related glycemic insight message only if the insight event under analysis is actually correlated to a differential outcome that appears to be somewhat of an "outlier" relative to the average patient response.

Insights Curation

As mentioned briefly above, the timing of insight message delivery is an important aspect of the system 100, 300. In preferred implementations, glycemic insight messages are delivered to the patients in an intelligent manner that is designed to increase the likelihood of actual viewing and follow up action by the patients. The manner in which the system 100, 300 handles the culling, prioritization, and delivery timing of glycemic insights is described in more detail in this section.

Managing the delivery of glycemic insight messages is needed due to the large volume of insight messages that can be generated over time for each patient. Due to the 600+ different data patterns that are considered, along with different possible glycemic outcomes, redundant or similar glycemic insight messages (i.e., insights having the same or equivalent content) can be generated. Moreover, in certain situations "conflicting" glycemic insight messages can be generated. For example, one insight message can say that it is easier to experience a hypoglycemic episode while another insight message can say that a hyperglycemic episode is more likely during the same time window. Managing the delivery of insight messages is also desirable to accommodate the personal preferences of the end users, and to reduce the occurrence of annoying messages and notifications.

Figure 10:
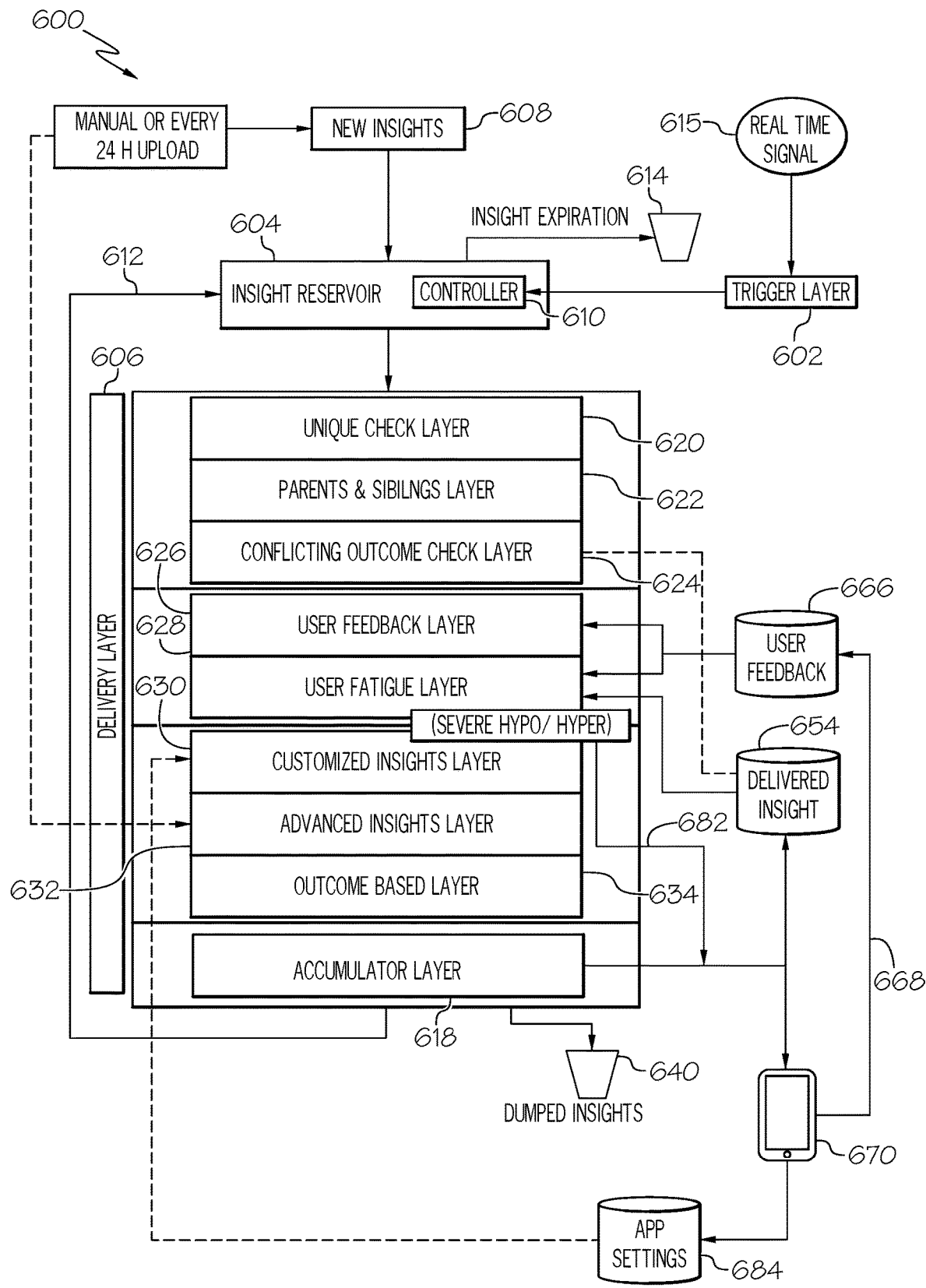
FIG. 10 is a schematic block diagram of a layered structure suitable for use with the insight delivery engine shown in FIG. 3.

Referring again to FIG. 3, the insight delivery engine 306 is suitably configured to manage the delivery of glycemic insight messages to the patient's mobile device 302. In certain embodiments, the insight delivery engine 306 employs a plurality of processing layers, wherein each layer handles a particular function. The layers of the insight delivery engine 306 are expandable, customizable, and independent. In this regard, FIG. 10 is a schematic block diagram of a layered structure 600 suitable for use with the insight delivery engine shown in FIG. 3. The layered structure 600 generally includes a trigger layer 602, an insight reservoir 604, and a delivery layer 606. These elements cooperate in the manner described below handle the processing of new glycemic insights 608 as they are generated.

Insight Reservoir

The insight reservoir 604 obtains, collects, and sluices the glycemic insights upon triggers. The insight reservoir 604 includes all insight messages generated for a given patient. Conceptually, the insight reservoir 604 is initially empty with no insight messages contained therein. Over time, however, the insight reservoir 604 gets populated with insight messages as they are generated; the insight reservoir 604 holds the generated insight messages prior to delivery. The insight reservoir 604 includes a controller 610 associated therewith, and the controller 610 monitors and listens to the incoming triggers (e.g., real-time trigger conditions) from the trigger layer 602. Whenever a new bundle of triggers is received, the controller 610 performs the following operations: (1) gathers the new insights 608 and the remaining insights 612 from the previous delivery; (2) removes any insights that have been residing in the insight reservoir 604 for more than a designated period of time, which is one month for the exemplary embodiment; and (3) fetches the insights matching the received trigger conditions; and (4) sends the matching insights to the delivery layer 606. The trashcan icon 614 in FIG. 10 indicates the destination for the "expired" insights that are removed at Step (2) of the process outlined above.

Trigger Layer

The trigger layer 602 determines when to trigger the delivery of generated glycemic insights, such that the insights can be pushed out to the user. Triggering in this context means activating delivery for an insight message, removing it from the insight reservoir 604, and sending it to the delivery layer 606. This can be important for handling certain glycemic insight messages that are related to time sensitive or condition sensitive factors. For example, if an insight relates to high glucose trends that occur on Mondays, then that particular insight can be triggered on Monday morning or Sunday evening. As another example, if an insight message relates to a rapid change in sensor glucose, then the trigger layer 602 can monitor for such a rapid change occurring in real time before triggering delivery of that particular insight message.

The embodiment of the trigger layer 602 described here utilizes the following as input information, which is used to calculate the triggers: (a) sensor glucose readings (in mg/dl) at five minute intervals; (b) active insulin measurements (in Units of insulin) at five minute intervals; and (c) the current time. In FIG. 10, the real time signal 615 represents the input information for the trigger layer 602, which is reviewed to determine whether or not certain real-time trigger conditions have been satisfied. The sensor glucose readings and the active insulin measurements can be provided by the mobile app that is resident on the patient's mobile device 104, 302. Alternatively or additionally, some of the real-time input information (trigger data) can be provided by the patient's insulin infusion device. The output of the trigger layer 602 includes triggers that are sent to the insight reservoir 604. In accordance with certain embodiments, the trigger layer 602 includes a pre-processing layer, trigger generators, and a trigger collector. These elements of the trigger layer 602 cooperate to generate the output triggers in response to the input information.

Different real time triggers can be utilized to trigger the delivery of corresponding types of glycemic insights. In accordance with certain embodiments, one or more of the following categories of triggers can be considered: bolus; day; time of day; threshold suspend; hyperglycemia; sensor glucose ROC; and meal (based on nutrition). Each of these triggers can have one or more insight conditions associated therewith, and each insight condition is associated with particular content that is conveyed in the respective glycemic insight message.

The following insight conditions can be associated with a bolus related trigger: bolus amount; type of bolus (square, dual, normal); has stacked bolus; has stacked correction bolus; active insulin amount; bolus type obtained from bolus calculator (Meal, Correction); carb amount obtained from bolus calculator; correction amount obtained from bolus calculator; carb ratio setting obtained from bolus calculator; dual wave bolus; insulin sensitivity setting obtained from bolus calculator; override from bolus calculator; underride from bolus calculator; sensor glucose ROC at bolus; mean sensor glucose in the previous 15 minutes; time since previous bolus; basal pattern; time of day; and day of week (weekday or weekend).

The following insight conditions can be associated with a day related trigger: days since infusion change; day of week (weekday or weekend); holiday; basal patterns; time in range, hypo or hyper on previous day; sensor glucose at the start of the day (first infusion pump action); sensor glucose at the end of the previous day (last infusion pump action); TDD; TDD compared to daily average; blood glucose measurement frequency; blood glucose measurement frequency compared to daily average; number of meals; number of meals compared to daily average; number of boluses; number of boluses compared to daily average; number of food boluses; number of food boluses compared to daily average; number of correction boluses; number of correction boluses compared to daily average; total daily carbohydrate amount; average carbohydrate amount compared to daily average; total daily bolus; total daily basal; basal bolus ratio; basal bolus ratio compared to daily average; dawn; morning first bolus unusually early; morning first bolus unusually late.

The following insight conditions can be associated with a time of day related trigger: time block (morning, breakfast, lunch, dinner, before sleep); day of week (weekday or weekend); basal pattern; bolus time; bolus count during the time period; total bolus count compared to daily average; total carbohydrate in the time bucket; total daily carbohydrate amount compared to daily average; number of food boluses; number of food boluses compared to daily average; number of correction boluses; number of correction boluses compared to daily average; blood glucose measurement frequency; blood glucose measurement frequency compared to daily average; time in range, hypo or hyper in previous time bucket; and time in range, hypo or hyper compared to daily average.

The following insight conditions can be associated with a threshold suspend related trigger: threshold suspend setting; suspend duration; user response (suspend response time); active insulin; sensor glucose ROC in previous 30 minutes; time until first carbohydrate intake; time until first bolus; sensor glucose end value before resuming manually; time of day; day of week (weekday or weekend).

The following insight conditions can be associated with a hyperglycemia related trigger: duration; user action during hyperglycemia (bolus, correction, meal, temporary basal); peak point; time of day; and day of week.

The following insight conditions can be associated with a sensor glucose ROC related trigger: mean sensor glucose in previous 15 minutes; time since previous bolus; whether the carbohydrate amount is within [−30, 0] minutes of the high ROC period; whether the bolus amount is bolus amount within [−30, 0] minutes of the high ROC period; time of day; day of week; and duration.

The following insight conditions can be associated with a meal related trigger: carbohydrate amount; food type; nutrient amounts; bolus amount; bolus type (square, normal); time of day; and day of week.

The pre-processing layer of the trigger layer 602 cleanses the time series. In this regard, common issues with the input information include, without limitation: out of range values; data artifacts; overlapping data; and inaccurate data. The pre-processing layer can serve as a filter that improves the quality and accuracy of the trigger layer 602.

The trigger generators of the trigger layer 602 generate the triggers based on the pre-processed signals from the pre-processing layer. For the embodiment described herein, each trigger generator is independent, in that the operation of each trigger generator does not depend on the operation or processing performed by any of the other trigger generators. The number of trigger generators utilized by the trigger layer 602 is flexible and expandable; there is no limitation on the amount of trigger generators used by the system 100, 300. The trigger generators are customizable in that they can be modified to consider additional input information, such as user actions.

The trigger collector of the trigger layer 602 bundles all of the generated triggers and sends them out according to an internal scheduler. The scheduler controls the how frequent the triggers are sent to the insight reservoir 604. The scheduler may utilize a static schedule or a dynamic schedule, as needed. In accordance with a static schedule, the trigger collector sends out the triggers at fixed time intervals (for example, every 15 minutes). In accordance with a dynamic schedule, the trigger collector sends out the triggers using a variable timing scheme (for example, shorter intervals during the day and longer intervals in the evening).

Delivery Layer

The delivery layer 606 cleanses, organizes, culls, and prioritizes the triggered insights and pushes them to the users. The delivery layer 606 can filter or otherwise regulate the number of triggered insight messages in an appropriate manner to identify a smaller group of insight messages that are intended for delivery to the user device. The delivery layer 606 is arranged as a hierarchical structure having multiple sublayers. The sublayers function as filtering sublayers wherein upper layers can filter a group of candidate insight messages as needed before passing at least some of the group to the next lowest sublayer. For the exemplary embodiment presented here, each of the sublayers processes a candidate glycemic insight message by doing one of the following: passing the candidate glycemic insight message to a lower layer in the hierarchical delivery layer structure; sending the candidate glycemic insight message back to the insight reservoir 604; or discarding the candidate glycemic insight message. The sublayers of the delivery layer 606 can be categorized or organized as follows: reduction layers; user related layers; weight based layers; and an accumulator layer 618, arranged in hierarchical order with the reduction layers at the top of the hierarchy and the accumulator layer 618 at the bottom. For this particular example: the reduction layers include a unique check layer 620, a parents and siblings layer 622, and a conflicting outcome check layer 624; the user related layers include a user feedback layer 626 and a user fatigue layer 628; and the weight based layers include a customized insights layer 630, an advanced insights layer 632, and an outcome based layer 634.

Each layer of the delivery layer 606 uses the output from the preceding (upper) layer as an input and categorizes it into one of three groups: downstream insights that serve as the input to the next lowest layer; remaining insights that are not ready or suitable for delivery during the current processing iteration and are sent back to the insight reservoir 604 for the next iteration; or dumped (discarded) insights that are no longer useful. The trashcan icon 640 in FIG. 10 represents the destination for these dumped insights. The uppermost layer of the delivery layer 606 (i.e., the unique check layer 620 for this example) uses the output of the insight reservoir as its input.

The reduction layers compare the set of triggered insight messages to each other, and function to remove redundant and conflicting glycemic insights such that they do not "clog" the insight delivery feed to the user. For example, the unique check layer 620 reviews the current batch of glycemic insights to identify identical insights. If the unique check layer 620 finds repeated instances of the same insight, then it determines which of the repeated insights represents the most current version (the most recently generated insight). The most recently generated instance of the insight is provided to the next layer, and the redundant instances are discarded as "dumped insights".

The parents and siblings layer 622 handles glycemic insights having some form of hierarchical relationship with other glycemic insights (i.e., a parent-child relationship or a sibling relationship), wherein insights with such a hierarchical relationship might be triggered simultaneously. For example, the following glycemic insights are related to one another for purposes of the parents and siblings layer 622: "On Saturdays the patient spent more time below the range"; and "On Saturdays with total daily insulin between 51-62 Units, the patient spent more time below the range". The parents and siblings layer 622 determines which insights are to be prioritized according to some hierarchy. For example, insights having the following structure can be identified by the parents and siblings layer 622 as a child insight: Type+FeatureA+FeatureB+Outcome. For each insight having this structure, the parents and siblings layer 622 checks for parent insights having the structure: Type+FeatureA+Outcome; or Type+FeatureB+Outcome. Parent insights are sent to the next layer of the delivery layer 606, and child insights are sent back to the insight reservoir 604. If a child insight does not have a corresponding parent insight, then that child insight is sent to the next layer in the stack.

The conflicting outcome check layer 624 handles the presence of insights having conflicting outcomes. The conflicting outcome check layer 624 can check for internal conflicts and/or external conflicts. Internal conflicts can happen only between the insights that reside in the current layer; external conflicts can happen only between the insights in the current layer and the delivered insights. For internal conflicts, the conflicting outcome check layer 624 filters out insights with conflicting outcomes by comparing the first insight (N1) against all of the remaining insights, one by one. If the outcome time horizon of the two insights being compared against one another overlaps by more than a designated amount of time (such as two hours), then appropriate action is taken to resolve the potential conflict. If not, then a conflict is not declared and the candidate insight messages are passed on. If the action requires N1 to be sent to the insight reservoir 604, then further comparisons with N1 are halted and the next insight (N2) is compared against the other insights, as described above. After all of the comparisons are made, the "non-conflicting" insights are sent to the next layer in the stack.

For the embodiment presented herein, the conflicting outcome check layer 624 resolves internal conflicts in accordance with a predetermined methodology. In this regard, FIG. 11 and FIG. 12 together form an exemplary lookup table 644 suitable for use in resolving internal conflicting glycemic outcomes. The lookup table 644 summarizes the manner in which internal conflicts are resolved. The lookup table 644 includes three columns, labeled Spear, Shield, and Action. The items listed in the Spear column represent a selected insight message to be compared against the remaining insight messages (the selected insight message is the "Spear" in this context). In contrast, the items listed in the Shield column represent the remaining insight messages to which the Spear is compared. Each item listed in the Action column represents the action taken by the conflicting outcome check layer 624 when faced with a particular Spear/Shield combination. For example, the combination of "Has severe hyper" and "Has severe hypo" (see the entry 646 in FIG. 11) results in the following Action: "Send Spear to remaining insights". As another example, the combination of "Time in control better" and "Control in range above eighty" (see the entry 648 in FIG. 12) results in the following Action: "Keep both". Note that the lookup table 644 includes a list of all possible combinations; if the Spear is identical to the Shield, then there is no conflict.

For external conflicts, the conflicting outcome check layer 624 filters out insights that conflict within an overlapped window by fetching all insights delivered within the last six hours (or any desired window of time). In this regard, the insights can be fetched from a delivered insights database 654 (see FIG. 10). Each insight from the previous layer is compared against the fetched insights. If the outcome time horizon of the two insights being compared against one another overlaps by more than a designated amount of time (such as two hours), then appropriate action is taken to resolve the potential conflict. If not, then no conflict is declared and the candidate insight messages are passed on.

For the embodiment presented herein, the conflicting outcome check layer 624 resolves external conflicts in accordance with a predetermined methodology. In this regard, FIG. 13 and FIG. 14 together form an exemplary lookup table 658 suitable for use in resolving external conflicting glycemic outcomes. The lookup table 658 summarizes the manner in which external conflicts are resolved. The lookup table 658 includes three columns, labeled Spear, Delivered, and Action. The items listed in the Spear column represent a selected insight message to be compared against the Delivered insight messages (the selected insight message is the "Spear" in this context). In contrast, the items listed in the Delivered column represent the insight messages to which the Spear is compared. Each item listed in the Action column represents the Action taken by the conflicting outcome check layer 624 when faced with a particular Spear/Delivered combination. For example, the combination of "Has hyper" and "Has hypo" (see the entry 660 in FIG. 13) results in the following Action: "Send Spear to remaining insights". As another example, the combination of "Time in hyper worse" and "Has severe hypo" (see the entry 662 in FIG. 14) results in the following Action: "Send Spear to the next layer". Note that the lookup table 658 includes a list of all possible combinations; if the Spear is identical to the Delivered insight message, then there is no conflict.

As mentioned above, the user related layers of the delivery layer 606 include the user feedback layer 626 and the user fatigue layer 628. The user related layers are associated with user interaction and the gathering of user feedback on previously delivered insight messages. For example, the user feedback layer 626 allows the insight delivery engine to accommodate user preferences. The user feedback layer 626 adjusts or otherwise influences the delivery of insights based on historical feedback obtained from the users. As shown in FIG. 10, a user feedback database 666 obtains user feedback data 668 from a user device 670 (e.g., the patient's mobile device). The user feedback database 666 is considered to be an external source from the perspective of the delivery layer 606. The user feedback layer 626 considers the insight type, insight event combination, and outcome and finds a matching insight type in the user feedback database 666. Next, the user feedback layer 626 fetches the last three values in the "preference" field (i.e., whether the user liked or disliked the insight) and takes appropriate action. For example, if all three preference values are "dislike", then the insight under review is discarded, otherwise, the insight is sent to the next layer.

The user feedback database 666 maintains multiple tables, wherein each table corresponds to one type of insight. A table is updated every time the user provides feedback regarding an insight that was delivered. Each table in the user feedback database 666 has three primary fields: Timestamp; Preference; and Delivery Curve. The Timestamp field indicates the time when the user provided feedback. The Preference field indicates the content of the feedback, e.g., "like" or "dislike". The Delivery Curve field indicates a dynamic state (A, B, or C for this particular embodiment) as determined by the preference data. The Delivery Curve status for a given insight can dynamically change as the user provides feedback. The exemplary embodiment described here updates the Delivery Curve status according to the following update logic: (1) if the current Delivery Curve is A, then a new "dislike" from the user changes the Delivery Curve to B; (2) if the current Delivery Curve is A, then a new "like" from the user results in no change to the Delivery Curve; (3) if the current Delivery Curve is B, then a new "dislike" from the user changes the Delivery Curve to C; (4) if the current Delivery Curve is B, then a new "like" from the user changes the Delivery Curve to A; (5) if the current Delivery Curve is C, then a new "dislike" from the user results in no change to the Delivery Curve; (6) if the current Delivery Curve is C, then a new "like" from the user changes the Delivery Curve to B.

The user fatigue layer 628 contemplates potential user fatigue, wherein users may grow tired or inattentive if they receive the same insight message too often. The user fatigue layer 628 regulates the delivery of certain insight messages, such that they are not repeatedly delivered too frequently. More specifically, the user fatigue layer 628 queries the user feedback database 666 to obtain the applicable Delivery Curve for the insight message, and uses the current time to compute the number of days since the patient began using the system (e.g., how long the patient has been using the mobile app on the patient's user device 670). The Delivery Curve and the number of days are used to determine the time interval for delivery of the insight message. Next, the delivered insights database 654 is queried to obtain the last delivery time (Ta), which is used to compute the time elapsed since the last delivery of the insight message. More particularly, the lapsed time is calculated as the difference between the current time and the last delivery time (Ta). If the lapsed time is greater than or equal to the determined time interval for delivery, then the insight message is sent to the next layer, otherwise, it is designated as a remaining insight 612 and is sent to the insight reservoir 604. Simply put, the user fatigue layer 628 ensures that a long enough time has passed before resending the same insight message again.

The delivered insights database 654 keeps track of all insight messages that have been sent to the user. The database 654 is updated whenever an insight message is delivered to the user. In certain embodiments, each insight message that is delivered can be identified by a unique identifier, code, or string. The delivered insights database 654 can also record a timestamp for each delivered insight, and record a global insight index.

As mentioned above, the delivery layer 606 employs three delivery curves that influence the timing of insight message delivery. Delivery Curve A is the default active delivery curve that is used when the user starts to use the system. Every time the user provides feedback on an insight message, the system checks whether to change the active delivery curve in the manner described in more detail above. Although the specific formula utilized for each delivery curve may vary from one embodiment to another, the following delivery curves are used in the exemplary embodiment described here:

$$\text{Delivery Curve } A: y = 40 \times \frac{x^{0.75}}{(500 + x)^{0.75}}$$

$$\text{Delivery Curve } B: y = 40 \times \frac{x^{0.75}}{(80 + x)^{0.75}}$$

$$\text{Delivery Curve } C: y = 40 \times \frac{x^{0.75}}{(30 + x)^{0.75}}$$

Figure 15:
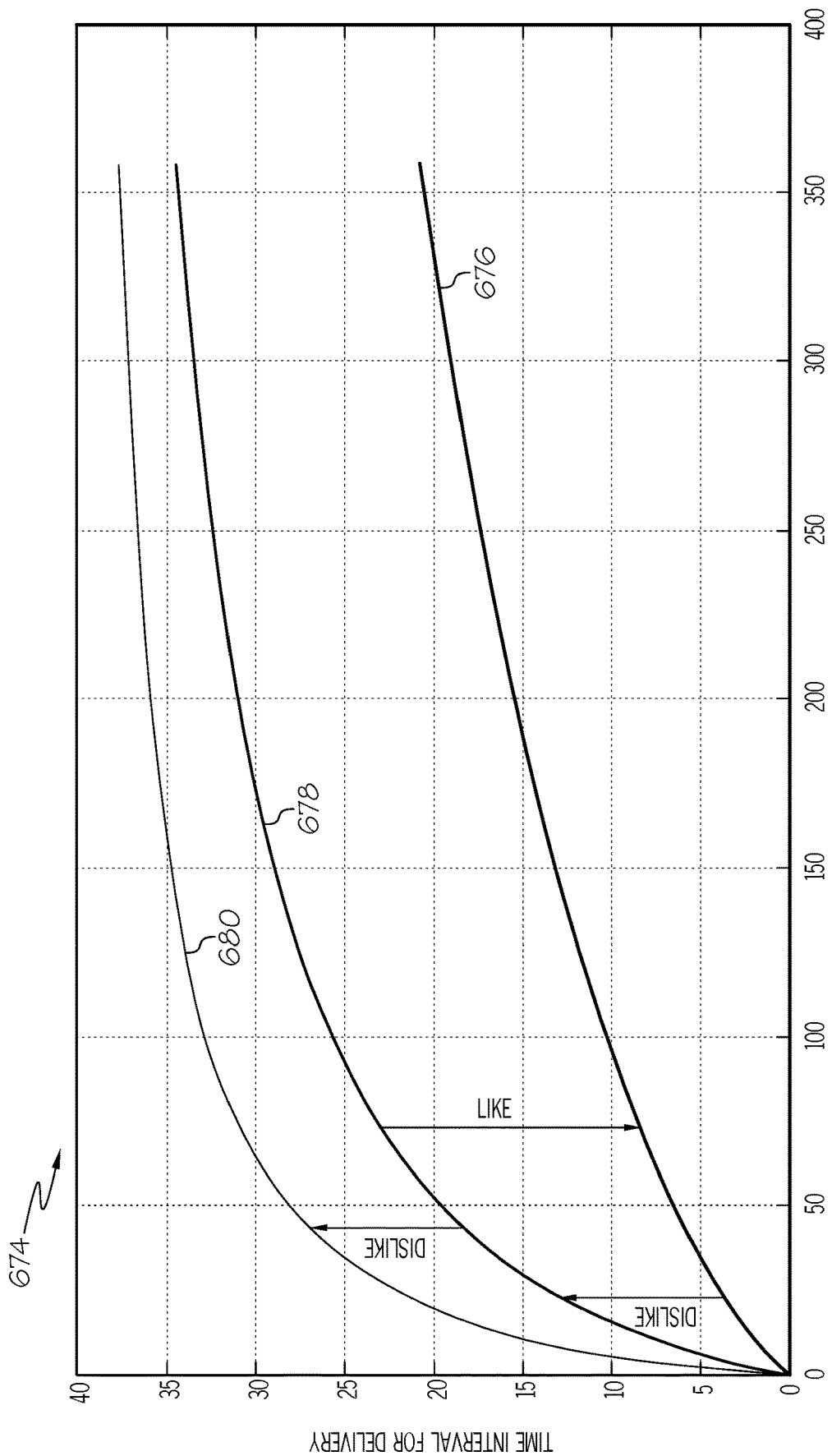
FIG. 15 is a graph that depicts delivery curves that influence insight message delivery timing.

FIG. 15 is a graph 674 that depicts delivery curves that influence insight message delivery timing. The y-axis corresponds to the time interval for delivery of an insight message, and the x-axis corresponds to the number of days that the user has been using the system (e.g., using the mobile app). The graph 674 includes a plot 676 corresponding to Delivery Curve A, a plot 678 corresponding to Delivery Curve B, and a plot 680 corresponding to Delivery Curve C. The vertical arrows in the graph 674 show how the system transitions between delivery curves, depending on whether the user provides "like" or "dislike" feedback on insight messages that have been delivered.

As mentioned above, the weight based layers include a customized insights layer 630, an advanced insights layer 632, and an outcome based layer 634. These weight based layers prioritize the insight messages based on certain defined preferences, criteria, and factors (e.g., some insight messages are deemed more important than others and, therefore, are "weighted" or prioritized accordingly). Thus, insight messages with severe hypoglycemia and severe hyperglycemia outcomes are treated with special priority to bypass this group of layers. The bypass path 682 schematically shows how these special types of insight messages are delivered in a prioritized manner by default. The other insight messages (obtained from the upper/previous layer) are prioritized by desired criteria, and are then delivered to the user in a manner that is limited by a threshold set in the accumulator layer 618. For the embodiment presented here, the threshold corresponds to three insight messages (not including severe hypoglycemia and severe hyperglycemia insights) per 24 hours. Thus, the accumulator layer 618 keeps count of the number of delivered insights. If more than three have accumulated, then the excess can be moved back to the reservoir 604 for the next iteration.

The customized insights layer 630 supports user-entered changes in the prioritization scheme applied to certain categories of glycemic insights. In other words, the customized insights layer 630 can be utilized to prioritize the insight message delivery according to user preferences. In practice, the customized insights layer 630 uses a variable to identify the type, category, or class of each insight message (e.g., an identifier, a code, a string tag, or the like). The customized insights layer 630 queries an app settings database 684 to obtain the user's preferred or customized list of prioritized insight messages. If the identifying variable of the insight message of interest is found in the user's list, then the customized insights layer 630 prioritizes the insight message in the delivery queue. Otherwise, the insight message is handled as usual and is passed to the next layer in the stack.

The advanced insights layer 632 is deployed to handle certain types of insights that are linked to user behavior. For example, if a given user frequently changes her insulin pump settings, then the advanced insight layer 632 contemplates that behavior to influence the delivery of insight messages. In other words, the advanced insights layer 632 can be utilized to prioritize the insight message delivery in accordance with the user's behavior. For example, if the patient has recently changed the basal rate, then the system assumes that the patient will be interested in glycemic insight messages that are related to basal rate and adjusts the priority of such insight messages. In practice, the advanced insights layer 632 uses a variable (e.g., an identifier, a code, a string tag, or the like). The advanced insights layer 632 also considers the changes to certain infusion device settings, such as: basal setting; carbohydrate ratio (CR) setting; and threshold suspension setting, which relates to suspension of basal insulin delivery if low blood glucose is observed (the threshold suspension setting refers to programmed values of the glucose threshold and time period for suspending delivery).

For this particular example, there are four types of advanced tags (which are all strings): Basal Setting; CR Setting; ISF Setting; and threshold suspension (TS) Setting. If the insight message can be associated with any of them, then one of the advanced tag strings will be assigned to the advanced tag variable for that particular insight message. For example, if there is an insight message referring to a threshold suspension event, the system knows that it can be linked to the TS pump setting, therefore "TS setting" is assigned as the advanced tag. In practice, there can be a considerable amount of insight messages that cannot be associated with any of the four types of advanced tag settings; these are not labeled as "advanced" insight messages. In real time, the system keeps checking the user behavior for purposes of prioritization. Thus, if the system determines that the user changes the basal setting often, it can prioritize insight messages with the advanced tag equal to "Basal Setting" in the advanced insights layer 632.

The outcome based layer 634 is used to prioritize insight messages related to hypoglycemia outcomes higher than insight messages related to hyperglycemia outcomes. Thus, the system can prioritize the insight messages in accordance with their respective glycemic outcomes. For this particular example, the outcome based layer 634 prioritizes certain insight messages in accordance with a predetermined sequence or order that reflects the typical level of importance of the associated outcomes. The specific prioritization scheme may vary from one embodiment to another. That said, the exemplary embodiment utilizes the following prioritization scheme: has hypo>time in hypo worse>time in hyper worse>time in control better>control in range above eighty percent>has hyper. In accordance with this scheme, the outcome "has hypo" has the highest relative priority, and the outcome "has hyper" has the lowest relative priority. Insight messages having outcomes that are not contemplated by the prioritization scheme will not be affected by the outcome based layer 634.

The accumulator layer 618 represents the last layer in the stack of the delivery layer 606. The accumulator layer 618 imposes an upper bound on the total number of insight messages delivered over a designated period of time, such as the last 24 hours. For the exemplary embodiment presented here, the accumulator layer 618 limits insight message delivery to a maximum of three for any 24 hour period. The accumulator layer 618 sends insight messages to the user device 670 based on the queue from the previous layer, and accumulates the number of delivered insight messages for the last 24 hours. Once the total reaches the limit (which is only three for this example), any other insight messages in the queue are designated as remaining insights 612, and are sent back to the insight reservoir 604.

Glycemic Insights—Additional Features and Functions

The quantification and delivery of personalized information on the most frequent and impactful therapy behaviors on glycemic control can be applied to more than a patient focused mobile application or a web-based platform. For example, the quantification process can be expanded beyond glycemic control to the effect of therapy behaviors on the quality of life, or other medical comorbidities, etc. In other words, the "outcomes" considered by the system 100, 300 can be extended beyond those normally associated with diabetes, e.g., the patient's emotional state; the patient's energy level; neurological conditions; cardiac symptoms; or kidney conditions. As another example, the optimized time of delivery of insight messages as determined through machine learning techniques can also be expanded to determine the best way (wording of messaging, look of the message, arrangement of message content, and the like) to convey the message to derive the most benefit to the patient. As another example, the delivery platform can be expanded to medical devices tailored to improve therapy related behaviors such as an insulin pump or other medication adherence applications. Although the exemplary embodiments described herein concentrate on the delivery of insight messages to patients, the insight messages can also be provided to healthcare providers, clinics, care partners, and other recipients as needed in order to optimize the communication within a patient's care team. Moreover, aggregated analyses from anonymized glycemic insights can also be used to adapt future models of glycemic insights and explore the optimization of delivery, end-user selection, delivery platforms, etc.

Retrospective Insights for Patient Engagement and Wellbeing

Managing diabetes for patients with the disease can be an all-encompassing effort with the primary goal of improving the quality of life, reducing complications, and improving glycemic control. The intelligently generated insight messages (as described above) correlate behaviors to glycemic outcomes in a predictive or retrospective fashion. Other forms of analytics and messaging can improve patient engagement, education of disease state, and best practices in disease management (adherence measures), especially when delivered to patients through a mobile application or web-based service platform.

Conventional reporting mechanisms do not always deliver notifications and messages intelligently at a time most suitable for the users' maximal awareness. Accordingly, certain embodiments employ a personalized diabetes management assistant system that utilizes the information from various sources to identify the associations to typical diabetes management behaviors and emotions to improve patient engagement and wellbeing. This system can be implemented on various computing platforms (computers, smartphones, tablets, and the like). The goal is to optimize patient engagement, motivation, and wellbeing during diabetes management by identifying and rewarding patterns associated with best disease management practices, providing positive reinforcement, and providing helpful educational tips and reminders, etc., while not increasing the daily management burden.

The baseline methodologies described above can be utilized to generate and deliver insight messages that are intended to encourage, reward, motivate, or congratulate the patient, or to otherwise provide positive reinforcement in a timely and meaningful manner. Insight messages of this type can include, without limitation: motivational insight messages; adherence insight messages; and reminder insight messages.

Motivational insight messages can be triggered by certain conditions, such as: longer periods of time within the patient's target glucose range; shorter periods of hypoglycemia; shorter periods of hyperglycemia; fewer hypoglycemic episodes; or fewer hyperglycemic episodes. Examples of appropriate motivational insight messages include the following, without limitation:

"On average you spent 15 hours per day in your target glucose range last month. During the last seven days, you spent 18 hours per day in your target glucose range. Well done!"

"Great job! You had no low glucose episodes this week!"

"Keep it up! This month you spent 10% less time in a high glucose state compared to last month."

"On average, you spend 50 minutes per night in your low glucose range. This week, however, you only spent ten minutes per night in your low glucose range. Way to go!"

"Superb! You had no low glucose episodes after lunch this week!"

"Congratulations! This month you received 10% fewer high glucose alerts compared to last month."

Adherence insight messages can be triggered by certain conditions, states, or requirements. For example, an adherence insight message can be associated with any of the following, without limitation: infusion set change; frequency of blood glucose meter readings; glucose sensor usage; bolus calculator usage; or dual wave bolus usage. Examples of appropriate adherence insight messages include the following, without limitation:

"In the last 30 days, an infusion site change was found every five days on average. Consider changing the frequency more often to meet labelled goals."

"In the last week, we found only two blood glucose measurements per day. Consider checking it more frequently to increase glucose awareness."

"In the last 30 days, glucose sensor wear was detected on 12 days. Consider wearing the sensor more often to increase glucose awareness."

"In the last 30 days, your bolus calculator was not used for 25% of the detected boluses. Consider using the bolus calculator more often to optimize bolus dosages."

Reminder insight messages can be triggered by certain conditions, states, or requirements. For example, a reminder insight message can be associated with any of the following, without limitation: infusion set change; meal entries; blood glucose meter readings; or glucose sensor usage. Examples of appropriate reminder insight messages include the following, without limitation:

"Reminder: it has been four days since your last infusion set change."

"Reminder: it looks like you had a bolus. What's for breakfast?"

"Reminder: it has been six hours since your last blood glucose measurement. Plan for a new measurement soon."

"In the last 30 days, a dual wave bolus was not used. Consider using a dual wave bolus for meals with high fat content."

The manner in which the motivational, adherence, and reminder insight messages are triggered, generated, queued, and delivered can be consistent with that described in more detail above. Accordingly, the associated triggering mechanisms, input data types, insight generation methodologies, and insight delivery methodologies will not be redundantly described here.

Automatic Patient Therapy Reminders

Diabetes therapy management requires patients to consider meal content, daily exercise, sickness, stress, and medication regimen. Moreover, patients must follow a number of guidelines to optimize their therapies on an insulin pump. In this regard, there are a number of recommended behavioral checks and therapy checks that patients and health care providers can assess before adjusting or changing settings of an insulin infusion pump. Behavioral checks can include any of the following, without limitation:

Are there three or more boluses per day?
Are there four or more blood glucose measurements per day?
Is the onboard bolus calculator feature being used?
Is the infusion set being changed every two to three days?
Is the pump suspended less than one hour per day?
Does the patient use a temporary basal rate for exercise?
Does the patient initiate a bolus before meals?
Is the patient disconnecting appropriately?

Therapy checks can include any of the following, without limitation:

Verify pump settings
Verify that the basal percent is less than 50% of the total daily dose (TDD)
Evaluate overnight control (basal)
Evaluate pre-meal control (basal)
Evaluate post-meal control (carbohydrate ratio)
Does the patient experience significant excursions?

In order to ease the burden of constantly remembering the recommendations listed above and/or other recommendations, insight messages (as described above) can be generated and delivered to the patient's mobile device at an appropriate time. For example, an easily accessible message delivered to a smartphone, computer, tablet, or other device can provide appropriate time based or outcome based notifications related to: adherence measures and pumping protocols; patient, health care provider, and care provider reminders; and adherence measures that have historically resulted in poor glycemic control.

The baseline methodologies described above can be utilized to generate and deliver timely insight messages to remind the patient that it is time to perform a behavior for best practices in diabetes therapy management. Such reminder messages can be triggered following a countdown of time since the last auto-detected behavior of interest, or following a prevalence of poor glycemic outcomes and associated time since the last auto-detected behavior of interest. In certain embodiments, a reminder can be delivered to the patient at a predetermined stopwatch time countdown, or when intelligently associated with poor glycemic outcomes as guided by the pumping protocol best practices. Reminder guidance may be obtained from healthcare providers, academic medical literature, or other respected sources of medical information.

As one example, a reminder message can be generated and delivered to the patient's mobile device to let the patient know that it is time to change the infusion set, wherein the reminder message is triggered following a countdown of three days after the last auto-detected pump rewind action (which indicates the installation of a new insulin reservoir). As another example, a reminder message can be generated and delivered to the patient's mobile device to let the patient know that it is time to change the infusion set, wherein the reminder message is triggered following a prevalence of hyperglycemia and a lack of pump rewind in the last three days.

The manner in which these reminder insight messages are triggered, generated, queued, and delivered can be consistent with that described in more detail above. Accordingly, the associated triggering mechanisms, input data types, insight generation methodologies, and insight delivery methodologies will not be redundantly described here.

Adherence Reports

In accordance with certain embodiments, patient-specific data can be used to generate personalized adherence reports, which can be generated and delivered as a type of insight message to the patient's smartphone, computer, tablet, or mobile device. An exemplary adherence report may contain reminders, recommendations, and checks as described in the previous section titled Automatic Patient Therapy Reminders. In order to ease the burden of constantly remembering recommendations related to insulin therapy and infusion system use, an adherence report can document the relevant guidelines for patient adherence (and provide active links to educational recommendations). The adherence report may also include a comparison of the patient's behaviors, as reflected by the captured and analyzed personal data, to recommended ranges of behaviors. Adherence reports can be delivered in a timely manner as chosen by the patient and/or as determined by the insights delivery methodology, to allow the patient to conveniently review the recommended behaviors and their personal standing. An adherence report can be delivered to the patient as a static page or notification, or as a dynamically searchable graphical user interface having an interactive menu with links to educational materials associated with the adherence recommendation.

An adherence report may indicate certain ranges of recommended behaviors, as provided by the pumping protocol. The content of an adherence report may also be expanded to include customized adherence recommendations from healthcare providers, approved medical literature, and/or other established guidelines for diabetes therapy management.

Moreover, adherence reminders/reports can be tailored or customized as needed for stricter guidelines. For example, stricter guidelines are typically recommended for pregnant patients and for cases of gestational diabetes. The adherence reminders/reports can also be tailored or customized to contemplate post-hospital discharge periods, where the path to recovery may include looser guidelines.

Glucose Assist System

Referring again to FIG. 1, the system 100 may also be suitably configured to support an intelligent and enhanced approach for providing and reporting glucose-related information to the patient. In this regard, the same mobile app (residing on the patient's mobile device 104) that supports the delivery of glycemic insight messages can be utilized to support the exemplary glucose assist system described in more detail below. Some or all of the input data described above in the context of the system 100, 300 can also be leveraged by the glucose assist system presented here. The glucose assist system processes much of the same input data to provide decision support using glucose responses to events that potentially impact the patient's glucose levels. In contrast to the glycemic insights delivery system, the glucose assist system focuses on sensor glucose data, meal and nutrition information, and possibly other input data that might influence the patient's glucose level.

Glucose Assist System Overview

Many processes and behaviors impact blood glucose levels. Commonly recognized processes impacting blood glucose levels include food, exercise, disease (acute or chronic), medication (insulin, oral, etc.), stress patterns, sleep patterns, and the like. Furthermore, behavioral factors such as the time of the day, attentiveness to therapy, purchasing patterns, and other patient behaviors can provide additional quantitative indications of the underlying factors impacting glucose control. Current reports available to diabetes patients and their caregivers do not provide comprehensive results of the aggregated events of interest. One desired goal of the glucose assist system is to provide better, more relevant, and more practical information and guidance to the patient regarding glucose control. Rather than a simple piece of information such as "your glucose will be going low (or high) in the next three hours", the glucose assist system can provide additional information that links glucose data to the occurrence of other events, additional data, and various inputs that are collected by the system. As one specific example, the glucose assist system can predict the patient's glucose response after the patient eats a cheeseburger, takes a bolus, and exercises by contemplating a variety of event-specific and patient-specific data. In accordance with certain scenarios, the glucose assist system can generate animated output, such as animated glucose traces that are animated in the order of retrospective responses to an event followed by projections into future traces based on optimized settings.

As used herein, a "glycemic response curve" refers to a continuous glucose sensor output for a designated period of time following a particular event (see below for a list of potential events of interest, such as meal time, yoga workout, and metformin ingestion). This response curve can also be extended to include blood glucose values from a blood glucose meter, e.g., a finger stick measurement device.

Results of the event response segregation are aimed to optimize medication and therapy regimen in the form of personalized decision support. The glucose assist system provides methods and weights to optimal and suboptimal therapy changes per outcomes.

The functionality of the glucose assist system can be implemented as a mobile app, a software program, or an executable module on various computing and electronic device platforms (computers, smartphones, tablet computers, portable medical devices, smart wearables, and the like) to educate patients on historical glycemic patterns. The personal glucose assist system may also be fine-tuned to the outcomes and/or behaviors that the patients and healthcare professionals deem the most important for that individual's stage of diabetes management. These prioritizations can be captured based on explicit and implicit feedback from the computing platform.

Data Inputs and Model Feature Sets

The glucose assist system considers a number of glycemic response events that may have some relationship to the patient's glucose response and/or glucose management scheme. A glycemic response event can be conveyed in, identified by, or otherwise associated with input data obtained for the patient. Although the number and type of data inputs can vary from one embodiment to another, the exemplary embodiment considers the following, without limitation: (1) meal time and nutritional content; (2) exercise time, type, and intensity; (3) medication type, dosage, dosage time; (4) sleep time and quality; (5) stress time (based on physiological factors such as heart rate, blood pressure, skin conductance, or user input); (6) time of day and/or day of week (weekday vs weekend); (7) carbohydrate amount; (8) bolus dosage amount (in Units), time of bolus (time and/or calendar data), and bolus type (normal, square, dual); (9) active insulin amount; (10) basal rate of insulin; (11) temporary basal use; (12) consecutive boluses; (13) insulin suspension or infusion pump suspend mode; (14) insulin reservoir rewind and priming time; (15) insulin pump alarms and alarm times; (16) sensor alerts and alert times.

Methodologies

The sensor glucose and bolus data following a specific set of events can be displayed as-is for a default or current scale (mg/dL or mmol/L), or the data can be transformed into a z-score (x-mean/standard deviation) in order to normalize the trace for an individual. Glucose outcomes for the events are evaluated within the retrospective data. Instances leading to the best glucose outcomes are recognized and displayed to the user. Evaluation of the outcomes can be performed by machine learning algorithms, such as feature selection by maximum likelihood estimation via regression analysis, neural networks, support vector machines, logistic regression, decision trees, and the like. Regardless of the particular implementation, the glucose assist system can define feature importance and optimal glycemic response events.

This multivariate combination of independent variables is also useful to iterate through a combination of simultaneously occurring events. An extension of this concept relates to a combination of ingredients in a meal. This level of detail in a model can extract the ranges of medication, behaviors, or ingredients that can result in the optimal outcome for the patient based on historical data. Moreover, the system can use the model to predict the ranges of events that may not have occurred yet, but might result in optimal outcomes.

The specific methodology employed by the glucose assist system to calculate the patient's glucose profile can vary from one implementation to another, as appropriate for the particular embodiment. The following examples relate to different methods that can be used to evaluate the resulting sensor glucose data in connection with a particular food or action in the presence of additional covariates. It should be appreciated that additional or alternative techniques can be deployed by an embodiment of the glucose assist system.

Method 1: Independent Components Analysis for Single Food Glucose Response

Independent components analysis (ICA) can be used to denoise a signal, or extract source data from linear combinations of multiple concurrent signals. See, for example, the approach that is published online at www.wikipedia.org, and the approach described in Independent Component Analysis: A Tutorial, by Hyvarinen and Oja (April 1999), the content of which is incorporated by reference herein. Current applications of ICA include voice recognition by identifying the speech of individuals in a room of talking people. In the same way that a particular voice may be detected in a room with multiple speakers, a person's glucose profile associated with eating a peach can be separated from the glucose profile associated with eating yogurt (assuming that person ate a peach parfait with peaches and yogurt as the primary ingredients). ICA assumes that the inputs, however, are linearly independent, and this assumption may not always be accurate in the context of human metabolism.

Thus, if the patient eats a cheeseburger, the system can identify and isolate the glucose profile impact of the individual ingredients (or at least the primary ingredients that have a significant effect on the glucose profile). In certain embodiments, the system relies on user-entered data that indicates the food that was (or will be) consumed, and perhaps the main ingredients of that food. Thus, the system can generate a predicted glucose plot corresponding to each individual ingredient, which in turn allows the system or the patient to identify any potentially troublesome ingredient, i.e., an ingredient that causes an undesirable change in the patient's glucose profile. As an extension of this concept, the system can be suitably configured to individually consider the nutritional content of consumed food rather than the specific ingredients. In this regard, the system can break down the consumed food by the amount of fat consumed, the amount of simple carbohydrates consumed, the amount of complex carbohydrates consumed, and the amount of protein consumed, and generate corresponding glucose response plots for those individual components.

Method 2: Principal Component Analysis and Sensor Trace Categorization for Food Glucose Response Surrogate from Macronutrient Composition Principal Component Analysis (PCA) is a statistical procedure that uses an orthogonal transformation to convert a set of observations of possibly correlated variables into a set of values of linearly uncorrelated variables called principal components. In this regard, another way to predict glucose responses to combinations of concurrent inputs is to characterize sensor glucose data by clusters identified by minimization of the Mahanolobis distance of the centroid from the first three principal components of the sensor glucose data. Once the glucose sensor data has been categorized (for example, into five clusters), the cluster category can be used as the independent variable to the dependent variables associated with each sensor glucose trace. In this case, the dependent variables could be carbohydrate amount, fat amount, protein amount, and calorie amount aggregated from a single meal, as well as the amount of insulin taken at the meal, the starting sensor glucose value and the sensor glucose rate of change for 30 minutes before the meal. From these combinations of inputs, the model can be trained to predict a resulting glucose response curve. The relationship to meal content for deployment into the mobile app can occur by applying the meal macronutrients to a particular food item (with the details of the insulin and sensor glucose) and displaying the resulting predicted sensor glucose trace as calculated by the average of all of the traces that form the categorized cluster.

Method 3: Machine Learning for Optimal Insulin Administration Per Meal Content to Result in Best Outcome (Time in Range)

This methodology predicts a time range during which the patient's glucose will be within a designated target range of values. This type of feedback can be useful to the patient because one desired goal is to maximize the time period during which the patient's glucose is well controlled. Thus, if the user indicates that she wants to eat ice cream, the system calculates the desired portion size, the best time to eat the ice cream, the bolus dosage, the best time to administer the bolus, and the like. This information is provided to the patient in an effort to optimize the amount of time that the patient will stay within her target glucose range (assuming that she will actually eat the ice cream and follow the recommendations). The information delivered to the patient goes well beyond a simple warning or a status message.

As an example, using the same dependent variables listed above, the output of the machine learning technique will instead be the percent time in range from 70-180 mg/dL for the four hours following a meal ingestion. From this information, the insulin administration can be altered to ensure that the resulting outcome will be in range. An alternative to this approach may be a binary indication beyond a particular time in range threshold (80%, for example, but the specific percentage can be changed according to the patient's history and control, and can be adapted over time).

These outcomes are available for the user either on demand or displayed to the user intelligently when the system detects a high probability of the event occurrence.

Data Outputs

In accordance with the exemplary embodiment presented here, the output of the glucose analysis provides information to the user in a desired format. The output may include any or all of the following, without limitation: (1) each individual glucose response trace; (2) each individual insulin trace; (3) the average glucose response trace; (4) the average insulin trace; (5) the variation of all response traces; and (6) the best and worst outcomes as determined by the outputs (1)-(5).

Model Result

The model provides the behaviors/medications and dosage ranges necessary to provide the best outcomes as defined by the patient and healthcare provider. This can include the most time within a range, the least time in low blood sugar, the least amount of glycemic variability, and the like. Furthermore, the model provides weights of importance of each feature to the desired (and undesired) outcomes.

Applications and Model Extensions

The glycemic response curve can be used to describe glycemic management patterns in the daily life of patients. Examples of this include, without limitation:

(1) The patient's own physiological response to particular behaviors, medications, events, etc.

(2) The change in the patient's physiological response over time.

(3) It can also be used to inform predictive analytics in the form of a comparative measure on the individual patient level or the aggregated cohort level. For example, comparative responses for medication adjustment, comparative responses for food recommendations, comparative responses for optimal exercise regimen, comparative responses for optimal sleep habits, etc.

(4) These response curves can also be used to perform epidemiological studies of the ranges of glycemic responses to certain stimuli and studied according to particular demographic information such as duration of diabetes, sex, age, race/ethnicity, etc.

(5) Features from the glycemic response curve (the area under the curve, the rate of change, etc.) to food can be used to calculate the glycemic index and glycemic load of a food to an individual.

Graphical Support of the Glucose Assist System

Figure 16:
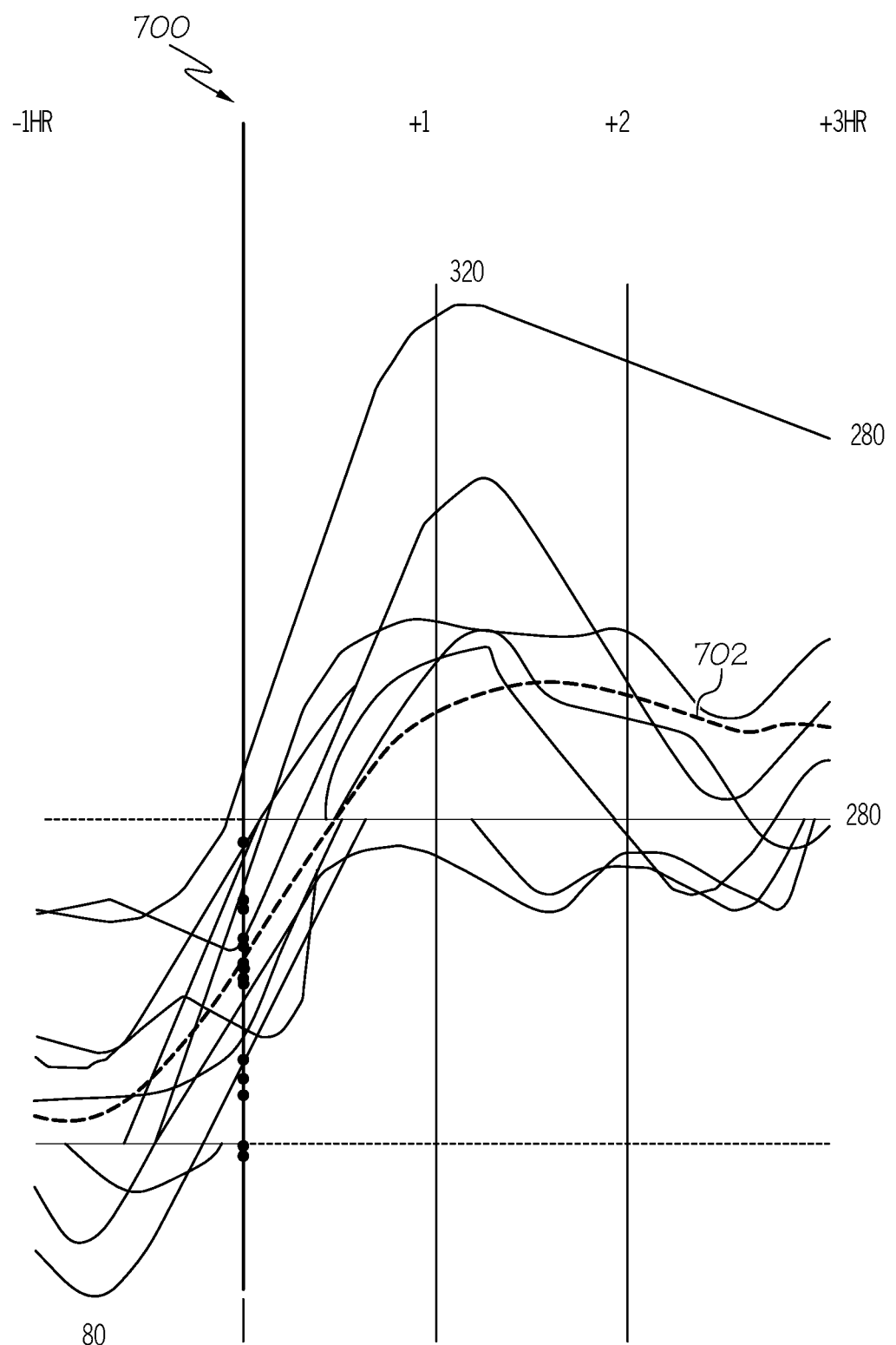
FIG. 16 is an exemplary graph of overlaid glucose sensor traces as tethered to a particular event.

The glucose assist system can generate graphs, plots, and other visual output formatted in a suitable manner. For example, FIG. 16 is an exemplary graph 700 of overlaid glucose sensor traces as tethered to a particular event. The tethered event can be any of the glycemic response events listed above, such as medication time, exercise time, meal time, or the like. The horizontal axis represents time relative to the time of the event under analysis (which corresponds to the origin). The vertical axis represents glucose measurement values. The graph 700 depicts multiple events (for example, the patient takes a yoga class), along with an average plot 702. The average plot 702 indicates the average glucose response for the yoga class event. In addition to the average, additional statistical measurements (such as median, standard deviation, or interquartile range) can also be overlaid.

Figure 17:
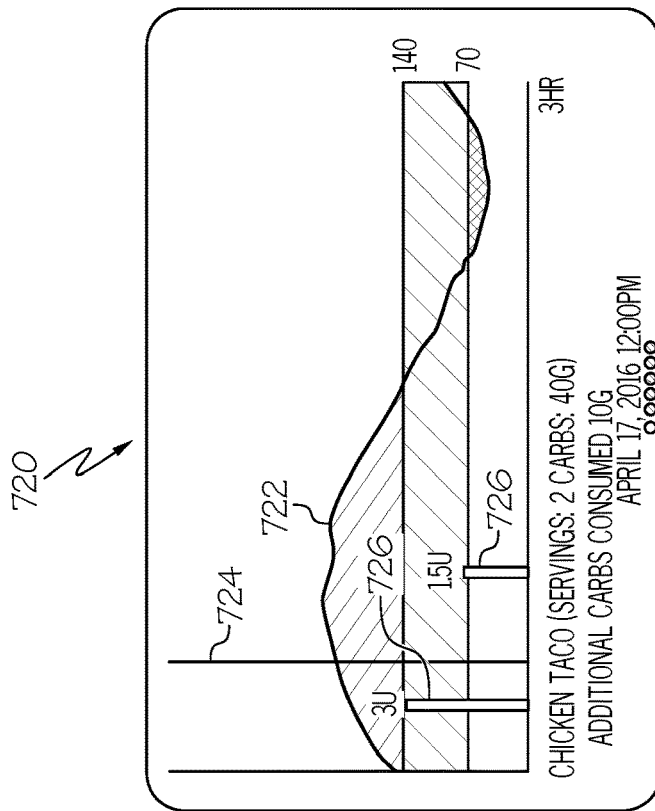
FIG. 17 is an exemplary graph of an individual glucose sensor trace curve surrounding the time of a specific event.

FIG. 17 is an exemplary graph 720 of an individual glucose sensor trace curve surrounding the time of a specific event (eating a chicken taco). The graph 720 includes an individual glucose plot 722 that spans the time surrounding the event, wherein the vertical line 724 corresponds to the event time. The graph 720 also includes graphical indications 726 of the amount of medication (insulin) administered to accommodate the meal. Additional information displayed in the graph 720 includes a timestamp of the event, the serving amount in the consumed meal item, the amount of carbohydrates consumed as part of the meal item, additional carbohydrates consumed with that meal item and the patient's target glucose range for good glycemic control.

Figure 18:
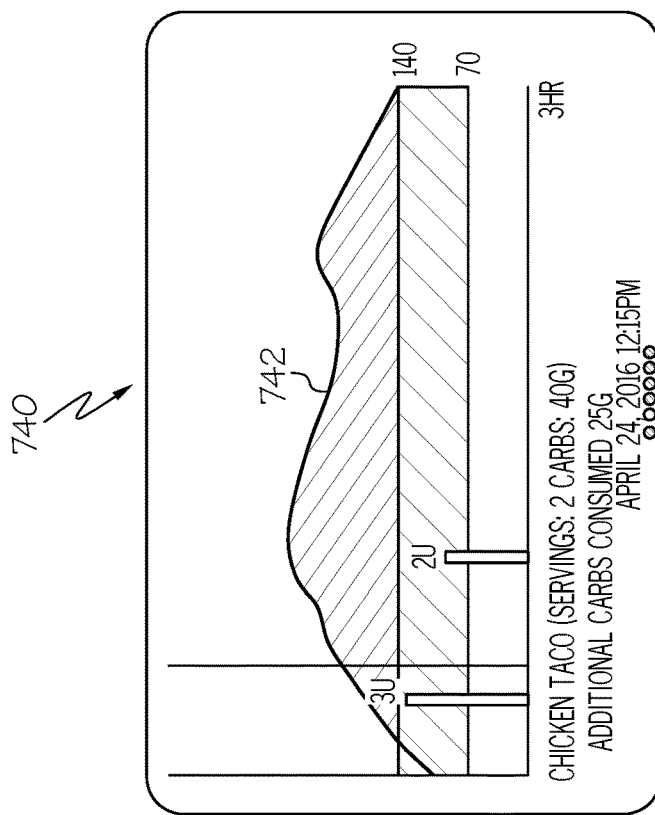
FIG. 18 is another exemplary graph of an individual glucose sensor trace curve surrounding the time of a specific event.

FIG. 18 is another exemplary graph 740 of an individual glucose sensor trace curve surrounding the time of a specific event (eating a chicken taco). The graph 740 is similar to the graph 720 shown in FIG. 17, but the date is different, the amount of additional carbohydrates consumed is 25 grams rather than 10 grams, and the size and timing of the second bolus is different. More specifically, the second bolus is 2.0 Units rather than only 1.5 Units, and the time between the event time and the second bolus is longer in the graph 740, relative to that shown in the graph 720. Notably, these differences result in a noticeably different glucose plot 742.

The type of graphs shown in FIGS. 16-18 (and possibly other visualizations) can be generated and delivered to the patient at any desired time. The output information can be used to better understand the relationship between the patient's glucose response, the type and amount of food consumed, and the size and timing of boluses administered in association with the meal.

Figure 19:
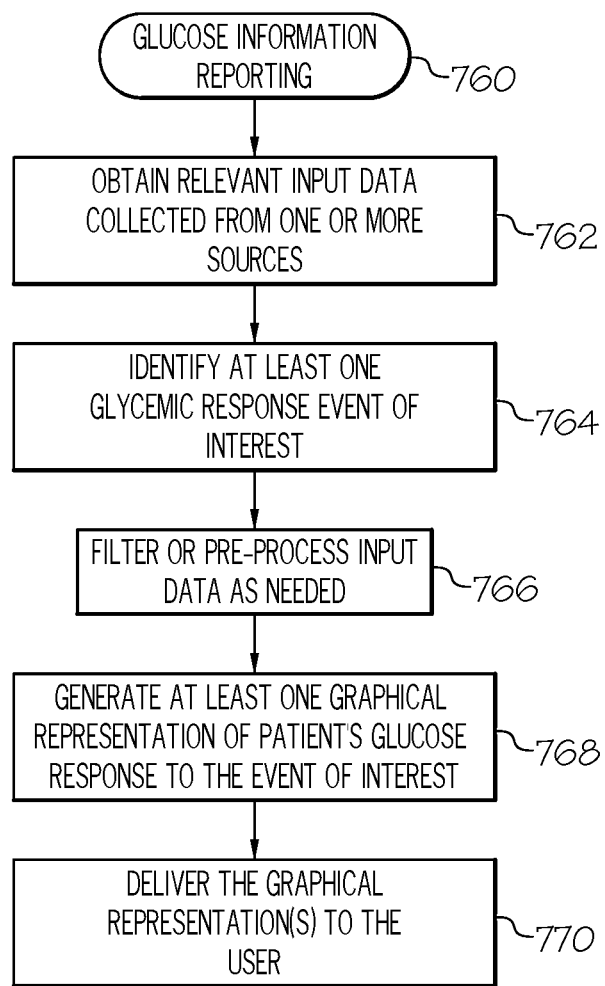
FIG. 19 is a flow chart that illustrates an exemplary embodiment of a glucose information reporting process.

FIG. 19 is a flow chart that illustrates an exemplary embodiment of a glucose information reporting process 760. The process 760 and variations thereof can be performed by the system 100, 300 described above, or by a glucose assist system that is functionally incorporated into the system 100, 300. The process 760 begins by obtaining the relevant input data collected from one or more sources (task 762). As mentioned previously, the glucose assist system preferably utilizes the same input data (historical data) collected for use with the glycemic insight generation and delivery feature. Accordingly, the foregoing description of exemplary input data types and data sources used in connection with the system 100, 300 also applies to the process 760. The process 760 analyzes the input data to provide glucose related information to the user (e.g., actual or predicted glucose plots, which may be based on sensor glucose readings, blood glucose meter measurements, or both). The process 760 also analyzes the input data to provide additional information that can be helpful to the user.

The process 760 identifies at least one glycemic response event of interest (task 764). A number of exemplary glycemic response events were described above, and any of those glycemic response events can be identified at task 764. For ease of understanding, this example assumes that only one glycemic response event has been identified. For instance, the identified glycemic response event might be the ingestion of a meal, physical exercise, or the onset of an illness. Notably, the identified glycemic response event can be associated or otherwise linked to the patient's glucose response profile. Although not always necessary or desirable, the process 760 can filter, condition, or otherwise pre-process the input data or a portion thereof (task 766). For example, task 766 can be performed to identify and remove obviously erroneous or outlier data, to remove "noise" from raw glucose data, and/or to eliminate input data that is unrelated to or has little to no relationship with the identified glycemic response event.

The process 760 continues by generating at least one graphical representation of the patient's glucose response to the identified event of interest (task 768). Consistent with the description of FIGS. 16-18, the graphical representation generated at task 768 can indicate sensor glucose readings and/or blood glucose measurements for the patient. As depicted in FIG. 16, the graphical representation generated at task 768 can include superimposed or overlying glucose plots or traces that correspond to different occurrences of the identified event of interest (the timing of which corresponds to the origin of the horizontal axis). Alternatively, as depicted in FIG. 17 and FIG. 18, the graphical representation generated at task 768 can include only one glucose plot, such as the patient's glucose response following the most recent occurrence of the identified event of interest.

If the identified event of interest includes the ingestion of a meal, a piece of food, a beverage, or something of nutritional value, then the graphical representation generated at task 768 may include a plot/trace that indicates the patient's overall glucose response to the meal, item of food, beverage, etc. Alternatively or additionally, the graphical representation generated at task 768 may include individual plots/traces (rendered in a distinct manner or combined with one another) that indicate the patient's glucose response to the ingredients or nutritional components contained in the ingested meal. In this context, each of the individual plots indicates a constituent glucose response to an ingredient, nutritional component (fat, carbohydrate, protein), chemical composition, or element contained in the meal. For example, if the patient eats a salad, then the graphical representation might include one plot that shows the glucose response attributable to the green vegetation component, another plot that shows the glucose response attributable to the cheese component, and a third plot that shows the glucose response attributable to the dressing component. Methodologies that can be applied to break down the raw glucose data into constituent parts corresponding to the food/nutritional components were described above (e.g., the ICA approach and characterization using Mahanolobis distance).

In certain embodiments, the graphical representation generated at task 768 includes or conveys additional useful information above and beyond the glucose profile data. For example, the graphical representation may include or identify any or all of the following, without limitation: timestamp data for the event of interest; a marker that identifies the timing of the event of interest, e.g., the start time, the end time, or both; an element that indicates the timing and size of an insulin bolus or other amount of insulin administered to accommodate the ingestion of the meal; a descriptor, an icon, or some type of descriptive information regarding the content of the meal, such as text or a label that identifies the particular food, ingredients, or nutritional components (fat, carbohydrates, calories, protein) consumed by the patient; and the like.

The process 760 delivers the generated graphical representation (or more than one if applicable) to the user's mobile device at an appropriate time (task 770). The native processing and display capabilities of the mobile device are used to present the graphical representation to the user.

Figure 20:
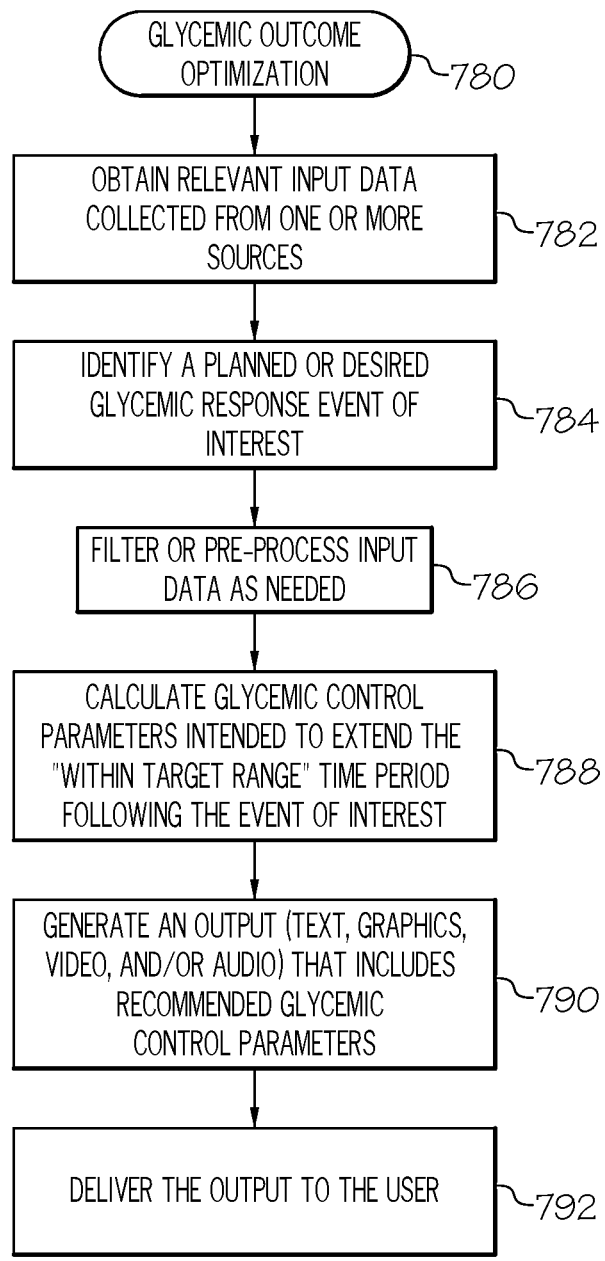
FIG. 20 is a flow chart that illustrates an exemplary embodiment of a glycemic outcome optimization process.

FIG. 20 is a flow chart that illustrates an exemplary embodiment of a glycemic outcome optimization process 780. The process 780 can be considered to be another exemplary embodiment of a method of reporting glucose information for a user of an insulin infusion device. The process 780 and variations thereof can be performed by the system 100, 300 described above, or by a glucose assist system that is functionally incorporated into the system 100, 300. The process 780 begins by obtaining the relevant input data collected from one or more sources (task 782). As mentioned previously, the glucose assist system preferably utilizes the same input data (historical data) collected for use with the glycemic insight generation and delivery feature. Accordingly, the foregoing description of exemplary input data types and data sources used in connection with the system 100, 300 also applies to the process 780. The process 780 analyzes the input data to provide recommendations to the user, wherein the recommendations are intended to extend, maximize, or optimize a period of time during which the patient's glucose is well-controlled.

The process 780 identifies at least one tracked, planned, or desired glycemic response event of interest (task 784). In certain embodiments, task 784 obtains user-entered information that is indicative of the tracked event of interest. A number of exemplary glycemic response events were described above, and any of those glycemic response events can be identified at task 784. For ease of understanding, this example assumes that only one glycemic response event is tracked. For instance, the tracked glycemic response event might be "eating a scoop of ice cream" or "eating two slices of cheese pizza and drinking a pint of beer" or "running for 45 minutes". Although not always necessary or desirable, the process 780 can filter, condition, or otherwise pre-process the input data or a portion thereof (task 786). For example, task 786 can be performed to identify and remove obviously erroneous or outlier data, to remove "noise" from raw glucose data, and/or to eliminate input data that is unrelated to or has little to no relationship with the tracked glycemic response event.

The system analyzes current and historical input data in view of the tracked glycemic response event to calculate one or more recommended glycemic control parameters (task 788). The recommended parameters are intended to extend the "within target glucose range" time period that follows the event of interest, assuming that the tracked glycemic response event will actually occur. In certain embodiments, the system strives to maximize the amount of time that the patient's sensor glucose or blood glucose will remain in the desired target range during the next four hours after the tracked event. The overall time window of four hours is merely exemplary, and the window may be longer or shorter, depending on the particular embodiment. The process 780 calculates the recommended glycemic control parameters with this goal in mind. A glycemic control parameter in this context can be any variable or factor that influences the patient's glycemic response going forward. As used here, the recommended glycemic control parameters may include any of the following, without limitation: information related to ingestion of meals (e.g., the type of food, the portion size, the nutritional content, the ingredients); information related to the timing of meals; information related to insulin delivery (e.g., insulin bolus size, timing of insulin boluses, type of bolus, basal rate); physical activity data; medication data; sleep related data; and the like.

The process 780 continues by generating an output message that includes at least some of the recommended glycemic control parameters, and possibly other information if so desired (task 790). The output can include: a text-based message; graphics; video content; audio content; etc. The output provides tips, guidance, or suggestions for the patient to consider if the tracked event is actually carried out. For example, if the patient plans to eat a scoop of ice cream, then the output may include recommendations related to the portion size, when to eat the ice cream, the insulin bolus size, and when to take the bolus. Thus, rather than providing a simple warning or reminder to the user, the process 780 generates recommendations that, if followed, should optimize the patient's glucose profile for the time period immediately following the tracked event.

The process 780 delivers the output message to the user device in an appropriate format, at an appropriate time, and using a suitable delivery mechanism (task 792). In certain situations, the output message is delivered at a time prior to an occurrence of the tracked glycemic response event. This is desirable to allow the patient to take appropriate action to address the tracked event. The native processing and display capabilities of the user device are used to present the output message to the user.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A computer-implemented method of managing use of an insulin infusion device, the method comprising:
   obtaining, at a cloud-based computer-implemented server system, input data for a user of the insulin infusion device;
   comparing, with the server system, the input data against historical event/outcome combinations maintained for the user, each of the event/outcome combinations comprising insight event data indicative of a respective glycemic event and a respective glycemic outcome corresponding to the insight event data;
   determining, based on the comparing, a correlation between the input data and a particular glycemic outcome, the determining step performed by the server system, wherein the determining step comprises:
      analyzing the historical event/outcome combinations to count a number of times that an insight event has occurred in a designated historical window of time;
      comparing the number of times to a predetermined threshold number; and
      confirming that insight generation criteria is satisfied only when the number of times exceeds the predetermined threshold number;
   in response to the determining, generating, with the server system, a glycemic insight message for delivery to the user, the glycemic insight message comprising information regarding a relationship between at least some of the input data and the particular glycemic outcome;
   delivering the generated glycemic insight message from the server system to the insulin infusion device operated by the user;
   displaying a calendar screen of a calendar application, the calendar screen comprising a scheduled event displayed as a calendar entry, wherein the scheduled event is associated with at least some of the input data, and the glycemic insight message comprises one or more active elements that, when selected, cause additional details related to a relationship between the at least some of the input data and the particular glycemic outcome to be displayed;
   predictively triggering display of the glycemic insight message to appear before the start of the displayed calendar entry;
   displaying the glycemic insight message on the calendar screen of the calendar application, and rendered in association with and proximate to the displayed calendar entry, to link the glycemic insight message contextually and temporally to the scheduled event as an annotation of the displayed calendar entry; and
   adjusting administration of insulin by the insulin infusion device, wherein the adjusting is performed by the insulin infusion device in accordance with recommended glycemic control parameters included in the glycemic insight message delivered to the insulin infusion device.

2. The method of claim 1, wherein the input data comprises:
   a first amount of data provided by the insulin infusion device; and
   a second amount of data provided by a source other than the insulin infusion device.

3. The method of claim 1, wherein the input data comprises data provided by a mobile device operated by the user.

4. The method of claim 1, further comprising:
   obtaining a plurality of generated glycemic insight messages; and
   regulating delivery of at least some of the plurality of generated glycemic insight messages to a user device.

5. The method of claim 1, wherein the glycemic insight message comprises:
   information related to a triggering glycemic event; and
   information related to the particular glycemic outcome.

6. The method of claim 1, wherein the glycemic insight message is generated in association with a glucose profile plot for the user.

7. The method of claim 1, wherein the glycemic insight message is generated in association with a geographical map to provide geographical context to the glycemic insight message.

8. The method of claim 1, further comprising:
sending the glycemic insight message to a mobile device operated by the user for presentation to the user.

9. The method of claim 1, wherein the input data comprises at least some of: carbohydrate amount; bolus information; insulin to carbohydrate ratio; insulin sensitivity factor; active insulin amount; time of day; basal rate; temporary basal use; consecutive boluses; insulin suspension; reservoir rewind time; reservoir priming time; pump alarms and associated alarm times; sensor alerts and associated alert times; blood glucose readings and associated measurement times; user demographic information; meal times and corresponding meal content; exercise times and corresponding exercise content or type; medication type, dosage, and time; sleep time and quality; stress time; electronic medical records; medical lab test data; user reactions to delivered insight messages; and user behavior changes to delivered insight messages.

10. The method of claim 1, wherein the particular glycemic outcome is a direct threshold-based outcome.

11. The method of claim 1, wherein the particular glycemic outcome is a differential outcome having a range of possible states or values describing the relationship between a current outcome and other outcomes.

12. A computer-implemented glycemic insights system comprising:
at least one processor device; and
a non-transitory processor-readable medium operatively associated with the at least one processor device, the processor-readable medium comprising executable instructions configurable to cause the at least one processor device to perform a method comprising:
obtaining input data for a user of an insulin infusion device;
comparing the input data against historical event/outcome combinations maintained for the user, each of the event/outcome combinations comprising insight event data indicative of a respective glycemic event and a respective glycemic outcome corresponding to the insight event data;
determining, based on the comparing, a correlation between the input data and a particular glycemic outcome, the determining step performed by the server system, wherein the determining step comprises:
analyzing the historical event/outcome combinations to count a number of times that an insight event has occurred in a designated historical window of time;
comparing the number of times to a predetermined threshold number; and
confirming that insight generation criteria is satisfied only when the number of times exceeds the predetermined threshold number;
in response to the determining, generating a glycemic insight message for delivery to the user, the glycemic insight message comprising information regarding a relationship between at least some of the input data and the particular glycemic outcome;
delivering the generated glycemic insight message from the server system to the insulin infusion device operated by the user;
displaying a calendar screen of a calendar application, the calendar screen comprising a scheduled event displayed as a calendar entry;
predictively triggering display of the glycemic insight message to appear before the start of the displayed calendar entry;
displaying the glycemic insight message on the calendar screen of the calendar application, and rendered in association with and proximate to the displayed calendar entry, to link the glycemic insight message contextually and temporally to the scheduled event as an annotation of the displayed calendar entry, wherein the scheduled event is associated with at least some of the input data, and the glycemic insight message comprises one or more active elements that, when selected, cause additional details related to a relationship between the at least some of the input data and the particular glycemic outcome to be displayed; and
adjusting administration of insulin by the insulin infusion device, wherein the adjusting is performed by the insulin infusion device in accordance with recommended glycemic control parameters included in the glycemic insight message delivered to the insulin infusion device.

13. The system of claim 12, wherein the input data comprises:
a first amount of data provided by the insulin infusion device; and
a second amount of data provided by a source other than the insulin infusion device.

14. The system of claim 12, wherein the method performed by the at least one processor device further comprises:
sending the glycemic insight message to a mobile device operated by the user for presentation to the user.

* * * * *